(12) United States Patent
Edamatsu et al.

(10) Patent No.: US 6,511,995 B1
(45) Date of Patent: Jan. 28, 2003

(54) PYRIDINE DERIVATIVE AND PHARMACEUTICAL CONTAINING THE SAME

(75) Inventors: Kouji Edamatsu, Daito (JP); Takao Nagahama, Ichikawa (JP); Satoshi Hayakawa, Otsu (JP); Yutaka Kojima, Otsu (JP); Makoto Sakamoto, Shiga (JP); Koichi Yasumura, Otsu (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/646,935

(22) PCT Filed: Mar. 19, 1999

(86) PCT No.: PCT/JP99/01425

§ 371 (c)(1),
(2), (4) Date: Sep. 25, 2000

(87) PCT Pub. No.: WO99/48871

PCT Pub. Date: Sep. 30, 1999

(30) Foreign Application Priority Data

Mar. 25, 1998 (JP) .............................. 10-078083
Sep. 4, 1998 (JP) .............................. 10-251552

(51) Int. Cl.$^7$ ...................... C07D 213/12; A61K 31/44
(52) U.S. Cl. ...................... 514/329; 514/336; 514/278; 546/15; 546/283.7; 546/297
(58) Field of Search ............................. 546/297, 283.7; 514/329, 336

(56) References Cited

U.S. PATENT DOCUMENTS 6,022,884 A * 2/2000 Mantlo et al. ............. 514/352

FOREIGN PATENT DOCUMENTS

EP         0 562 512 A1    9/1993
WO         WO 99/24404     5/1999

* cited by examiner

*Primary Examiner*—Jane Fan
(74) *Attorney, Agent, or Firm*—Finnegan, Henderson, Farabow, Garrett & Dunner LLP

(57) ABSTRACT

A pyridine derivative represented by formula (1) wherein all the variables have been defined in the specification. The compounds are used for inhibiting collagen production and are useful for preventing or treating fibrosis.

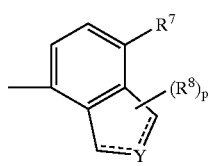

(1)

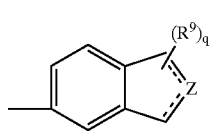

(A1)

(A2)

(A3)

28 Claims, No Drawings

PYRIDINE DERIVATIVE AND PHARMACEUTICAL CONTAINING THE SAME

This application is a 371 of PCT/JP99/01425, Mar. 19, 1999 now WO 99/48,871.

TECHNICAL FILED

The present invention relates to a novel pyridine derivative or a salt thereof, which inhibits collagen synthesis, and a pharmaceutical containing said compound, which is useful for prophylaxis or treatment of fibrosis.

BACKGROUND ART

At present, it is said that 130 or more types of diseases exist as diseases referred to as fibrosis, including rare diseases. Typical disease of fibrosis includes, for example, pulmonary fibrosis, hepatic fibrosis, glomerulosclerosis, etc.

Pulmonary fibrosis generally refers to syndrome wherein the function of lung is lost because of reconstructed lesion in the alveror region, that is, an alveolar structure is broken by the inflammatory reaction to cause growth of fibroblasts and excess increase in extracellular matrix composed mainly of collagen, resulting in lung sclerosis.

On the other hand, hepatic fibrosis refers to the condition of diseases wherein necrosis of hepatocytes is caused by various hepatopathy such as chronic virus hepatitis, alcoholic hepatopathy, etc. and, thereafter, extracellular matrix increases to recruit for the site, resulting in hepatic fibrogenesis. The terminal status of this condition of disease leads to liver cirrhosis wherein the whole liver tissue atrophies and scleroses.

Conventional drugs which inhibit hepatic fibrogenesis described above includes, for example, penicillamine known as a remedy for Wilkinson's disease which occurs due to accumulation of copper in liver as a result of abnormal metabolism of copper, Lufironil which has been studied as a proline hydroxylase inhibitor, etc.

However, these drugs are not sufficient as a drug for preventing hepatic fibrogenesis in view of side effects and validity. At present, a remedy (or therapy) which is effective for fibrosis represented by hepatic fibrogenesis has not been established, and it has been studied how the process of causing fibrogenesis is specifically inhibited.

As described above, it has been known that an excess increase in extracellular matrix composed mainly of collagen occurs in the process of causing fibrogenesis in lung tissues and hapatocytes. It has also been known that an increase in extracellular matrix in hepatocytes mainly occurs in a sinusoid wall Disse space and that Ito cells as mesenchymal cells of liver constitute a main production source.

Accordingly, it is important that an excess increase in extracellular matrix (i.e. collagen) is inhibited to inhibit fibrogenesis in liver, lung, etc.

Thus, an object of the present invention is to provide a novel compound which is superior in effect of inhibiting production of collagen, and a pharmaceutical containing the same, which is useful for prophylaxis or treatment of fibrosis.

DISCLOSURE OF THE INVENTION

The present inventors have intensively studied to solve the problems described above. As a result, they have obtained such a knowledge that a pyridine derivative represented by the general formula (1) described below and a pharmaceutically acceptable salt thereof are superior in effect of inhibiting collagen production, thus completing the present invention.

Thus, the present invention mainly relates to:

(1) A pyridine derivative represented by the general formula (1):

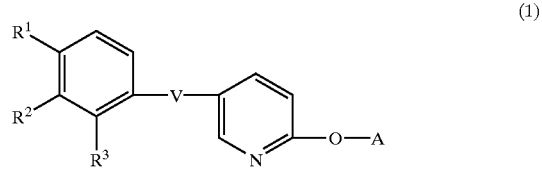

wherein $R^1$ represents a halogen atom or a halogen-substituted lower alkyl group; $R^2$ and $R^3$ are the same or different and represent a hydrogen atom or a halogen atom; V represents a group: —C(=O)—H, a group: —NH—C(=O)—, a group: —NH—C(=O)—NH—or a group: —CH=CH—; A represents a group $A^1$:

(wherein $R^4$ represents a hydrogen atom, a lower alkanoyl group, a benzoyl group, a 2-lower alkyl-1,3-dioxolane group or a hydroxy-substituted lower alkyl group; $R^5$ represents a hydrogen atom, a 2-lower alkyl-1,3-dioxolane group, a lower alkyl group or a lower alkanoyl group; and $R^6$ represents a hydrogen atom, a lower alkyl group or a lower alkanoyl group), a group $A^2$:

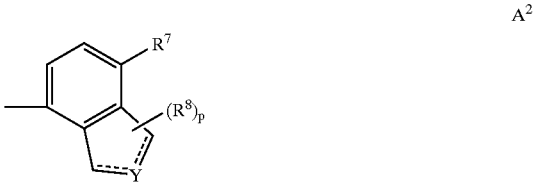

(wherein $R^7$ represents a hydrogen atom or a lower alkyl group; and $R^8$ is the same or different and represents a hydrogen atom, a hydroxyl group, an oxo group, a lower alkanoyloxy group, an aroyloxy group, a lower alkoxy group, a group:

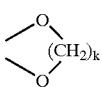

(wherein k represents an integer of 1 to 3) or a group: =N—$OR^{10}$ ($R^{10}$ represents a hydrogen atom, a lower alkyl group or a lower alkanoyl group); p represents an integer of 1 to 2;

represents a single bond or a double bond; Y represents a group: —(CH$_2$)$_m$—, a group: =CH(CH$_2$)$_{m-1}$— or a group: —(CH$_2$)$_{m-1}$CH=; and m represents an integer of 1 to 3) or a group A$^3$:

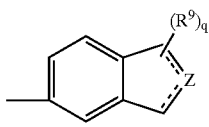

(wherein R$^9$ is the same or different and represents a hydrogen atom, a hydroxyl group, an oxo group, a lower alkanoyloxy group, an aroyloxy group, a lower alkoxy group, a group:

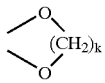

(wherein k represents an integer of 1 to 3) or a group: =N—OR$^{10}$ (R$^{10}$ represents a hydrogen atom, a lower alkyl group or a lower alkanoyl group); q represents an integer of 1 to 2; represents a single bond or a double bond; Z represents a group: —(CH$_2$)$_n$—, a group: =CH(CH$_2$)$_{n-1}$— or a group: —(CH$_2$)$_{n-1}$CH=; and n represents an integer of 1 to 3)] or a salt thereof;

(2) A pharmaceutical comprising a compound of the general formula (1) in claim 1 or a pharmaceutically acceptable salt thereof;

(3) A pharmaceutical composition for prophylaxis or treatment of fibrosis, which comprises an effective amount of a compound of the general formula (1) in claim 1 or a pharmaceutically acceptable salt thereof and a pharmaceutically acceptable carrier, diluent and/or excipient; and (4) A method for inhibiting fibrogenesis caused by excess production of collagen in a mammal which comprises administering to said mammal a pharmaceutically effective amount of a compound of the general formula (1) in claim 1 or a pharmaceutically acceptable salt thereof.

The pyridine derivative (1) or a pharmaceutically acceptable salt thereof are superior in effect of inhibiting collagen production, as described above, and has characteristics such as long duration time of drug efficacy, good transition in blood and low toxicity.

Accordingly, the pyridine derivative (1) or a salt thereof is effective for prophylax or treatment of diseases attended with fibrogenesis caused by excess production of collagen, for example, (i) organ diseases such as sudden and interstitial pulmonary fibrosis, pneumoconiosis, ARDS, hepatic fibrosis, neonatal hepatic fibrosis, hepatic cirrhosis, mucoviscidosis and myelofibrosis; (ii) dermal diseases such as scleroderma, elephantiasis, morphea, injury and hypertrophic cicatrix and keloid after burn injury; (iii) vascular diseases such as atherosclerosis and arteriosclerosis; (iv) ophthalmic diseases such as diabetic retinopathy, fibroplasia retrolentalis, vascularization arising along with corneal transplantation, glaucoma, proliferative vitreoretinopathy and corneal cicatrix after operation; (v) renal diseases such as contracted kidney, nephrosclerosis, interstitial nephritis, IgA nephritis, glomerulosclerosis, membranoproliferative nephritis, diabetic nephropathy, chronic interstitial nephritis and chronic glomerulonephritis; and (vi) diseases in cartilage or bone, such as rheumatic arthritis, chronic arthritis and osteoarthritis.

Among them, the pyridine derivative (1) and a salt thereof of the present invention is superior in effect of inhibiting fibrogenesis attended with the organ diseases listed in the above item (i), and can be used as a preventive or a remedy for pulmonary fibrosis and hepatic fibrosis.

The pyridine derivative represented by the general formula (1) of the present invention includes, for example, the following compounds:

(1–1) a pyridine derivative wherein R$^1$ to R$^3$, R$^7$ to R$^{10}$, m, n, p, q, k, V, Y and Z are as defined in the general formula (1) and A is a group A$^2$ or a group A$^3$, or a pharmaceutically acceptable salt thereof;

(1–2) a pyridine derivative, wherein R$^1$ to R$^6$ and V are as defined in the general formula (1) and A is a group A$^1$, or a pharmaceutically acceptable salt thereof;

(1–3) a pyridine derivative wherein R$^1$ to R$^3$, R$^7$ to R$^8$, m, p, k, V and Y are as defined in the general formula (1) and A is a group A$^2$, or a pharmaceutically acceptable salt thereof;

(1–4) a pyridine derivative wherein R$^1$ to R$^3$, R$^9$, R$^{10}$, n, q, k, V and Z are as defined in the general formula (1) and A is a group A$^3$, or a pharmaceutically acceptable salt thereof;

(1–5) a pyridine derivative wherein R$^1$ to R$^{10}$, m, n, p, q, k, A, Y and Z are as defined in the general formula (1), V is a group —C(=O)—NH—, —NH—C(=O)—NH— or —NH—C(=O)—, or a pharmaceutically salt thereof;

(1–6) a pyridine derivative wherein R to R m, n, p, q, k, A, Y and Z are as defined in the general formula (1) and V is a group —C(=O)—NH—, or a pharmaceutically acceptable salt thereof;

(1–7) a pyridine derivative wherein R$^1$ to R$^{10}$, m, n, p, q, k, A, Y and Z are as defined in the general formula (1) and V is a group —NH—C(=O)—NH—, or a pharmaceutically acceptable salt thereof;

(1–8) a pyridine derivative wherein R$^1$ to R$^{10}$, m, n, p, q, k, A, Y and Z are as defined in the general formula (1) and V is a group,—NH—C(=O)—, or a pharmaceutically acceptable salt thereof;

(1–9) a pyridine derivative wherein R$^1$ to R$^3$, R$^1$ to R$^{10}$, n, m, p, q, k, Y and Z are as defined in the general formula (1), V is a group —NH—C(=O)—NH— and A is a group A$^2$ or a group A$^3$, or a pharmaceutically acceptable salt thereof;

(1–10) a pyridine derivative wherein R$^1$ to R$^6$ are as defined in the general formula (1) and V is a group —NH—C(=O)—, or a pharmaceutically acceptable salt thereof;

(1–11) a pyridine derivative wherein R$^1$ to R$^3$, R$^7$, R$^8$, m, p, k and Y are as defined in the general formula (1), V is a group —NH—C(=O)—NH— and A is a group A$^2$, or a pharmaceutically acceptable salt thereof;

(1–12) a pyridine derivative wherein R$^1$ to R$^3$, R$^7$, R$^8$, m, p, k and Y are as defined in the general formula (1), V is a group —NH—C(=O)— and A is a group A$^2$, or a pharmaceutically acceptable salt thereof;

(1–13) a pyridine derivative wherein R$^1$ to R$^3$, R$^9$, R$^{10}$, q, k, n and Z are as defined in the general formula (1), V is a group —NH—C(=O)—NH— and A is a group A$^3$, or a pharmaceutically acceptable salt thereof;

(1–14) a pyridine derivative wherein R$^1$ to R$^3$, R$^7$ to R$^{10}$, n, m, p, q, k, Y and Z are as defined in the general formula (1), V is a group —C(=O)—NH— and A is a group A$^2$ or a group A$^3$, or a pharmaceutically acceptable salt thereof;

(1–15) a pyridine derivative wherein R$^1$ to R$^6$ are as defined in the general formula (1), V is a group —C(=O)—NH—and A is a group A$^1$, or a pharmaceutically acceptable salt thereof;

(1–16) a pyridine derivative wherein R$^1$ to R$^3$, R$^7$, R$^8$$_1$ m, p, k and Y are as defined in the general formula (1), V is a group —C(=O)—NH— and A is a group $A^2$, or a pharmaceutically acceptable salt thereof;

(1–17) a pyridine derivative wherein $R^1$ to $R^3$, $R^9$, $R^{10}$, n, q, k and Z are as defined in the general formula (1), V is a group —C(=O)—NH— and A is a group $A^3$, or a pharmaceutically acceptable salt thereof;

(1–18) a pyridine derivative wherein $R^3$ to $R^{10}$, n, m, p, q, k, V, Y, Z and A are as defined in the general formula (1) and $R^1$ and $R^2$ are respectively a halogen atom, or a pharmaceutically acceptable salt thereof;

(1–19) a pyridine derivative wherein $R^2$ to $R^{10}$, n, m, p, q, k, V, Y, Z and A are as defined in the general formula (1) and $R^1$ is a halogen-substituted lower alkyl group, or a pharmaceutically acceptable salt thereof;

(1–20) a pyridine derivative wherein $R^2$, $R^3$, $R^7$ to $R^{10}$, n, m, p, q, k, V, Y and Z are as defined in the general formula (1), $R^1$ is a halogen-substituted lower alkyl group and A is a group $A^2$ or a group $A^3$, or a pharmaceutically acceptable salt thereof;

(1–21) a pyridine derivative wherein $R^2$ and $R^3$ to $R^6$ are as defined in the general formula (1), $R^1$ is a halogen-substituted lower alkyl group and A is a group $A^1$, or a pharmaceutically acceptable salt thereof;

(1–22) a pyridine derivative wherein $R^2$, $R^3$, $R^7$, $R^8$, m, p, k, V and Y are as defined in the general formula (1), $R^1$ is a halogen-substituted lower alkyl group and A is a group $A^2$, or a pharmaceutically acceptable salt thereof;

(1–23) a pyridine derivative wherein $R^2$, $R^3$, $R^9$, $R^{10}$, n, q, k, V and Z are as defined in the general formula (1), $R^1$ is a halogen-substituted lower alkyl group and A is a group $A^3$, or a pharmaceutically acceptable salt thereof;

(1–24) a pyridine derivative wherein $R^3$, $R^7$ to $R^{10}$, n, m, p, q, k, V, Y and Z are as defined in the general formula (1), $R^1$ and $R^2$ are respectively a halogen atom and A is a group $A^2$ or a group $A^3$, or a pharmaceutically acceptable salt thereof;

(1–25) a pyridine derivative wherein $R^3$ to $R^6$ and V are as defined in the general formula (1), $R^1$ and $R^2$ are respectively a halogen atom and A is a group $A^1$, or a pharmaceutically acceptable salt thereof;

(1–26) a pyridine derivative wherein $R^3$, $R^7$, $R^8$, m, p, k, V and Y are as defined in the general formula (1), $R^1$ and $R^2$ are respectively a halogen atom and A is a group $A^2$, or a pharmaceutically acceptable salt thereof;

(1–27) a pyridine derivative wherein $R^3$, $R^9$, $R^{10}$, n, q, k, V and Z are as defined in the general formula (1), $R^1$ and $R^2$ are respectively a halogen atom and A is a group $A^3$, or a pharmaceutically acceptable salt thereof;

(1–28) a pyridine derivative wherein $R^2$, $R^3$, $R^7$ to $R^{10}$, n, m, p, q, k, Y and Z are as defined in the general formula (1), $R^1$ is a halogen-substituted lower alkyl group, A is a group $A^2$ or a group $A^3$ and V is a group —C(=O)—NH—, or a pharmaceutically acceptable salt thereof;

(1–29) a pyridine derivative wherein $R^2$ to $R^6$ are as defined in the general formula (1), $R^1$ is a halogen-substituted lower alkyl group, A is a group $A^1$ and V is a group —C(=O)—NH—, or a pharmaceutically acceptable salt thereof;

(1–30) a pyridine derivative wherein $R^2$, $R^3$, $R^7$, $R^8$, m, p, k and Y are as defined in the general formula (1), $R^1$ is a halogen-substituted lower alkyl group, A is a group $A^2$ and V is a group —C(=O)—NH—, or a pharmaceutically acceptable salt thereof;

(1–31) a pyridine derivative wherein $R^2$, $R^3$, R9, $R^{10}$, n, q, k and Z are as defined in the general formula (1), $R^1$ is a halogen-substituted lower alkyl group, A is a group $A^3$ and V is a group —C(=O)—NH—, or a pharmaceutically acceptable salt thereof;

(1–32) a pyridine derivative wherein $R^3$, $R^7$ to $R^{10}$ n, m, p, q, k, Y and Z are as defined in the general formula (1), $R^1$ and $R^2$ are respectively a halogen atom, A is a group $A^2$ or a group $A^3$ and V is a group —C(=O)—NH—, or a pharmaceutically acceptable salt thereof;

(1–33) a pyridine derivative wherein $R^3$ to $R^6$ are as defined in the general formula (1), $R^1$ and $R^2$ are respectively a halogen atom, A is a group $A^1$ and V is a group —C(=O)—NH—, or a pharmaceutically acceptable salt thereof;

(1–34) a pyridine derivative wherein $R^3$, $R^7$, $R^8$, m, p, k and Y are as defined in the general formula (1), $R^1$ and $R^2$ are respectively a halogen atom, A is a group A and V is a group —C(=O)—NH—, or a pharmaceutically acceptable salt thereof;

(1–35) a pyridine derivative wherein $R^3$, $R^9$, $R^1$ n, q, k and Z are as defined in the general formula (1), $R^1$ and $R^2$ are respectively a halogen atom, A is a group $A^3$ and V is a group —C(=O)—NH—, or a pharmaceutically acceptable salt thereof;

(1–36) a pyridine derivative wherein $R^2$, $R^3$, $R^7$ to $R^{10}$, n, m, p, q, k, Y and Z are as defined in the general formula (1), $R^1$ is a halogen-substituted lower alkyl group, A is a group $A^2$ or a group $A^3$ and V is a group —NH—C(=O)—, or a pharmaceutically acceptable salt thereof;

(1–37) a pyridine derivative wherein $R^2$, $R^3$, $R^7$ to $R^{10}$, n, m, p, q, k, Y,and Z are as defined in the general formula (1), $R^1$ is a halogen-substituted lower alkyl group, A is a group $A^2$ or a group $A^3$ and V is a group —NH—C(=O)—NH—, or a pharmaceutically acceptable salt thereof;

(1–38) a pyridine derivative wherein $R^2$ to $R^6$ are as defined in the general formula (1), $R^1$ is a halogen-substituted lower alkyl group, A is a group $A^1$ and V is a group —NH—C(=O)—, or a pharmaceutically acceptable salt thereof;

(1–39) a pyridine derivative wherein $R^2$, $R^3$, $R^7$, $R^8$, m, p, k and Y are as defined in the general formula (1), $R^1$ is a halogen-substituted lower alkyl group, A is a group $A^2$ and V is a group —NH—C(=O)—, or a pharmaceutically acceptable salt thereof;

(1–40) a pyridine derivative wherein $R^2$, $R^3$, $R^7$, $R^8$, m, p, k and Y are as defined in the general formula (1), $R^1$ is a halogen-substituted lower alkyl group, A is a group $A^2$ and V is a group —NH—C(=O)—NH—, or a pharmaceutically acceptable salt thereof;

(1–41) a pyridine derivative wherein $R^2$, $R^3$, $R^9$, $R^{10}$, n, q, k and Z are as defined in the general formula (1), $R^1$ is a halogen-substituted lower alkyl group, A is a group $A^3$ and V is a group —NH—C(—O)—NH—, or a pharmaceutically acceptable salt thereof;

(1–42) a pyridine derivative wherein $R^3$, $R^7$ to $R^{10}$, n, m, p, q, k, Y and Z are as defined in the general formula (1), $R^1$ and $R^2$ are respectively a halogen atom, A is a group $A^2$ or a group $A^3$ and V is a group —NH—C(=O)—NH—, or a pharmaceutically acceptable salt thereof;

(1–43) a pyridine derivative wherein $R^3$ to $R^6$ are as defined in the general formula (1), $R^1$ and $R^2$ are respectively a halogen atom, A is a group $A^1$ and V is a group —NH—C(=O)—, or a pharmaceutically acceptable salt thereof;

(1–44) a pyridine derivative wherein $R^3$, $R^7$, $R^8$, m, p, k and Y are as defined in the general formula (1), $R^1$ and $R^2$ are respectively a halogen atom, A is a group $A^2$ and V is a group —NH—C(=O)—NH—, or a pharmaceutically acceptable salt thereof;

(1–45) a pyridine derivative wherein $R^3$, $R^9$, $R^{10}$, n, q, k and Z are as defined in the general formula (1), $R^1$ and $R^2$ are respectively a halogen atom, A is a group $A^3$ and V is a group —NH—C(=O)—NH—, or a pharmaceutically acceptable salt thereof;

(1–46) a pyridine derivative wherein $R^1$ to $R^3$, $R^7$ to $R^9$, p, q, k, V, Y and Z are as defined in the general formula (1), A is a group $A^2$ or a group $A^3$ and m and n are respectively 1, or a pharmaceutically acceptable salt thereof;

(1–47) a pyridine derivative wherein $R^1$ to $R^3$, $R^7$, $R^8$, p, k, V and Y are as defined in the general formula (1), A is a group $A^2$ and m is 1, or a pharmaceutically acceptable salt thereof;

(1–48) a pyridine derivative wherein $R^1$ to $R^3$, $R^9$, $R^{10}$, q, k, V and Z are as defined in the general formula (1), A is a group $A^3$ and n is 1, or a pharmaceutically acceptable salt thereof;

(1–49) a pyridine derivative wherein $R^1$ to $R^3$, $R^7$, p, q, k, V, Y and Z are as defined in the general formula (1), A is a group $A^2$ or a group $A^3$, m and n are respectively 1 and $R^8$ and $R^9$ are respectively an oxo group, or a pharmaceutically acceptable salt thereof;

(1–50) a pyridine derivative wherein $R^1$ to $R^3$, $R^7$, p, q, k, V and Z are as defined in the general formula (1), A is a group $A^2$ or $A^3$, m and n are respectively 1, and $R^8$ and $R^9$ are respectively lower alkanoyoxy group, or a pharmaceutically acceptable salt thereof;

(1–51) a pyridine derivative wherein $R^1$ and $R^2$ are respectively a halogen atom, $R^3$ is a hydrogen atom, V is a group: —C(=O)—NH—, A is a group $A^2$, $R^7$ is a hydrogen atom, $R^8$ is an oxo group, a lower alkanoyloxy group or a hydroxyl group, Y is a group: —(CH$_2$)$_m$— or —(CH$_2$)$_{m-1}$CH= and m is 1, or a pharmaceutically acceptable salt thereof;

(1–52) a pyridine derivative wherein $R^1$ is a halogen-substituted lower alkyl group, $R^2$ and $R^3$ are respectively a hydrogen atom, V is a group: —C(=O)—NH—, A is a group $A^2$, $R^7$ is a hydrogen atom, $R^8$ is an oxo group or a lower alkanoyloxy group, Y is a group: —(CH$_2$)$_m$— or —(CH$_2$)$_{m-1}$CH= and m is 1, or a pharmaceutically acceptable salt thereof;

(1–53) a pyridine derivative wherein $R^1$ and $R_2$ are respectively a halogen atom, $R^3$ is a hydrogen atom, V is a group: —C(=O)—NH—, A is a group $A^2$, $R^7$ is a hydrogen atom, $R^8$ is an oxo group or a lower alkanoyloxy group, Y is a group: —(CH$_2$)$_m$— or —(CH$_2$)$_{m-1}$CH= and m is 2, or a pharmaceutically acceptable salt thereof;

(1–54) a pyridine derivative wherein $R^1$ and $R^2$ are respectively a halogen atom, $R^3$ is a hydrogen atom, V is a group: —C(=O)—NH—, A is a group $A^2$, $R^7$ is a hydrogen atom, $R^8$ is an oxo group or a lower alkanoyloxy group, Y is a group: —(CH$_2$)$_m$— or —(CH$_2$)$_{m-1}$CH= and m is 3, or a pharmaceutically acceptable salt thereof;

(1–55) a pyridine derivative wherein $R^1$ and $R^2$ are respectively a halogen atom, $R^3$ is a hydrogen atom, V is a group: —C(=O)—NH—, A is a group $A^1$, $R^4$ is a 2-lower alkyl-1,3-dioxolane group, $R^5$ is a hydrogen atom and $R^6$ is a hydrogen atom, or a pharmaceutically acceptable salt thereof;

(1–56) a pyridine derivative wherein $R^1$ and $R^2$ are respectively a halogen atom, $R^3$ is a hydrogen atom, V is a group: —NH—C(=O)—NH—, A is a group $A^2$, $R^7$ is a hydrogen atom, $R^8$ is an oxo group or a lower alkanoyloxy group, Y is a group: —(CH$_2$)$_m$— or —(CH$_2$)$_{m-1}$CH= and m is 1 or 2, or a pharmaceutically acceptable salt thereof;

(1–57) a pyridine derivative wherein Z is as defined in the general formula (1), $R^1$ and $R^2$ are respectively a halogen atom, $R^3$ is a hydrogen atom, V is a group: —NH—C(=O)—NH—, A is a group $A^3$, $R^9$ is an oxo group or a lower alkanoyloxy group and n is 1, or a pharmaceutically acceptable salt thereof;

(1–58) a pyridine derivative wherein $R^1$ is a halogen-substituted lower alkyl group, $R^2$ and $R^3$ are respectively a hydrogen atom, V is a group: —NH—C(=O)—NH—, A is a group $A^2$, $R^7$ is a hydrogen atom, $R^8$ is an oxo group or a lower alkanoyloxy group, Y is a group: —(CH$_2$)$_m$— and m is 1, or a pharmaceutically acceptable salt thereof;

(1–59) a pyridine derivative wherein $R^1$ is a halogen-substituted lower alkyl group, $R^2$ and $R^3$ are respectively a hydrogen atom, V is a group: —NH—C(=O)—, A is a group $A^2$, $R^7$ is a hydrogen atom, $R^8$ is an oxo group or a lower alkanoyloxy group, Y is a group: —(CH$_2$)$_m$— and m is 1, or a pharmaceutically acceptable salt thereof;

(1–60) a pyridine derivative wherein $R^1$ and $R^2$ are respectively a halogen atom, $R^3$ is a hydrogen atom, V is a group: —C(=O)—NH—, A is a group $A^2$, $R^7$ is a hydrogen atom, $R^8$ is a hydrogen atom and Y is a group: =CH(CH$_2$)$_{m-1}$— or a group: —(CH$_{2m-1}$CH=, or a pharmaceutically acceptable salt thereof;

(1–61) a pyridine derivative wherein $R^1$ and $R^2$ are respectively a halogen atom, $R^3$ is a hydrogen atom, V is a group: —C(=O)—NH—, A is a group $A^1$, $R^4$ is a hydrogen atom, $R^5$ is a lower alkyl group and $R^6$ is a lower alkyl group, or a pharmaceutically acceptable salt thereof;

(1–62) a pyridine derivative wherein $R^1$ and $R^2$ are respectively a halogen atom, $R^3$ is a hydrogen atom, V is a group: —C(=O)—NH—, A is a group $A^1$, $R^4$ is a lower alkanoyl group and $R^5$ and $R^6$ are respectively a hydrogen atom, or a pharmaceutically acceptable salt thereof;

(1–63) a pyridine derivative wherein $R^1$ and $R^2$ are respectively a halogen atom, $R^3$ is a hydrogen atom, V is a group: —NH—C(=O)—, A is a group $A^1$, $R^4$ is a lower alkanoyl group and $R^5$ and $R^6$ are respectively a hydrogen atom, or a pharmaceutically acceptable salt thereof;

(1–64) a pyridine derivative wherein $R^1$ is a halogen-substituted lower alkyl group, $R^2$ and $R^3$ are respectively a hydrogen atom, V is a group: —NH—C(=O)—, A is a group $A^1$, $R^4$ is a lower alkanoyl group and $R^5$ and $R^6$ are respectively a hydrogen atom, or a pharmaceutically acceptable salt thereof;

(1–65) a pyridine derivative wherein $R^1$ is a halogen-substituted lower alkyl group, $R^2$ and $R^3$ are respectively a hydrogen atom, V is a group: —C(=O)—NH—, A is a group $A^1$, $R^4$ is a lower alkanoyl group, $R^5$ is a hydrogen atom or a lower alkyl group and $R^6$ is a hydrogen atom, or a pharmaceutically acceptable salt thereof; and (1–66) a pyridine derivative wherein $R^1$ and $R^2$ are respectively a halogen atom, $R^3$ is a hydrogen atom, V is a group: —C(=O)—NH—, A is a group $A^2$, Y is a group: —(CH$_2$)$_m$—, m is 1, $R^7$ is a hydrogen atom or a lower alkyl group and $R^8$ is a hydrogen atom, or a pharmaceutically acceptable salt thereof.

The respective groups shown in the general formula (1) are specifically explained as follows.

The lower alkyl group includes, for example, straight-chain or branched alkyl group having 1 to 6 carbon atoms, such as methyl, ethyl, propyl, isopropyl, butyl, isobutyl, s-butyl, t-butyl, pentyl and hexyl.

The hydroxy-substituted lower alkyl group includes, for example, hydroxy lower alkyl group whose alkyl moiety is a straight-chain or branched alkyl group having 1 to 6 carbon atoms, such as hydroxymethyl, 2-hydroxyethyl, 1,1-dimethyl-2-hydroxyethyl, 3-hydroxypropyl, 4-hydroxybutyl, 2-hydroxybutyl, 5-hydroxypentyl, 1-hydroxypentyl and 6-hydroxyhexyl.

The halogen-substituted lower alkyl group includes, for example, alkyl group having 1 to 6 carbon atoms which is substituted with 1 to 3 halogen atoms, such as monochloromethyl, monobromomethyl, monoiodomethyl, monofluoromethyl, dichloromethyl, dibromomethyl, diiodomethyl, difluoromethyl, trichloromethyl, tribromomethyl, triiodomethyl, trifluoromethyl, monochloroethyl, monobromoethyl, monoiodoethyl, dichloroethyl, dibromoethyl, difluoroethyl, dichlorobutyl, diiodobutyl, difluorobutyl, chlorohexyl, bromohexyl and fluorohexyl.

The 2-lower alkyl-1,3-dioxolane group includes, for example, 2-lower alkyl-1,3-dioxolane group whose alkyl moiety is an alkyl group having 1 to 6 carbon atoms, such as 2-methyl-1,3-dioxolane, 2-ethyl-1,3-dioxolane and 2-propyl-1,3-dioxolane, 2-butyl-1,3-dioxolane and 2-hexyl-1,3-dioxolane.

The halogen atom include, for example, fluorine, chlorine, bromine and iodine.

The alkanoyl moiety of the lower alkanoyloxy group and lower alkanoyl group includes, for example, straight-chain or branched alkanoyl group whose alkyl moiety has 1 to 6 carbon atoms, such as formyl, acetyl, propionyl, butyryl, isobutyryl, valeryl, isovaleryl, pivaloyl, pentanoyl and hexanoyl.

The aroyl moiety of the aroyloxy group includes, for example, benzoyl, toluoyl, naphthoyl, salicyloyl, anisoyl and phenanthoyl.

The lower alkoxy group includes, for example, straight-chain or branched alkoxy group having 1 to 6 carbon atoms, such as methoxy, ethoxy, propoxy, isopropoxy, butoxy, t-butoxy, pentyloxy and hexyloxy.

The process for producing the pyridine derivative (1) of the present invention will be explained below.
Reaction Scheme (I-a):

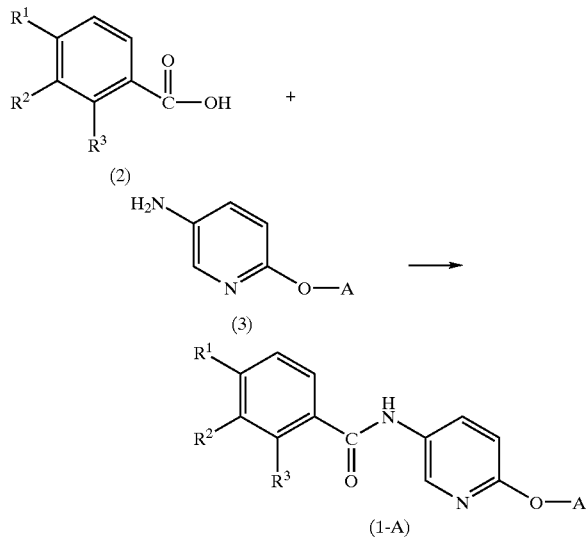

(wherein $R^1$, $R^2$, $R^3$ and A are as defined above)

This reaction is a process for obtaining a pyridine derivative (1-A) wherein V is —C(=O)—NH— of the present invention. That is, the pyridine derivative (1-A) is obtained by condensing a carboxylic acid (2) with a 3-aminopyridine derivative (3) in a state free from solvent or in a suitable solvent, using a water-soluble carbodiimide such as 1-ethyl-3-(3-dimethylaminopropyl)carbodiimide hydrochloride as a condensing agent or a carbodiimide such as N,N-dicyclohexylcarbodiimide (DCC).

In that case, when tertiary amine is added, basicity of the amine compound (3) is improved and, therefore, the reaction proceeds.

In the present invention, a condensing agent such as isobutyl chloroformate, diphenyl phosphinic chloride and carbonyl diimidazole may also be used in place of the carbodiimide.

The solvent may be any one which does not adversely affect the reaction, and examples thereof include an inert solvent such as tetrahydrofuran (THF), N,N-dimethylformamide (DMF), dimethyl sulfoxide (DMSO), acetonitrile, toluene and 1,2-dimethoxyethane.

The tertiary amine includes, for example, triethylamine, tributylamine, pyridine, N-methylmorpholine, quinoline, lutidine and 4-dimethylaminopyridine.

The condensing agent is used in the amount of at least 1 mol, and preferably from 1 to 5 mol, per mol of the compound (2).

The 3-aminopyridine derivative (3) is used in the amount of at least 1 mol, and preferably from 1 to 5 mol, per mol of the compound (2).

The reaction is usually carried out by adding the condensing agent to the carboxylic acid (2) at about −20 to 180° C., and preferably 0 to 150° C., for 5 minutes to 3 hours and further adding the 3-aminopyridine derivative (3), and the reaction is completed within about 30 minutes to 30 hours after adding 3-aminopyridine derivative (3).

Reaction Scheme (1-b):

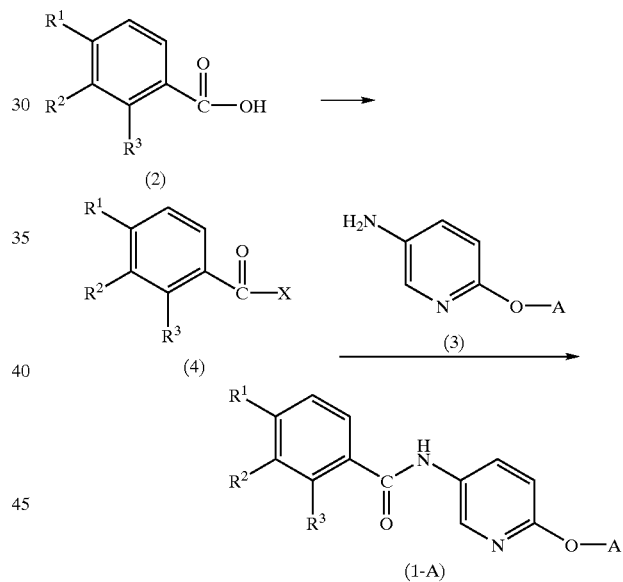

(wherein $R^1$ to $R^3$ and A are as defined above, and X represents a halogen atom)

This reaction is another process for obtaining the pyridine derivative (1-A). That is, the pyridine derivative (1-A) is obtained by reacting a carboxylic acid (2) with a suitable halogenating. agent in a state free from solvent or in a suitable solvent to obtain an acid halide (4), and reacting the acid halide (4) with a 3-aminopyridine derivative (3).

In that case, hydrogen halide is removed from the reaction system by adding tertiary amine and, therefore, the reaction proceeds.

The solvent used in this reaction includes, for example, ethers such as diethyl ether, tetrahydrofuran and dioxane; halogenated hydrocarbon such as methylene chloride, chloroform and dichloroethane; aromatic hydrocarbon such as benzene and toluene; and N,N-dimethylformamide (DMF).

The halogenating agent includes, for example, thionyl halide such as thionyl chloride and thionyl bromide; hydrogen halide such as hydrogen chloride, hydrogen bromide and hydrogen iodide; and phosphorous halide such as phosphorous trichloride and phosphorous tribromide.

The amount of the halogenating agent used is at least 1 mol, and preferably from 1 to 5 mol, per mol of the carboxylic acid (2).

The amount of the 3-aminopyridine derivative (3) used is at least 1 mol, and preferably from 1 to 5 mol, per mol of the acid halide (4).

The reaction is carried out at about −20 to 180° C., and preferably from 0 to 150° C., and is completed within about 5 minutes to 30 hours.

Reaction Scheme (II):

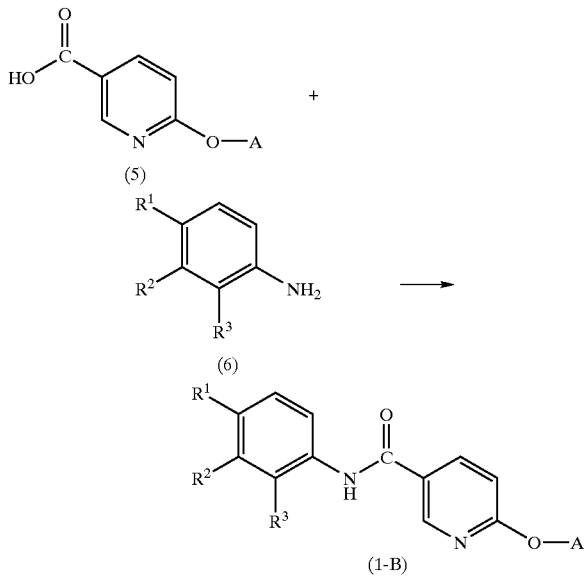

(wherein $R^1$, $R^2$, $R^3$ and A are as defined above) This reaction is a process for obtaining the pyridine derivative (1-B) wherein V is —NH—C(=O)— of the present invention. That is, the pyridine derivative (1-B) of the present invention is obtained by reacting pyridinecarboxylic acid (5) with an aniline derivative (6) according to the process described in the above reaction scheme (I-a).

The solvent, tertiary amine and condensing agent used include, for example, those listed in the above reaction scheme (I-a).

The condensing agent is used in the amount of at least 1 mol, and preferably from 1 to 5 mol, per mol of the pyridinecarboxylic acid (5).

The aniline derivative (6) is used in the amount of at least 1 mol, and preferably from 1 to 5 mol, per mol of the pyridinecarboxylic acid (5).

The reaction is usually carried out by adding the condensing agent to the pyridinecarboxylic acid (5) at about −20 to 180° C., and preferably 0 to 150° C., for 5 minutes to 3 hours and further adding the aniline derivative (6), and the reaction is completed within about 30 minutes to 30 hours after adding the aniline derivative (6).

In the pyridine derivative (1) of the present invention, pyridine derivatives of the following items ① to ② may be produced by reducing a pyridine derivative (1-a) wherein at least one of $R^8$ is an oxo group or a pyridine derivative (1-a') wherein at least one of $R^9$ is an oxo group.

① a pyridine derivative (1-b) wherein Y in the group $A^2$ in A is a group: —$(CH_2)_m$— and at least one of $R^8$ is a hydroxyl group ② a pyridine derivative (1-b') wherein Z in the group $A^3$ in A is a group: —$(CH_2)_m$— and at least one of $R^9$ is a hydroxyl group For example, the pyridine derivative (1-b) of the item ① is obtained by reducing the pyridine derivative (1-a) wherein at least one of $R^8$ is an oxo group in a suitable solvent, as shown in the following reaction scheme (III-a).

Reaction Scheme (III-a):

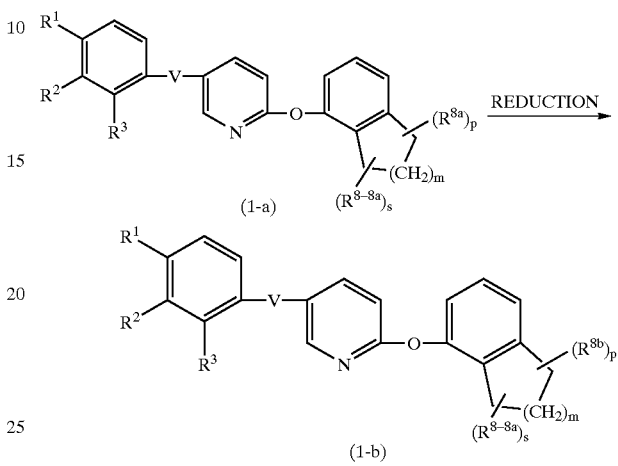

(wherein $R^1$, $R^2$, $R^3$, V, p and m are as defined above; $R^{8a}$ represents an oxo group; $R^{8-8a}$ represents a group wherein $R^{8a}$ is eliminated from $R^8$; s represents 0 or 1, with the proviso that s represents 0 when n is 2; and $R^{8b}$ represents a hydroxyl group)

In the above reaction scheme, the case where A is a group $A^2$ was illustrated, but the case where A is a group $A^3$ can also be carried out in the same manner. Also in the following reaction scheme, the case where A is a group $A^2$ was described, but the compound wherein A is a group $A^3$ can also be synthesized by the corresponding reaction scheme.

The solvent may be any one which does not adversely affect the reaction, and examples thereof include ethers such as tetrahydrofuran (THF), dioxane and diethyl ether; halogenated hydrocarbon such as methylene chloride and chloroform; and aromatic hydrocarbon such as benzene and toluene.

The reduction process includes, for example, a catalytic reduction process in a suitable solvent, or a process using a reducing agent such as lithium aluminum hydride, sodium borohydride, lithium borohydride, diborane and raney nickel.

The reducing agent is usually used in the amount of 0.25 to 5 mol, and preferably from 1 to 3 mol, per mol of the pyridine derivative (1-a) in the case of one oxo group ($R^{8a}$). In the case of two oxo groups ($R^{8a}$), the reducing agent is usually used in the amount of 2 to 10 mol, and preferably from 2 to 6 mol. The reaction is usually carried out at 0 to 30° C. and is completed within about 1 to 30 hours.

In the pyridine derivative (1) of the present invention, even if $R^8$ in the group $A^2$ or $R^9$ in the group $A^3$ of A is a group: =N—$OR^{10}$ ($R^{10}$ represents a hydrogen atom, a lower alkyl group or a lower alkanoyl group), it may also be produced by using, as a starting material, a pyridine derivative (1-a) or (1-a') wherein $R^8$ or $R^9$ is an oxo group.

The process for producing pyridine derivatives (1-f-1) to (1-f-3) wherein $R^{10}$ in the group: =N—$OR^{10}$ is a hydrogen group, a lower alkyl group or a lower alkanoyl group will be explained in order by way of $R^8$ in the group $A^2$ as the example.

First, a pyridine derivative (1-f-1) wherein $R^8$ is a group: =N—OH ($R^{10}$ is a:hydrogen atom) is obtained by reacting the pyridine derivative (1-a) with hydroxylamine hydrochloride in a suitable solvent in the presence of a base, as shown in the following reaction scheme.

Reaction Scheme (III-b):

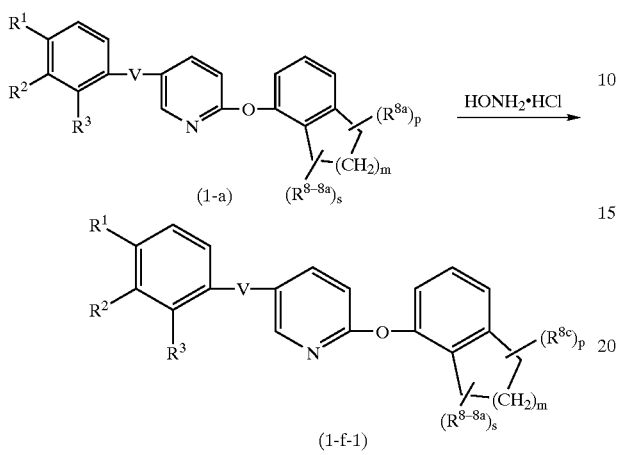

(wherein $R^1$, $R^2$, $R^3$, V, $R^{8a}$, $R^{8-8a}$, p, m and s are as defined above, and $R^8$ represents a group: =N—OH)

The solvent may be any one which does not adversely affect the reaction, and examples thereof include ethers such as tetrahydrofuran (THF), dioxane and diethyl ether; lower alcohols such as methanol, ethanol and isopropanol; and acetic acid and water.

The base includes, for example, trialkylamine such as triethylamine; alkali metal carbonate such as potassium carbonate, barium carbonate and sodium carbonate; alkali metal hydroxide such as sodium hydroxide and potassium hydroxide; and pyridine, 1,4-diazabicyclo[2.2.2]octane (DABCO), sodium acetate and piperidine. The amount of the base used is from 1 to 100 mol, and preferably from 2 to 10 mol, per mol of the pyridine derivative (1-a).

The amount of hydroxylamine hydrochloride used is from 1 to 50 mol, and preferably from 2 to 10 mol, per mol of the pyridine derivative (1-a). The reaction is usually carried out at −20 to 150° C., and is completed within about 5 minutes to 24 hours.

Then, a pyridine derivative (1-f-2) wherein $R^8$ is a group: =N—OR$^{10a}$ ($R^{10a}$ represents a lower alkyl group) can be produced by reacting according to the same manner as that described in the reaction scheme (III-b) except for using O-alkylhydroxylamine hydrochloride in place of the above hydroxylamine hydrochloride.

For example, in the pyridine derivative (1-f-2), a pyridine derivative (1-f-21) wherein $R^{10}$ is a methyl group can be produced by reacting according to the same manner as that described above except for using O-methylhydroxylamine hydrochloride in place of the above hydroxylamine hydrochloride.

A pyridine derivative (1-f-3) wherein $R^8$ is a group: =N—OR$^{10b}$ ($R^{10b}$ represents a lower alkanoyl group) is obtained by reacting the pyridine derivative (1-f-1), obtained from the pyridine derivative (1-a) wherein $R^8$ is an oxo group according to the process described in the above reaction scheme (III-b), with an acylating agent in a suitable solvent as shown in the following reaction scheme (III-c). In that case, when tertiary amine is added, basicity of the pyridine derivative (1-f-1) is enhanced and, therefore, the reaction proceeds.

Reaction Scheme (III-c):

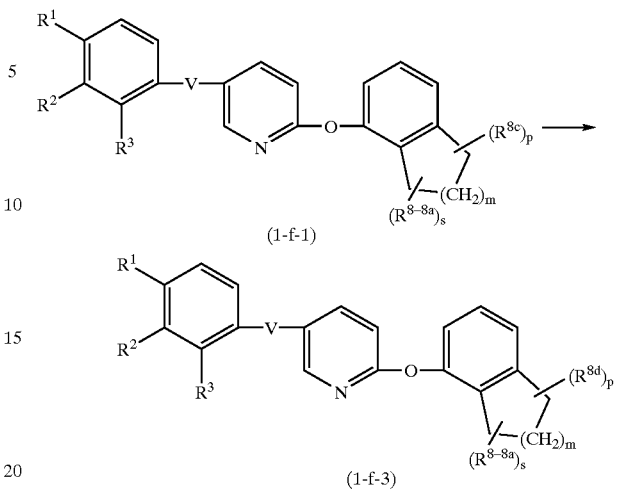

(wherein $R^1$ $R^2$ $R^3$, V, $R^{8c}$, $R^{8-8a}$, p, m and s are as defined above, and $R^{8d}$ represents a group: =N—OR$^{10b}$ ($R^{10b}$ is as defined above).

The solvent may be any one which does not adversely affect the reaction, and examples thereof include ethers such as tetrahydrofuran (THF), dioxane and diethyl ether; halogenated hydrocarbon such as methylene chloride and chloroform; and aromatic hydrocarbon such as benzene and toluene; and dimethylformamide.

The acylating agent includes acid anhydride or acid halide corresponding to the lower alkanoyl group as for $R^{10b}$, and examples thereof include acetic anhydride, acetyl halide, propionyl halide, isobutyryl halide, pivaloyl halide and hexanoyl halide.

Specifically explaining, acetic anhydride and acetyl halide (e.g. acetyl chloride, acetyl fluoride, acetyl iodide, acetyl bromide, etc.) may be used as the acylating agent to obtain a pyridine derivative (1-f-31) wherein $R^{10b}$ is an acetyl group in the above pyridine derivative (1-f-3).

The tertiary amine includes, for example, trialkylamine (e.g. triethylamine, etc.), pyridine, quinoline, lutidine, N-methylmorpholine, 4-dimethylaminopyridine and imidazole.

The amount of the acylating agent used is usually from 1 to 20 mol, and preferably from 1 to 5 mol, per mol of the pyridine derivative (1-f-1) in the case of one $R^{8c}$. The amount of the acylating agent used is usually from 2 to 40 mol, and preferably from 2 to 10 mol, per mol of the pyridine derivative (1-f-1) in the case of two $R^{8c}$. The reaction is usually carried out at −20 to 150° C., and is completed within about 5 minutes to 24 hours.

Pyridine derivatives (1-f'-1) to (1-f'-3) wherein $R^9$ in the group $A^3$ is a group: =N—OR$^{10}$ ($R^{10}$ is as defined above) is produced by reacting according to the same manner as that described in the above reaction schemes (III-b) and (III-c) except for using the pyridine derivative (1-a') in place of the pyridine derivative (1-a).

In the pyridine derivative (1) of the present invention, pyridine derivatives shown in the following items ③ to ④ may be produced by subjecting a pyridine (1-g) wherein Y in the group $A^2$ is a group: —(CH$_2$)$_m$— and at least one of $R^8$ is a hydroxyl group or a pyridine (1-g') wherein Y in the group $A^3$ is a group: —(CH$_2$)$_m$— and at least one of $R^9$ is a hydroxyl group as a starting material to the dehydration reaction in a suitable solvent.

③ a pyridine derivative (1-c) wherein Y in the group $A^2$ in A is a group: =CH(CH$_2$)$_m$— or a group: —(CH$_2$)$_{m-1}$CH= and at least one of $R^8$ is a hydrogen atom ④ a pyridine derivative (1-c') wherein Z in the group $A^3$ in A is a group: =CH(CH$_2$)$_{n-1}$— or a group: —(CH$_{2n-1}$)CH= and at least one of $R^9$ is a hydrogen atom The process for synthesizing the above pyridine derivative (1-c) of the item ③ will be explained by way of example.

Reaction Scheme (IV-a):

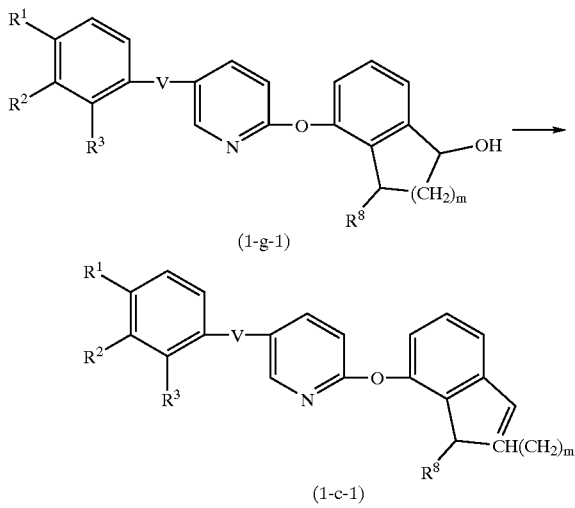

(wherein $R^1$, $R^2$, $R^3$, $R^8$, V and m are as defined above)

According to this reaction, a pyridine derivative (1-c-1) wherein Y is a group: —(CH$_2$)$_{m-1}$CH= is obtained by dehydrating a pyridine derivative (1-g-1) having a hydroxyl group in a suitable solvent, using a reaction reagent such as pyridinium bromide perbromide, dioxane dibromide, bromine, etc.

The solvent may be any one which does not adversely affect the reaction, and examples thereof include ethers such as tetrahydrofuran (THF), dioxane and diethyl ether; halogenated hydrocarbon such as methylene chloride, chloroform and carbon tetrachloride; aromatic hydrocarbon such as benzene and toluene; and acetic acid, trifluoroacetic acid and methanesulfonic acid.

The amount of pyridinium bromide perbromide used is usually from 1 to 5 mol, and preferably from 1 to 3 mol, per mol of the pyridine derivative (1-g-1). The reaction is usually carried out at −10 to 150° C., and is completed within about 30 minutes to 24 hours.

A pyridine derivative (1-c-2) wherein Y is a group: =CH(CH$_2$)$_{m-1}$— in the pyridine derivative (1-c) of the above item ① can be produced by reacting according to the same manner as that described in the reaction scheme (IV-a) except for using a pyridine derivative (1-g-2) represented by the general formula:

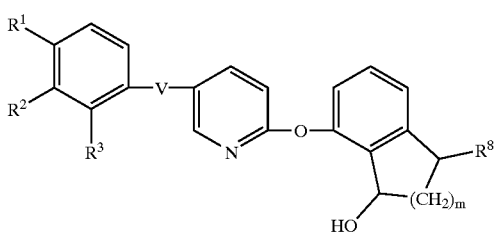

(wherein $R^1$, $R^2$, $R^3$, $R^8$, V and m are as defined above) in place of the above pyridine derivative (1-g-1).

In the pyridine derivative (1) of the present invention, pyridine derivatives (1-d) to (1-e) and (1-d') to (1-e') shown in the following items ⑤ to ⑧ may be produced by using, as a starting material, a pyridine derivative (1-h) wherein Y in the group $A^2$ is a group: —(CH$_2$)$_{m-1}$— and at least one of $R^8$ is an oxo group or a pyridine derivative (1-h') wherein Z in the group $A^3$ is a group: —(CH$_2$)$_n$— and at least one of $R^9$ is an oxo group.

⑤ a pyridine derivative (1-d) wherein Y in the group A is a group: =CH(CH$_2$)$_{m-1}$— or a group: —(CH$_2$)$_{m-1}$CH= and at least one of $R^8$ is a lower alkanoyloxy group ⑥ a pyridine derivative (1-d') wherein Z in the group $A^3$ is a group: =CH(CH$_2$)$_{n-1}$— or a group: —(CH$_2$)$_{n-1}$CH= and at least one of $R^8$ is a lower alkanoyloxy group ⑦ a pyridine derivative (1-e) wherein Y in the group $A^2$ is a group: =CH(CH$_2$)$_{m-1}$— or a group: —(CH$_2$)$_{m-1}$CH= and at least one of $R^8$ is a lower alkoxy group ⑧ a pyridine derivative (1-e') wherein Z in the group $A^3$ is a group: =CH(CH$_2$)$_{n-1}$— or a group: —(CH$_2$)$_{n-1}$CH= and at least one of $R^9$ is a lower alkoxy group The process for producing the pyridine derivatives (1-d) to (1-e) of the above items ⑤ and ⑦ will be explained by way of $R^8$ in the group $A^2$ as the example.

First, the process for producing the pyridine derivative (1-d) of the item ⑤ will be explained by using the following reaction scheme (IV-b).

Reaction Scheme (IV-b):

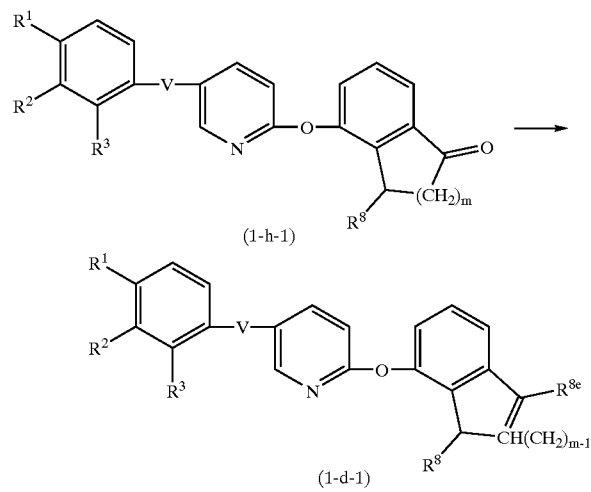

(wherein $R^1$, $R^2{}_1$, $R^3$, $R^8$, V and m are as defined above, and $R^{8e}$ represents a lower alkanoyloxy group)

According to this reaction, a pyridine derivative (1-d-1) wherein Y is a group: —(CH$_2$)$_{m-1}$CH= and has a lower alkanoyloxy group is obtained by reacting a pyridine derivative (1-h-1) having an oxo group with an acylating agent in a state free from solvent or in a suitable solvent in the presence of an acid or a base.

The solvent may be any one which does not adversely affect the reaction, and examples thereof include ethers such as tetrahydrofuran (THF), dioxane and diethyl ether; halogenated hydrocarbon such as methylene chloride and chloroform; aromatic hydrocarbon such as benzene and toluene; and dimethylformamide and acetic acid.

The acylating agent includes acid anhydride, acid halide or esters (e.g. isopropenyl ester, etc.) corresponding to the alkanoyl moiety of $R^{8e}$ and examples thereof include acetic anhydride, acetyl halide, isopropenyl acetate, propionyl halide, isopropenyl propionate, isobutyryl halide, pivaloyl halide and hexanoyl halide.

Specifically explaining, acetic anhydride, isopropyl acetate and acetyl halide (e.g. acetyl chloride, acetyl fluoride, acetyl iodide, acetyl bromide, etc.) may be used as the acylating agent to obtain a pyridine derivative (1-d-11) wherein $R^{8e}$ is an acetyloxy group in the above pyridine derivative (1-d-1).

The acid includes, for example, Lewis acid such as boron trifluoride, boron trichloride, stannic chloride, titanium tetrachloride, boron trifluoride-ethyl ether complex and zinc chloride; hydrogen halide such as hydrogen chloride, hydrogen bromide, hydrogen fluoride and hydrogen iodide; inorganic acid such as hydrochloric acid, hydrobromic acid, nitric acid, perchloric acid and sulfuric acid; organic acid such as trichloroacetic acid, trifluoroacetic acid and p-toluenesulfonic acid; and anion exchange resin.

The base includes, for example, trialkylamine (e.g. triethylamine, etc.), pyridine, dimethylaminopyridine, lithium diisoproylamide (LDA), potassium hydride, sodium hydride, sodium methoxide, potassium acetate, sodium acetate and cation exchange resin.

The amount of the acylating agent used is usually from 1 to 100 mol, and preferably from 2 to 5 mol, per mol of the pyridine derivative (1-h-1). The amount of the acid or base used is usually from 0.01 to 10 mol, and preferably from 0.02 to 0.1 mol, per mol of the pyridine derivative (1-h-1). The reaction is usually carried out under the conditions of −78 to 150° C. for 1 minute to 3 days, and preferably about 15 minutes to 24 hours.

A pyridine derivative (1-d-2) wherein Y is a group: =CH(CH$_2$)$_{m-1}$— in the pyridine derivative (1-d) of the above item ⑤ can be produced by reacting according to the same manner as that described in the reaction scheme (IV-b) except for using a pyridine derivative represented by the general formula (1-h-2):

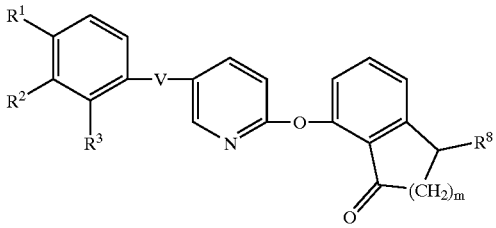

(1-h-2)

(wherein $R^1$, $R^2$, $R^3$, $R^8$, V and m are as defined above) in place of the above pyridine derivative (1-h-1).

The pyridine derivative (1-d') of the above item ⑥ can be produced by reacting according to the same manner as that described in the reaction scheme (IV-b) except for using a pyridine derivative (1-h') wherein at least one of $R^9$ is an oxo group in place of the pyridine derivative (1-h-1).

The process for producing the pyridine derivative (1-e) of the above item ⑦ will be explained below by using the following reaction scheme (IV-c).

Reaction Scheme (IV-c):

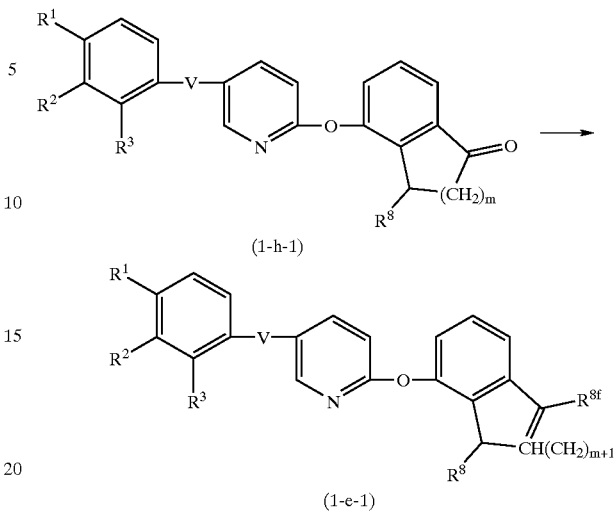

(wherein $R^1$, $R^2$, $R^3$, $R^8$, V and m are as defined above, and $R^{8f}$ represents a lower alkoxy group)

According to this reaction, a pyridine derivative (1-e-1) having a lower alkoxy group is obtained by reacting the pyridine derivative (1-h-1) with an orthoformic acid lower alkyl ester in a suitable solvent in the presence of an acid. In that case, when anhydrous magnesium sulfate or 4A molecular sieve is added, water is easily removed from the reaction system and, therefore, the reaction proceeds.

The solvent may be any one which does not adversely affect the reaction, and examples thereof include ethers such as tetrahydrofuran (THF), dioxane and diethyl ether; lower alcohols such as methanol and ethanol; halogenated hydrocarbon such as methylene chloride and chloroform; aromatic hydrocarbon such as benzene and toluene; and nitromethane.

The acid includes, for example, Lewis acid (e.g. boron trifluoride, boron trichloride, stannic chloride, titanium tetrachloride, boron trifluoride-ethyl ether complex and zinc chloride, etc.), p-toluenesulfonic acid, trichloroacetic acid, trifluoroacetic acid, methanesulfonic acid, acetic acid and (±)-10-camphorsulfonic acid.

The lower alkyl orthoformate includes, for example, alkyl orthoformate whose alkyl moiety has 1 to 6 carbon atoms, such as methyl orthoformate, ethyl orthoformate, butyl orthoformate and hexyl orthoformate. Specifically explaining, ethyl orthoformate may be used as the lower alkyl orthoformate in the case of obtaining a pyridine derivative (1-e-11) wherein $R^{8f}$ is an ethoxy group in the above pyridine derivative (1-e-1).

The amount of the lower alkyl orthoformate used is usually from 1 to 100 mol, and preferably from 5 to 20 mol, per mol of the pyridine derivative (1-h-1).

The amount of the acid used is usually from 0.01 to 2 mol, and preferably from 0.1 to 1.5 mol, per mol of the pyridine derivative (1-h-1). The reaction is usually carried out at −78 to 150° C., and is completed within about 1 minute to 24 hours.

A pyridine derivative (1-e-2) wherein Y is a group: =CH(CH$_2$)$_{m-1}$— in the pyridine derivative (1-e) of the above item ⑦ can be produced by reacting according to the same manner as that described in the reaction scheme (IV-c) except for using a pyridine derivative (1-h-2) in place of the above pyridine derivative (1-h-1).

The above pyridine derivative (1-e') of the item ⑧ can be produced by reacting according to the same manner as that described in the reaction scheme (IV-c) except for using a pyridine derivative (1-h') wherein at least one of $R^9$ is an oxo group in place of the pyridine derivative (1-h-1).

Reaction Scheme (V):

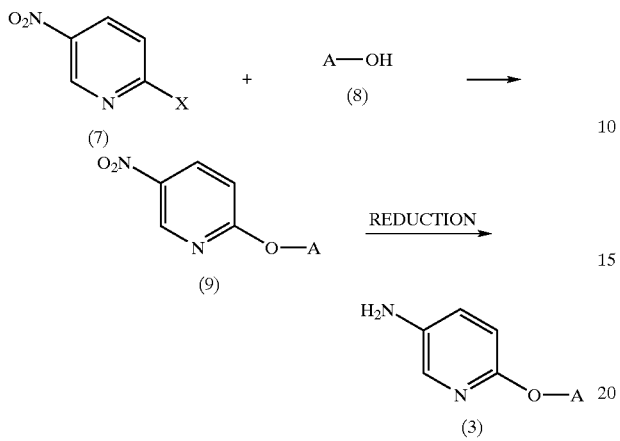

(wherein A and V are as defined above)

According to this reaction, the above compound (3) as a starting material of the reaction scheme (I-a) or reaction scheme (I-b) is obtained by reacting a monohalogenonitropyrodine (7) with a compound (8) to give a 3-nitropyridine derivative (9) and reducing this 3-nitropyridine derivative (9) in a suitable solvent using a catalytic reduction process, or reducing in the presence of an acid using a catalyst such as zinc, iron and tin.

The reaction for obtaining the 3-nitropyridine derivative (9) from the monohalogenonitropyridine derivative (7) and compound (8) is carried out in a state free from solvent, or in a suitable solvent. In that case, potassium carbonate or sodium carbonate may also be added to enhance nucleophilic property of the compound (8).

The solvent may be any one which does not adversely affect the reaction, and examples thereof include lower alcohols such as methanol, ethanol and isopropanol; ethers such as diethyl ether, tetrahydrofuran and dioxane; halogenated hydrocarbon such as methylene chloride and chloroform; and dimethylformamide and dimethyl sulfoxide.

The amount of the compound (8) used is usually 1 mol, and preferably from 1 to 5 mol, per mol of the monohalogenonitropyridine derivative (7).

The reaction is usually carried out at 0 to 150° C., and preferably from 20 to 80° C., and the reaction is completed within about 1 to 30 hours.

The reaction for obtaining a compound (3) from a 3-nitropyridine derivative (9) is carried out in a state free from solvent, or in a suitable solvent.

The solvent may be any one which does not adversely affect the reaction, and examples thereof include lower alcohols such as methanol, ethanol and isopropanol; ethers such as diethyl ether, tetrahydrofuran and dioxane; and dimethoxymethane, dimethoxyethane and water.

The amount of the reducing agent used is usually from 0.05 to 5 mol, and preferably from 0.2 to 3 mol, per mol of the 3-nitropyridine derivative (9).

The reaction is usually carried out at −10 to 150° C., and preferably from 0 to 50° C., and the reaction is completed within about 30 minutes to 30 hours.

An aminopyridine derivative (3-b) wherein $R^4$ or $R^5$ in the group A in A is a 2-lower alkyl-1,3-dioxolane group is synthesized by the following reaction scheme (VI).

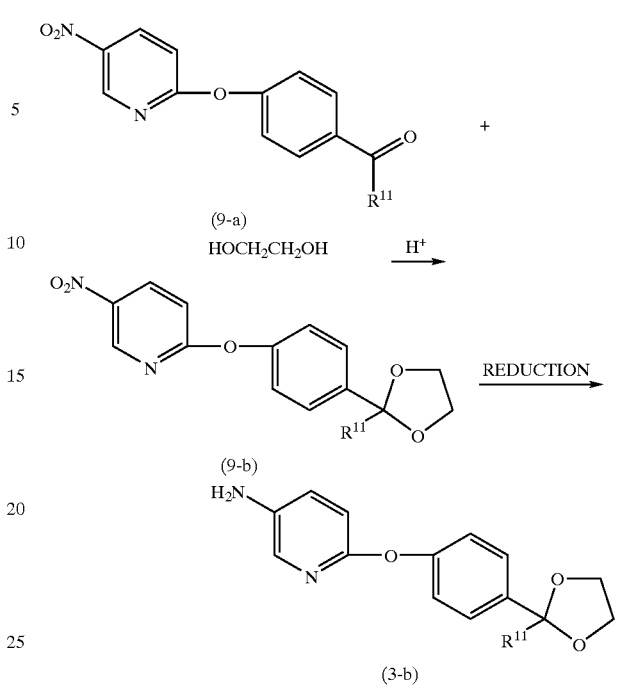

(wherein $R^{11}$ represents a lower alkyl group)

That is, the above aminopyridine derivative (3-b) is obtained by reacting a nitro compound (9-a) with ethylene glycol in a suitable solvent in the presence of an acid to give a cyclic acetal (dioxolane) compound (9-b) and reducing this compound (9-b) according to the same manner as that described in the reaction scheme (V).

The solvent may be any one which does not adversely affect the reaction, and examples thereof include lower alcohols such as methanol, ethanol and isopropanol; ethers such as diethyl ether, tetrahydrofuran and dioxane; aromatic hydrocarbon such as benzene and toluene; and dimethoxyethane.

As the acid, for example, p-toluenesulfonic acid, trichloroacetic acid, trifluoroacetic acid, methanesulfonic acid, acetic acid and (±)-10-camphorsulfonic acid are preferably used. Among them, (±)-10-camphorsulfonic acid is preferably used.

The amount of ethylene glycol used is usually 1 mol, and preferably from 1 to 5 mol, per mol of the nitro compound (9-a).

The amount of the acid used is usually from 0.01 to 0.1 mol, and preferably from 0.01 to 0.05 mol, per mol of the nitro compound (9-a).

The reaction is usually carried out at −10 to 150° C., and preferably from room temperature to 100° C., and the reaction is completed within about 1 to 30 hours.

In the present invention, the pyridine derivative (1) wherein $R^4$ or $R^5$ in the group $A^1$ in A is a 2-lower alkyl-1,3-dioxolane group of the present invention may be produced by using the aminopyridine derivative (3-b) obtained in the above reaction scheme (VI) as a starting material, or may also be produced by synthesizing a pyridine derivative wherein $R^4$ or $R^5$ in the group $A^1$ in A is a lower alkanoyl group (with the proviso that a formyl group is eliminated) and converting said oxo group into a cyclic acetal according to the process described in the above reaction scheme (VI).

The pyridine derivative wherein $R^8$ in the group $A^2$ in A or $R^9$ in the group $A^3$ is a group:

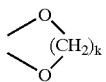

(wherein k is as defined above) can also be produced according to the same manner as that in case of $R^4$ or $R^5$ in the above group $A^1$.

In the above 3-aminopyridine derivative (3), 3-aminopyridine derivatives (3-d) to (3-d') shown in the following items (i) to (ii) may also be produced by using, as a starting material, a 3-nitropyridine derivative (9-c) wherein Y in the group $A^2$ is a group: —$(CH_2)_m$— and at least one of $R^8$ is an oxo group or a 3-nitropyridine derivative (9-c') wherein Z in the group $A^3$ is a group: —$(CH_2)_n$— and at least one of $R^9$ is an oxo group.

(i) a 3-aminopyridine derivative (3-d) wherein Y in the group $A^2$ in A is a group: =$CH(CH_2)_{m-1}$— or a group: —$(CH_2)_{m-1}CH$= and $R^8$ is a lower alkanoyloxy group (ii) a 3-aminopyridine derivative (3-d') wherein Z in the group $A^3$ in A is a group: =$CH(CH_2)_{n-1}$— or a group: —$(CH_2)_{n-1}CH$= and $R^9$ is a lower alkanoyloxy group The process: for producing 3-aminopyridine (3-d-1) wherein Y in the group $A^2$ is a group: —$(CH_2)_{m-1}CH$= of the above item (i) will be explained by way of example. Reaction Scheme (VII-a):

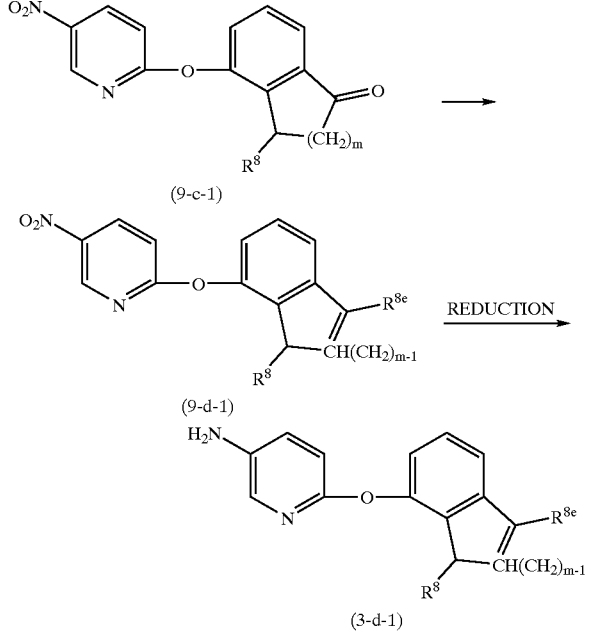

(wherein $R^8$, m and $R^{8e}$ are as defined above)

That is, as shown in the above reaction scheme (VII-a), the 3-aminopyridine derivative (3-d-1) is obtained by reacting the 3-nitropyridine derivative (9-c-1) with an acylating agent to give a 3-nitropyridine derivative represented by the general formula (9-d-1) and reducing this compound (9-d-1) using a catalytic reduction process.

The reaction for obtaining the compound (9-d-1) from the 3-nitropyridine derivative (9-c-1) is carried out in a state free from solvent or in a suitable solvent in the presence of an acid or a base.

The solvent may be any one which does not adversely affect the reaction, and examples thereof include ethers such as tetrahydrofuran (THF), dioxane and diethyl ether; halogenated hydrocarbon such as methylene chloride and chloroform; aromatic hydrocarbon such as benzene and toluene; and dimethylformamide and acetic acid.

As the acylating agent, for example, acid anhydride, acid halide or esters (e.g. isopropenyl ester, etc.) corresponding to the alkanoyl moiety of $R^{8e}$ may be used. Specifically explaining, since the lower alkanoyl moiety of $R^{8e}$ is acetyl when obtaining a compound (3-d-11) wherein $R^{8e}$ is an acetyloxy group, for example, acetic anhydride, acetyl chloride and isopropenyl acetate may be used as the acylating agent (acetylating agent in this case).

The acid includes, for example, Lewis acid such as boron trifluoride, boron trichloride, stannic chloride, titanium tetrachloride, boron trifluoride-ethyl ether complex and zinc chloride; hydrogen halide such as hydrogen chloride, hydrogen bromide and hydrogen iodide; inorganic acid such as hydrochloric acid, hydrobromic acid, nitric acid, perchloric acid and sulfuric acid; organic acid such as trichloroacetic acid, trifluoroacetic acid and p-toluenesulfonic acid; and anion exchange resin., The base includes, for example, trialkylamine (e.g. triethylamine, etc.), pyridine, dimethylaminopyridine, lithium diisoproylamide (LDA), potassium hydride, sodium hydride, sodium methoxide, potassium acetate, sodium acetate and cation exchange resin.

The amount of the acylating agent used is usually from 1 to 100 mol, and preferably from 2 to 5 mol, per mol of the 3-nitropyridine derivative (9-c-1). The amount of the acid or base used is usually from 0.01 to 10 mol, and preferably from 0.02 to 0.1 mol, per mol of the 3-nitropyridine derivative (9-c-1).

The reaction is usually carried out under the conditions of −78 to 150° C. for 1 minute to 3 days, and preferably about 15 minutes to 24 hours.

The reaction for obtaining the compound (3-d-1) from the compound (9-d-1) is carried out in a suitable solvent. The solvent may be any one which does not adversely affect the reaction, and examples thereof include ethers such as tetrahydrofuran (THF) and dioxane; and dimethoxyethane, diethoxyethane and water.

As the reducing agent used in the reduction includes, for example, platinum dioxide, palladium-carbon (Pd—C) and Raney nickel. Among them, platinum dioxide is superior in selective reduction.

The amount of the reducing agent used is usually from 0.01 to 5 mol, and preferably from 0.02 to 0.1 mol, per mol of the 3-nitropyridine derivative (9-d-1).

The reaction is usually carried out at −10 to 150° C., and preferably from 0 to 50° C., and the reaction is completed within about 10 minutes to 30 hours.

A pyridine derivative (3-d-2) wherein Y is a group: =$CH(CH_2)_{m-1}$ in the 3-aminopyridine derivative (3-d) of the above item (i) can be produced by reacting according to the same manner as that described in the reaction scheme (VII-a) except for using a 3-nitropyridine derivative represented by the general formula (9-c-2):

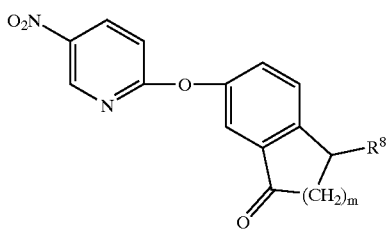

(9-c-2)

(wherein $R^8$ and m are as defined above) in place of the above 3-nitropyridine derivative (9-c-1).

The 3-aminopyridine derivative (3-d') of the above item (ii) can be produced by reacting according to the same manner as that described in the reaction scheme (VII-a) except for using a 3-nitropyridine derivative (9-c') in place of the 3-nitropyridine derivative (9-c-1).

In the 3-aminopyridine derivative (3), 3-aminopyrdine derivatives (3-e) to (3-e') shown in the following items (iii) to (iv) may also be produced by using, as a starting material, a 3-nitropyridine derivative wherein at least one of $R^8$ is an acetyloxy group, such as compound (9-d-11) obtained by the above reaction scheme (VII-a), or 3-nitropyridine derivatives (9-d'-11) to (9-d'-21) wherein at least one of $R^8$ is an acetyloxy group.

(iii) a 3-aminopyridine derivative (3-e) wherein Y in the group $A^2$ in A is a group: $=CH(CH_2)_{m-1}-$ or a group: $-(CH_2)_{m-1}CH=$ and at least one of $R^8$ is an aroyloxy group or a lower alkanoyloxy group except acetoxy group (iv) a 3-aminopyridine derivative (3-e') wherein Z in the group $A^3$ in A is a group: $=CH(CH_2)_{n-1}-$ or a group: $-(CH_2)_{n-1}CH=$ and at least one of $R^9$ is an aroyloxy group or a lower alkanoyloxy group except acetoxy group The process for producing 3-aminopyridine (3-e-1) wherein Y in the group $A^2$ is a group: $-(CH_2)_{m-1}CH=$ of the above item (iii) will be explained by using the following reaction scheme (VII-b).

Reaction Scheme (VII-b):

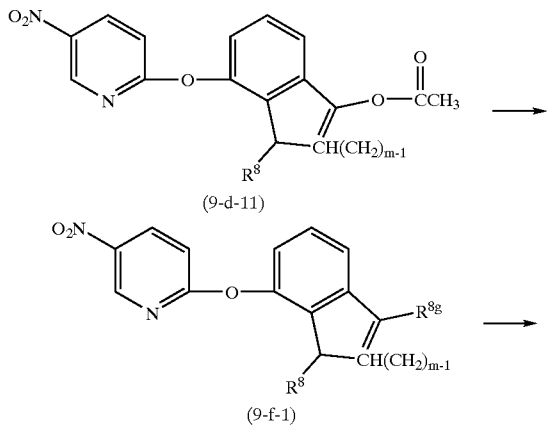

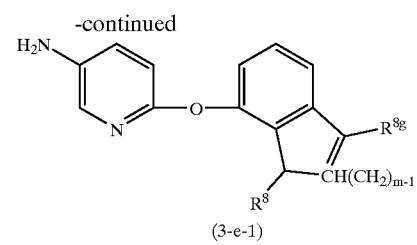

(3-e-1)

(wherein $R^8$ and m are as defined above, and $R^{8g}$ represents an aroyloxy group or a lower alkanoyloxy group except acetoxy group)

According to this reaction, the above 3-aminopyridine derivative (3-e-1) is obtained by reacting a compound (9-d-11) obtained in the reaction scheme (VII-a) with an acid halide in a state free from solvent or in a suitable solvent in the presence of an acid to give a compound represented by the general formula (9-f-1) and reducing this compound (9-f-1) using a catalytic reduction process according to the same manner as that in case of the reaction scheme (VII-a).

The solvent may be any one which does not adversely affect the reaction, and examples thereof include ethers such as tetrahydrofuran (THF), dioxane and diethyl ether; halogenated hydrocarbon such as carbon tetrachloride, methylene chloride and chloroform; and aromatic hydrocarbon such as benzene and toluene.

As the acid halide, for example, acid halide corresponding to the acyl moiety of $R^{8g}$ may be used, and examples thereof include propionyl halide, isobutyryl halide, pivaloyl halide, hexanoyl halide and benzoyl halide. Specifically explaining, benzoyl halide such as benzoyl chloride, benzoyl bromide, benzoyl iodide and benzoyl fluoride may be used when obtaining a compound (3-e-11) wherein the acyl moiety of the acyloxy group is benzoyl.

The acid includes, for example, Lewis acid such as boron trifluoride, boron trichloride, stannic chloride, titanium tetrachloride, boron trifluoride-ethyl ether complex and zinc chloride; hydrogen halide such as hydrogen chloride, hydrogen bromide, hydrogen fluoride and hydrogen iodide; inorganic acid such as hydrochloric acid, hydrobromic acid, nitric acid, perchloric acid and sulfuric acid; organic acid such as trichloroacetic acid, trifluoroacetic acid and p-toluenesulfonic acid; and anion exchange resin.

The amount of the acid halide used is usually from 1 to 100 mol, and preferably from 5 to 10 mol, per mol of the 3-nitropyridine derivative (9-d-11). The amount of the acid or base used is usually from 0.01 to 10 mol, and preferably from 0.02 to 0.1 mol, per mol of the 3-nitropyridine derivative (9-d-11).

The reaction is usually carried out under the conditions of −78 to 150° C. for 1 minute to 3 days, and preferably about 15 minutes to 24 hours.

A pyridine derivative (3-e-2) wherein Y is a group: $=CH(CH_2)_{m-1}-$ in the 3-aminopyridine derivative (3-e) of the above item (iii) can be produced by reacting according to the same manner as that described in the reaction scheme (VII-b) except for using a pyridine derivative represented by the general formula (9-d-21):

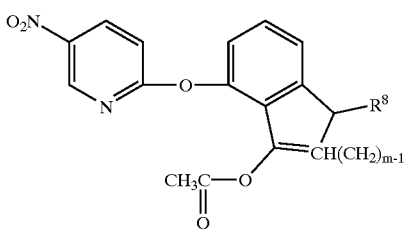

(9-d-21)

(wherein $R^8$ and m are as defined above) in place of the above pyridine (9-d-11).

The 3-aminopyridine derivative (3-e') of the above item (iv) can be produced by reacting according to the same manner as that described in the reaction scheme (VII-b) except for using a pyridine derivative (9-d'-11) or (9-d'-21) wherein Z is a group: $=CH(CH_2)_{n-1}-$ or a group: $-(CH_2)_{n-1}CH=$ and at least one of $R^9$ is an acetyloxy group in place of the above pyridine derivative (9-d-11) Reaction Scheme (VIII):

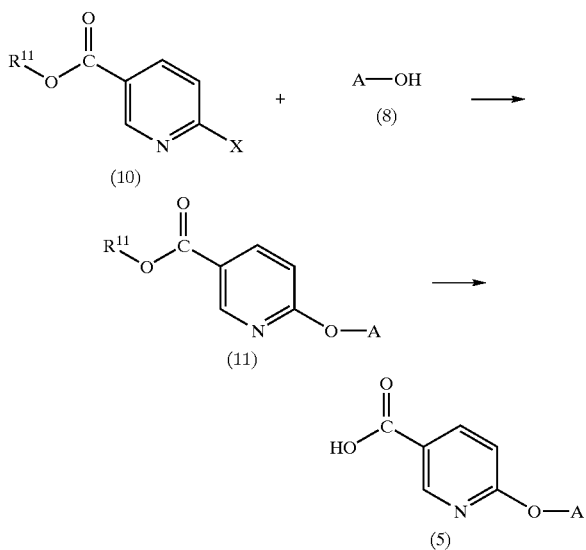

(wherein A, X and $R^{11}$ are as defined above)

According to this reaction, the above carboxylic acid (5) as a starting material of the reaction scheme (II) is obtained by reacting a monohalogenopyridinecarboxylate (10) with a compound (8) to give a pyridinecarboxylate derivative (11) and hydrolyzing a protective group in this compound (11).

To obtain the pyridinecarboxylate derivative (11) from the monohalogenopyridinecarboxylate (10), the reaction may be carried out according to the same manner as that described in the above reaction scheme (V).

The amount of the compound (8) used is usually 1 mol, and preferably from 1 to 5 mol, per mol of the monohalogenopyridinecarboxylate (10).

The reaction is usually carried out at 0 to 150° C., and preferably from 20 to 80° C., and the reaction is completed within 1 to 30 hours.

The pyridinecarboxylate derivative (11) is hydrolyzed in a suitable solvent in the presence of a basic compound.

The basic compound includes, for example, alkali metal hydroxide such as sodium hydroxide and potassium hydroxide; alkali metal carbonate such as sodium carbonate and potassium carbonate; alkali metal hydrogencarbonate such as sodium hydrogencarbonate and potassium hydrogencarbonate; trialkylamine such as triethylamine and tributylamine; and organic base such as pyridine, picoline and 1,4-diazabicyclo[2.2.2]octane.

The solvent may be any one which does not adversely affect the reaction, and examples thereof include lower alcohols such as methanol, ethanol and isopropanol; ethers such as diethyl ether, tetrahydrofuran (THF) and dioxane; water or a mixed solvent thereof.

This hydrolysis reaction is usually carried out at −10 to 200° C., and preferably from 30 to 60° C., and the reaction is completed within about 30 minutes to 24 hours.

Reaction Scheme (IX)

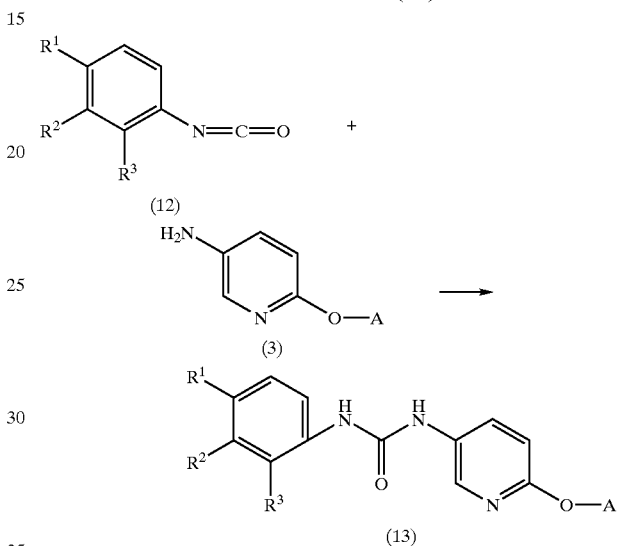

(wherein $R^1$, $R^2$, $R^3$ and A are as defined above)

This reaction is a process for obtaining a pyridine derivative (13) which is a compound wherein V is —NH—C(=O)—NH— in the general formula (1).

According to this reaction, the urea derivative (13) is obtained by the addition of 3-amino-pyridine derivative (3) to the isocyanato compound (12) in a state free from solvent or in an inert solvent: and amines may be added in the reaction system.

The solvents include, for example, benzene, toluene, chlorobenzene, dichloromethane, acetone or tetrahydrofuran and the like. The amines include, for example, tertiary amines such as triethylamine, triisopropylamine and pyridine. The amount of the amine used is usually from 1 to 5 mol, and preferably from 1 to 2 mol, per mol of the isocynato compound (12).

The 3-amino-pyridine derivative (3) used is usually from 1 to 10 mol, and preferably 1 to 3 mol, per mol of the isocyanato compound (12). The reaction is usually carried out under the conditions of —10 to 150° C., and is completed within 10 minutes to 24 hours.

Reaction Scheme (X):

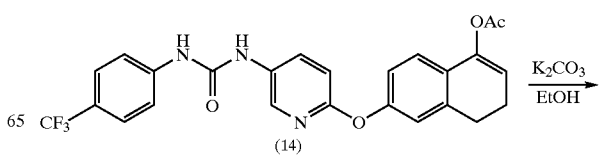

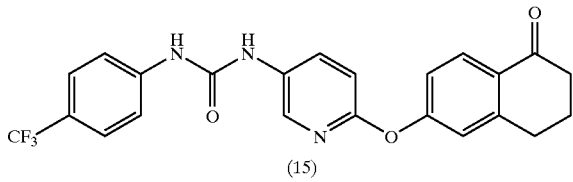

(15)

According to this reaction, a compound (15) is obtained by saponifying an enol ester derivative (14) using an alkali, and the reaction is carried out in a suitable solvent. The alkali includes, for example, hydroxide of alkali metal, salts, hydroxide of alkali earth metal, salts, and amines. The solvent may be a protonic solvent, and examples thereof include water; alcohols such as methanol and dioxane; and a mixed solvent of these solvents and ethers such as tetrahydrofuran and dioxane, acetonitrile and dimethylformamide. The amount of the alkali used is usually from 1 to 10 mol, and preferably from 1 to 3 mol, per mol of the compound (14). The reaction is usually carried out at −10 to 150° C., and is completed within about 30 minutes to 24 hours.

Reaction Scheme (XI):

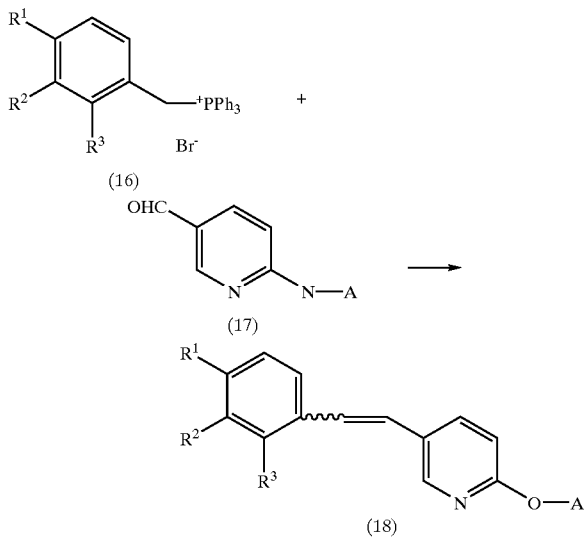

This reaction is a process for obtaining a pyridine derivative (18) which is a compound wherein V is —CH=CH— in the general formula (1).

According to this reaction, the pyridine derivative (18) is obtained by subjecting phosphorus-ylide generated from the compound (16) to condensation (Witting reaction) with the aldehyde compound (17).

The phosphorus-ylide is generated from the phosphonium salt (16) under anhydrous condition with a suitable combination of a base and a solvent.

The combination of a base and a solvent includes, for example, sodium ethoxide-ethanol, N,N-dimethylformamide; sodium methoxide-methanol-ether, N,N-dimethylformamide; potassium t-butoxide-tetrahydrofuran, dichloromethane; n-butyl lithium-ether; phenyl lithium-ether and the like. The base used is usually from 1 to 10 mol, and preferably 1 to 2 mol, per mol of the phosphonium salt (16). The reaction is usually carried out at −10 to 150° C., and is completed within 30 minutes to 24 hours. The phosphorus-ylide is reacted with the aldehyde compound (17) in a solvent mentioned above, and the compound (17) used is usually from 1 to 10 mol, and preferably 1 to 3 mol, per mol of the compound (16). The reaction is carried out at −10 to 150° C., and is completed within 30 minutes to 24 hours.

A salt of the pyridine derivative (1) in the present invention includes a pharmaceutically acceptable salt. Such a salt include, for example, inorganic acid salt such as hydrochloride, hydrobromide, nitrate, sulfate and phosphate; and organic acid salt such as methanesulfonate, p-toluenesulfonate, acetate, citrate, tartrate, maleate, fumarate, malate and lactate.

A pharmaceutical preparation containing the pyridine derivative (1) or a pharmaceutical acceptable salt thereof as an active ingredient will be explained below.

The pharmaceutical preparation is prepared in the form of a usual pharmaceutical preparation by using the pyridine derivative (1) of the present invention, and is usually prepared by using diluents and/or excipients, such as a fillers, extenders, binders, humectants, disintegrators, surfactants and lubricants, which are usually used.

The pharmaceutical preparation can be selected from various forms according to the purpose of treating, and typical examples thereof include tablets, pills, powders, solutions, suspensions, emulsions, granules, capsules, suppositories and injections (e.g. solution, suspension, etc.).

In the case of forming into tablets, conventionally known one can be widely used as a carrier. For example, there can be used excipients such as lactose, sucrose, sodium chloride, glucose, urea, starch, calcium carbonate, kaolin and crystalline cellulose; binders such as water, ethanol, propanol, simple syrup, glucose solution, starch solution, gelatin solution, carboxymethylcellulose, shellac, methylcellulose, potassium phosphate and polyvinyl pyrrolidone; disintegrators such as dried starch, sodium alginate, agar powder, laminarin powder, sodium hydrogencarbonate, calcium carbonate, polyoxyethylene sorbitan fatty esters, sodium lauryl sulfate, monoglyceride stearate, starch and lactose; disintegration inhibitors such as sucrose, stearin, cacao butter and hydrogenated oil; absorption accelerators such as quaternary ammonium base and sodium lauryl sulfate; humectants such as glycerin and starch; adsorbents such as starch, lactose, kaolin, bentonite and colloidal silicic acid; and lubricants such as purified talc, stearate, boron powder and polyethylene glycol. If necessary, tablets can be subjected to tablet coating to form sugar coated tablets, gelatin coated tablets, enteric coated tablets, film coated tablets, or two-layer tablets and multilayer tablets.

In the case of forming into pills, conventionally known one can be widely used as a carrier. For example, there can be used excipients such as glucose, lactose, starch, cacao butter, hardened vegetable oil, kaolin and talc; binders such as arabic gum powder, powdered tragacanth, gelatin and ethanol; and disintegrators such as laminarin and agar.

In the case of forming into suppositories, conventionally known one can be widely used as a carrier. For example, there can be used polyethylene glycol, cacao butter, higher alcohol, esters of higher alcohol, gelatin, semisynthetic and glyceride.

In the case of preparing injections, for example, solutions, emulsions and suspensions are preferably sterilized and are isotonic with blood. In the case of forming into the form of solutions, emulsions and suspensions, conventionally known one can used as a diluent. For example, there can be used water, ethanol, propylene glycol, ethoxylated isostearyl alcohol, polyoxylated isostearyl alcohol and polyoxyethylene sorbitan fatty esters. In this case, sodium chloride, glucose or glycerin may also be contained in the pharmaceutical preparation in the amount enough to prepare an isotonic solution. Furthermore, normal solubilizers, buffers and soothing agents may also be contained and, if necessary, colorants, preservatives, perfumes, flavors, sweeteners and other pharmaceuticals may also be contained.

The amount of the pyridine derivative (1) or a salt thereof to be contained in the pharmaceutical preparation can not be specifically limited and selected widely, but is preferably from 1 to 70% by weight based on the total composition.

The process for administration of the pharmaceutical preparation of the present invention is not specifically limited and the pharmaceutical preparation is administered according to the various preparation forms, age and sex of patients, conditions of diseases and other conditions. For example, tablets, pills, solutions, suspensions, emulsions, granules and capsules are orally administered.

Injections are administered intravenously as they are, or after combining with a normal replenisher such as glucose and amino acid. Furthermore, injections can be administered alone, intramuscularly, intracutaneously or subcutaneously, if necessary. Suppositories are administered intrarectally.

The dosage of the pharmaceutical preparation may be appropriately selected according to direction for use, age and sex of patients, conditions of diseases, and other conditions, and the pharmaceutical preparation is administered 1 to several times per day with a dairy dose ranging from 0.01 to 100 mg/kg, and preferably from 0.1 to 50 mg/kg.

As a matter of course, since the dosage varies depending upon various conditions, the dosage is sometimes sufficient when the dosage is smaller than the above range, or the dosage exceeding the above range is sometimes required.

BEST MODE FOR CARRYING OUT THE INVENTION

The following Reference Examples, Examples, Preparation Examples and Test Examples further illustrate the present invention in detail.

Reference Example 1

Synthesis of 4-[(5-nitro-2-pyridinyl)oxy]-1-indanone 1.0 g of 4-hydroxy-1-indanone, 1.07 g of 2-chloro-5-nitropyridine and 5 g of anhydrous potassium carbonate were dissolved in 10 ml of N,N-dimethylformamide (DMF) and the mixture was stirred at room temperature for 17 hours. After the completion of the reaction, 50 ml of water was added to the reaction solution and the solution was extracted with ethyl acetate. After the organic (ethyl acetate) layer was washed with water and dried over anhydrous sodium sulfate, the solvent was distilled off. The resulting residue was recrystallized from ethyl acetate to obtain the titled compound (1.36 g, pale yellow powder).

Melting point: 130–132° C.

Reference Example 2

Synthesis of 6-[(5-nitro-2-pyridinyl)oxy]-1-indanone

According to the same manner as that described in Reference Example 1 except for using an equimolar amount of 6-hydroxy-1-indanone in place of 4-hydroxy-1-indanone, the reaction was carried out to obtain the titled compound.

$^1$H-NMR (CDCl$_3$) δ ppm: 2.76–2.80 (m, 2H), 3.17–3.21 (m, 2H), 7.11 (d, 1H), 7.39 (dd, 1H), 7.53–7.58 (m, 2H), 8.48–8.53 (m, 1H), 9.01 (d, 1H)

Reference Example 3

Synthesis of 2,3-dihydro-1H-inden-5-yl(5-nitro-2-pyridinyl)ether

According to the same manner as that described in Reference Example 1 except for using an equimolar amount of 5-indanol in place of 4-hydroxy-1-indanone, the reaction was carried out to obtain the titled compound.

$^1$H-NMR (CDCl$_3$) δ: 2.1 (m, 2H), 2.9 (m, 4H), 6.8–9.0 (m, 6H)

Reference Example 4

Synthesis of 5-[(5-nitro-2-pyridinyl)oxy]-3,4-dihydro-1(2H)-naphthalenone

According to the same manner as that described in Reference Example 1 except for using an equimolar amount of 5-phydroxy-3,4-dihydro-1(2H)-naphthalenone in place of 4-hydroxy-1-indanone, the reaction was carried out to obtain the titled compound.

$^1$H-NMR (CDCl$_3$) δ ppm: 2.05–2.15 (m, 2H), 2.65–2.69 (m, 2H), 2.74–2.79 (m, 2H), 7.12 (d, 1H), 7.30 (dd, 1H), 7.42 (t, 1H), 8.04 (d, 1H), 8.52 (dd, 1H), 9.01 (d, 1H)

Reference Example 5

Synthesis of 3-[(5-nitro-2-pyridinyl)oxy]-6,7,8,9-tetrahydro-5H-benzo[a]cyclohepten-5-one According to the same manner as that described in Reference Example 1 except for using an equimolar amount of 3-hydroxy-6,7,8,9-tetrahydro-5H-benzo(a)cyclohepten-5-one in place of 4-hydroxy-1-indanone, the reaction was carried out to obtain the titled compound.

$^1$H-NMR (CDCl$_3$) δ ppm: 1.85–1.95 (m, 4H), 2.76–2.80 (m, 2H), 2.96–3.01 (m, 2H), 7.06 (d, 1H), 7.23 (dd, 1H), 7.31 (d, 1H), 7.54 (d, 1H), 8.49 (dd, 1H), 9.03 (d, 1H)

Reference Example 6

Synthesis of 1-{3-[(5-nitro-2-pyridinyl)oxy]phenyl}-1-ethanone

According to the same manner as that described in Reference Example 1 except for using an equimolar amount of 1-(3-hydroxyphenyl)-1-ethanone in place of 4-hydroxy-1-indanone, the reaction was carried out to obtain the titled compound.

$^1$H-NMR (CDCl$_3$) δ ppm: 2.63 (s, 3H), 7.11 (d, 1H), 7.36–7.41 (m, 1H), 7.57 (t, 1H), 7.76 (m, 1H), 7.87–7.90 (m, 1H), 8.52 (dd, 1H), 9.02 (d, 1H)

Reference Example 7

Synthesis of 1-{2-[(5-nitro-2-pyridinyl)oxy]phenyl}-1-ethanone

According to the same manner as that described in Reference Example 1 except for using an equimolar amount of 1-(2-hydroxyphenyl)-1-ethanone in place of 4-hydroxy-1-indanone, the reaction was carried out to obtain the titled compound.

$^1$H-NMR (CDCl$_3$) δ ppm: 2.6 (s, 3H), 7.0–9.0 (m, 7H)

Reference Example 8

Synthesis of 1-{4-[(5-nitro-2-pyridinyl)oxy]phenyl}-1-ethanone

According to the same manner as that described in Reference Example 1 except for using an equimolar amount of 1-(4-hydroxyphenyl)-1-ethanone in place of 4-hydroxy-1-indanone, the reaction was carried out to obtain the titled compound.

$^1$H-NMR (CDCl$_3$) δ ppm: 2.6 (s, 3H), 7.1–9.0 (m, 7H)

Reference Example 9

Synthesis of {4-[(5-nitro-2-pyridinyl)oxy]phenyl}(phenyl)methanone

According to the same manner as that described in Reference Example 1 except for using an equimolar amount of (4-hydroxyphenyl)(phenyl)methanone in place of 4-hydroxy-1-indanone, the reaction was carried out to obtain the titled compound.

$^1$H-NMR (CDCl$_3$) δ ppm: 7.14 (d, 1H), 7.29 (d, 2H), 7.48–7.65 (m, 3H), 7.82–7.92 (m, 2H), 7.94 (d, 2H), 8.54 (dd, 1H), 9.07 (d, 1H)

Reference Example 10

Synthesis of 1-{2-methyl-4-[(5-nitro-2-pyridinyl)oxy]phenyl}1-ethanone

According to the same manner as that described in Reference Example 1 except for using an equimolar amount of 1-(4-hydroxy-2-methyl-phenyl)-1-ethanone in place of 4-hydroxy-1-indanone, the reaction was carried out to obtain the titled compound.

$^1$H-NMR (CDCl$_3$) δ ppm: 2.58 (s, 3H), 2.61 (s, 3H), 7.05–7.11 (m, 3H), 7.83 (d, 1H), 8.49–8.54 (m, 1H), 9.05 (d, 1H)

Reference Example 11

Synthesis of 1-{4-[(5-nitro-2-pyridinyl)oxy]phenyl}-1-propanone

According to the same manner as that described in Reference Example 1 except for using an equimolar amount of 1-(4-hydroxyphenyl)-1-propanone in place of 4-hydroxy-1-indanone, the reaction was carried out to obtain the titled compound.

$^1$H-NMR (CDCl$_3$) δ ppm: 1.25 (t, 3H), 3.02 (q, 2H), 7.10–7.13 (m, 1H), 7.23–7.29 (m, 2H), 8.06–8.11 (m, 2H), 8.50–8.55 (m, 1H), 9.03–9.04 (m, 1H)

Reference Example 12

Synthesis of 2,3-dihydro-1H-inden-4-yl(5-nitro-2-pyridinyl)ether

According to the same manner as that described in Reference Example 1 except for using an equimolar amount of 4-indanol in place of 4-hydroxy-1-indanone, the reaction was carried out to obtain the titled compound.

$^1$H-NMR (CDCl$_3$) δ ppm: 2.02–2.13 (m, 2H), 2.67–2.73 (m, 2H), 3.00 (t, 2H), 6.90–6.94 (m, 1H), 7.01 (d, 1H), 7.17–7.26 (m, 2H), 8.44–8.48 (m, 1H), 9.03–9.04 (m, 1H)

Reference Example 13

Synthesis of 2,3-dihydro-7-methyl-1H-inden-4-yl(5-nitro-2-pyridinyl)ether

According to the same manner as that described in Reference Example 1 except for using an equimolar amount of 7-methyl-4-indanol in place of 4-hydroxy-1-indanone, the reaction was carried out to obtain the titled compound.

$^1$H-NMR (CDCl$_3$) δ ppm: 2.28 (s, 3H), 2.02–2.13 (m, 2H), 2.74 (t, 2H), 2.90 (t, 2H), 6.84 (d, 1H), 6.99–7.06 (m, 2H), 8.43–8.48 (m, 1H), 9.04 (d, 1H)

Reference Example 14

Synthesis of 5-nitro-2-(5,6,7,8-tetrahydro-1-naphthalenyloxy)pyridine

According to the same manner as that described in Reference Example 1 except for using an equimolar amount of 5,6,7,8-tetrahydro-1-naphthalenol in place of 4-hydroxy-1-indanone, the reaction was carried out to obtain the titled compound.

$^1$H-NMR (CDCl$_3$) δ ppm: 1.75–1.78 (m, 4H), 2.49–2.54 (m, 2H), 2.81–2.85 (m, 2H), 6.89 (d, 1H), 7.00 (d, 1H), 7.05 (d, 1H), 7.19 (t, 1H), 8.44–8.48 (m, 1H), 9.04 (d, 1H)

Reference Example 15

Synthesis of 2-(2,3-dimethylphenoxy)-5-nitropyridine

According to the same manner as that described in Reference Example 1 except for using an equimolar amount of 2,3-dimethylphenol in place of 4-hydroxy-1-indanone, the reaction was carried out to obtain the titled compound.

$^1$H-NMR (CDCl$_3$) δ ppm: 2.06 (s, 3H), 2.34 (s, 3H), 6.90–6.93 (m, 1H), 6.98–7.02 (m, 1H), 7.11–7.21 (m, 2H), 8.44–8.49 (m, 1H), 9.04 (d, 1H)

Reference Example 16

Synthesis of 5-nitro-2-phenoxypyridine

According to the same manner as that described in Reference Example 1 except for using an equimolar amount of phenol in place of 4-hydroxy-1-indanone, the reaction was carried out to obtain the titled compound.

$^1$H-NMR (CDCl$_3$) δ ppm: 7.00–7.05 (m, 1H), 7.13–7.24 (m, 2H), 7.26–7.34 (m, 1H), 7.42–7.50 (m, 2H), 8.44–8.50 (m, 1H), 9.05 (d, 1H)

Reference Example 17

Synthesis of 4-[(5-amino-2-pyridinyl)oxy]-1-indanone 1 g of 4-{(5-nitro-2-pyridinyl)oxy]-1-indanone obtained in Reference Example 1 was dissolved in 25 ml of methanol and the mixture was subjected to catalytic reduction at room temperature under normal pressure in the presence of 100 mg of 10% palladium-carbon. After 20 hours, the catalyst was removed by filtration and the filtrate was concentrated under reduced pressure to obtain a brown solid. The solid was purified by silica gel chromatography (eluent: ethyl acetate) to obtain 840 mg of the titled compound as a pale yellow powder.

Melting point: 119–123° C.

Reference Example 18

Synthesis of :6-[(5-amino-2-pyridinyl)oxy]-1-indanone

According to the same manner as that described in Reference Example 17 except for using an equimolar amount of 6-[(5-nitro-2-pyridinyl)oxy]-1-indanone obtained in Reference Example 2 in place of 4-[(5-nitro-2-pyridinyl)oxy]-1-indanone, the reaction was carried out to obtain the titled compound.

$^1$H-NMR (CDCl$_3$) δ ppm: 2.70–2.74 (m, 2H), 3.09–3.13 (m, 2H), 6.82 (d, 1H), 7.09–7.13 (m, 1H), 7.33–7.37 (m, 2H), 7.44–7.48 (m, 1H), 7.69 (d, 1H)

Reference Example 19

Synthesis of 6-(2,3-dihydro-1H-inden-5-yloxy)-3-pyridinylamine

According to the same manner as that described in Reference Example 17 except for using an equimolar amount of 2,3-dihydro-1H-inden-5-yl(5-nitro-2-pyridinyl)ether obtained in Reference Example 3 in place of 4-[(5-nitro-2-pyridinyl)oxy]-1-indanone, the reaction was carried out to obtain the titled compound.

$^1$H-NMR (CDCl$_3$) δ ppm: 2.0 (m, 2H), 2.8 (m, 4H), 3.5 (brs, 2H), 6.8–9.0 (m, 6H)

Reference Example 20

Synthesis of 5-[(5-amino-2-pyridinyl)oxy]-3,4-dihydro-1(2H)-naphthalenone

According to the same manner as that described in Reference Example 17 except for using an equimolar amount of 5-[(5-nitro-2-pyridinyl)oxy]-3,4-dihydro-1(2H)-naphthalenone obtained in Reference Example 4 in place of 4-[(5-nitro-2-pyridinyl)oxy]-1-indanone, the reaction was carried out to obtain the titled compound.

$^1$H-NMR (CDCl$_3$) δ ppm: 2.05–2.15 (m, 2H), 2.62–2.67 (m, 2H), 2.85–2.90 (m, 2H), 3.53 (brs, 2H), 6.78 (d, 1H), 7.11 (dd, 1H), 7.18 (dd, 1H), 7.30 (t, 1H), 7.66 (d, 1H), 7.88 (dd, 1H)

Reference Example 21

Synthesis of 3-[(5-amino-2-pyridinyl)oxy]-6,7,8,9-tetrahydro-5H-benzo[a]cyclohepten-5-one According to the same manner as that described in Reference Example 17 except for using an equimolar amount of 3-[(5-nitro-2-pyridinyl)oxy]-6,7,8,9-tetrahydro-5H-benzo(a) cyclohepten-5-one obtained in Reference Example 5 in place of 4-[(5-nitro-2-pyridinyl)oxy]-1-indanone, the reaction was carried out to obtain the titled compound.

$^1$H-NMR (CDCl$_3$) δ ppm: 1.81–1.88 (m, 4H), 2.69–2.74 (m, 2H), 2.87–2.92 (m, 2H), 6.76 (d, 1H), 7.06 (dd, 1H), 7.11–7.19 (m, 2H), 7.39 (d, 1H), 7.66 (d, 1H)

Reference Example 22

Synthesis of 1-{3-[(5-amino-2-pyridinyl)oxy]phenyl}1-ethanone

According to the same manner as that described in Reference Example 17 except for using an equimolar amount of 1-{3-[(5-nitro-2-pyridinyl)oxy]phenyl}-1-ethanone obtained in Reference Example 6 in place of 4-[(5-nitro-2-pyridinyl)oxy]-1-indanone, the reaction was carried out to obtain the titled compound.

yellow oily substance having a Rf value of 0.36 in silica gel thin-layer chromatography using ethyl acetate/hexane (2:1) as; a developing solvent

Reference Example 23

Synthesis of 1-{2-(5-amino-2-pyridinyl)oxy]phenyl}-1-ethanone

According to the same manner as that described in Reference Example 17 except for using an equimolar amount of 1-{2-(5-nitro-2-pyridinyl)oxy]phenyl}-1-ethanone obtained in Reference Example 7 in place of 4-[(5-nitro-2-pyridinyl)oxy]-1-indanone, the reaction was carried out to obtain the titled compound.

$^1$H-NMR (CDCl$_3$) δ ppm: 2.6 (s, 3H), 3.6 (brs, 2H), 6.8–7.8 (m, 7H)

Reference Example 24

Synthesis of 1-{4-[(5-amino-2-pyridinyl)oxy]phenyl}-1-ethanone

According to the same manner as that described in Reference Example 17 except for using an equimolar amount of 1-{4-[(5-nitro-2-pyridinyl)oxy]phenyl}-1-ethanone obtained in Reference Example 8 in place of 4-[(5-nitro-2-pyridinyl)oxy]-1-indanone, the reaction was carried out to obtain the titled compound.

$^1$H-NMR (CDCl$_3$) δ ppm: 2.5 (s, 3H), 3.6 (brs, 2H), 6.8–7.9 (m, 7H)

Reference Example 25

Synthesis of {4-[(5-amino-2-pyridinyl)oxy]phenyl}(phenyl)methanone

According to the same manner as that described in Reference Example 17 except for using an equimolar amount of (4-[(5-nitro-2-pyridinyl)oxy]phenyl)(phenyl)methanone obtained in Reference Example 9 in place of 4-[(5-nitro-2-pyridinyl)oxy]-1-indanone, the reaction was carried out to obtain the titled compound.

$^1$H-NMR (CDCl$_3$) δ ppm: 3.6 (brs, 2H), 6.8–7.8 (m, 12H)

Reference Example 26

Synthesis of 1-{4-[(5-amino-2-pyridinyl)oxy]-2-methyphenyl}-1-ethanone

According to the same manner as that described in Reference Example 17 except for using an equimolar amount of 1-{2-methyl-4-[(5-nitro-2-pyridinyl)oxy]phenyl}-1-ethanone obtained in Reference Example 10 in place of 4-[(5-nitro-2-pyridinyl)oxy]-1-indanone, the reaction was carried out to obtain the titled compound.

$^1$H-NMR (CDCl$_3$) δ ppm: 2.53 (s, 3H), 2.55 (s, 3H), 6.82 (d, 1H), 6.88–6.92 (m, 2H), 7.09–7.13 (m, 1H), 7.30–7.76 (m, 2H)

Reference Example 27

Synthesis of 1-{4-[(5-amino-2-pyridinyl)oxy]phenyl}-1-propanone

According to the same manner as that described in Reference Example 17 except for using an equimolar amount of 1-{4-[(5-nitro-2-pyridinyl)oxy]phenyl}-1-propanone obtained in Reference Example 11 in place of 4-[(5-nitro-2-pyridinyl)oxy]-1-indanone, the reaction was carried out to obtain the titled compound.

$^1$H-NMR (CDCl$_3$) δ ppm: 1.22 (t, 3H), 2.97 (q, 2H), 3.63 (brs, 2H), 6.83 (d, 1H), 7.05–7.07 (m, 2H), 7.10–7.14 (m, 1H), 7.74–7.76 (m, 1H), 7.94–7.99 (m, 2H)

Reference Example 28

Synthesis of 6-(2,3-dihydro-1H-inden-4-yloxy)-3-pyridinylamine

According to the same manner as that described in Reference Example 17 except for using an equimolar amount of 2,3-dihydro-1H-inden-4-yl(5-nitro-2-pyridinyl) ether obtained in Reference Example 12 in place of 4-[(5-nitro-2-pyridinyl)oxy]-1-indanone, the reaction was carried out to obtain the titled compound.

$^1$H-NMR (CDCl$_3$) δ ppm: 1.98–2.03 (m, 2H), 2.71–2.77 (m, 2H), 2.91–2.97 (m, 2H), 6.70–6.73 (m, 1H), 6.80–6.83 (m, 1H), 7.02–7.09 (m, 2H), 7.10–7.16 (m, 1H); 7.69–7.70 (m, 1H)

Reference Example 29

Synthesis of 6-[(7-methyl-2,3-dihydro-1H-inden-4-yl)oxy}-3-pyridinylamine

According to the same manner as that described in Reference Example 17 except for using an equimolar amount of 2,3-dihydro-7-methyl-1H-inden-4-yl(5-nitro-2-pyridinyl)ether obtained in Reference Example 13 in place of 4-[(5-nitro-2-pyridinyl)oxy]-1-indanone, the reaction was carried out to obtain the titled compound.

$^1$H-NMR (CDCl$_3$) δ ppm: 1.97–2.08 (m, 2H), 2.22 (s, 3H), 2.74 (t, 2H), 2.81–2.87 (m, 2H), 3.40 (brs, 2H), 6.69 (d, 2H), 6.76 (d, 2H), 6.95 (d, 1H), 7.02–7.05 (m, 1H), 7.66 (d, 1H)

Reference Example 30

Synthesis of 6-(5,6,7,8-tetrahydro-1-naphthalenyloxy)-3-pyridinylamine

According to the same manner as that described in Reference Example 17 except for using an equimolar amount of 5-nitro-2-(5,6,7,8-tetrahydro-1-naphthalenyloxy) pyridine obtained in Reference Example 14 in place of 4-[(5-nitro-2-pyridinyl)oxy]-1-indanone, the reaction was carried out to obtain the titled compound.

$^1$H-NMR (CDCl$_3$) δ ppm: 1.21–1.80 (m, 4H), 2.63–2.65 (m, 2H), 2.79 (m, 2H), 6.68 (dd, 1H), 6.76–6.79 (m, 1H), 6.89–6.91 (m, 1H), 7.03–7.11 (m, 2H), 7.69 (dd, 1H)

Reference Example 31

Synthesis of 6-(2,3-dimethylphenoxy)-3-pyridinylamine

According to the same manner as that described in Reference Example 17 except for using an equimolar amount of 2-(2,3-dimethylphenoxy)-5-nitropyridine obtained in Reference Example 15 in place of 4-[(5-nitro-2-pyridinyl)oxy]-1-indanone, the reaction was carried out to obtain the titled compound.

$^1$H-NMR (CDCl$_3$) δ ppm: 2.12 (s, 3H), 2.30 (s, 3H), 6.65–6.69 (m, 1H), 6.81–6.84 (m, 1H), 6.96–6.99 (m, 1H), 7.03–7.10 (m, 1H), 7.68–7.69 (m, 1H)

Reference Example 32

Synthesis of 6-phenoxy-3-pyridinylamine

According to the same manner as that described in Reference Example 17 except for using an equimolar amount of 5-nitro-2-phenoxypyridine obtained in Reference Example 16 in place of 4-[(5-nitro-2-pyridinyl)oxy]-1-indanone, the reaction was carried out to obtain the titled compound.

$^1$H-NMR (CDCl$_3$) δ ppm: 6.75–6.78 (m, 1H), 7.02–7.15 (m, 4H), 7.31–7.38 (m, 2H), 7.72–7.73 (m, 1H)

Reference Example 33

Synthesis of 2-[4-(2-methyl-1,3-dioxolane-2-yl)phenoxy]-5-nitropyridine 380 mg of 1-{4-[(5-nitro-2-pyridinyl)oxy]phenyl}-1-ethanone was dissolved in 5 ml of benzene and, after adding 98 μl of ethylene glycol and 3 mg of (±)-10-camphorsulfonic acid, the mixture was heated at reflux. After 3 hours, the reaction solution was extracted with ethyl acetate. The organic layer was washed in turn with a saturated sodium hydrogencarbonate solution and a saturated sodium chloride solution, dried over magnesium sulfate and then concentrated under reduced pressure. The resulting residue was purified by silica gel chromatography (eluent: ethyl acetate/ n-hexane (1:4)) to obtain the titled compound (280 mg).

$^1$H-NMR (CDCl$_3$) δ ppm: 1.6 (s, 3H), 3.8 (m, 2H), 4.0 (m, 2H), 7.0–9.0 (m, 7H)

Reference Example 34

Synthesis of 2-[3-(2-methyl-1,3-dioxolane-2-yl) phenoxy]-5-nitropyridine

According to the same manner as that described in Reference Example 33 except for using an equimolar amount of 1-{3-[(5-nitro-2-pyridinyl)oxy]phenyl}-1-ethanone obtained in Reference Example 6 in place of 1-{4-[(5-nitro-2-pyridinyl)oxy]phenyl}-1-ethanone, the reaction was carried out to obtain the titled compound.

$^1$H-NMR (CDCl$_3$) δ ppm: 1.7 (s, 3H), 3.6 (m, 2H), 3.8 (m, 2H), 7.0 (d, 1H), 7.1 (dd, 1H), 7.3 (ddd, 1H), 7.4 (ddd, 1H), 7.6 (dd, 1H), 8.4 (dd, 1H), 9.0 (d, 1H)

Reference Example 35

Synthesis of 6-[4-(2-methyl-1,3-dioxolane-2-yl) phenoxy]-3-pyridinylamine

According to the same manner as that described in Reference Example 17 except for using an equimolar amount of 2-{4-[(2-methyl-1,3-dioxolane-2-yl)phenoxy]-5-nitropyridine obtained in Reference Example 33 in place of 4-[(5-nitro-2-pyridinyl)oxy]-1-indanone, the reaction was carried out to obtain the titled compound.

$^1$H-NMR (CDCl$_3$) δ ppm: 1.6 (s, 3H), 3.5 (brs, 2H), 3.8 (m, 2H), 4.0 (m, 2H), 6.7–7.7 (m, 7H)

Reference Example 36

Synthesis of 6-[3-(2-methyl-1,3-dioxolane-2-yl) phenoxy]-3-pyridinylamine

According to the same manner as that described in Reference Example 17 except for using an equimolar amount of 2-{3-[(2-methyl-1,3-dioxolane-2-yl)phenoxy]-5-nitropyridine obtained in Reference Example 34 in place of 4-[(5-nitro-2-pyridinyl)oxy]-1-indanone, the reaction was carried out to obtain the titled compound.

$^1$H-NMR (CDCl$_3$) δ ppm: 1.9 (s, 3H), 3.8 (m, 2H), 4.0 (m, 2H), 6.8 (d, 1H), 7.0 (dd, 1H), 7.2 (m, 2H), 7.3 (dd, 1H), 7.6 (dd, 1H), 7.7 (d, 1H)

Reference Example 37

Synthesis of 1-{4-[(5-amino-2-pyridinyl)oxy] phenyl]-1-ethanol 8.14 g of 1-{4-[(5-nitro-2-pyridinyl)oxy]phenyl}-1-ethanone was dissolved in 15 ml of ethyl acetate and, after adding 2 g of 10% palladium-carbon, the mixture was stirred at 0° C. under partial hydrogen pressure overnight. After the completion of the reaction, the reaction solution was filtered with celite and the filtrate was concentrated under reduced pressure. The resulting residue was purified by silica gel chromatography. The compound synthesized in Reference Example 24 was obtained from a fraction prepared by using an eluent (ethyl acetate/n-hexane (2:1)), whereas, the titled compound (193 mg) was obtained from a fraction prepared by using an eluent (ethyl acetate/n-hexane (3:1)).

$^1$H-NMR (CDCl$_3$) δ ppm: 1.50 (d, 3H), 3.52 (brs, 2H), 4.90 (q, 1H), 6.77 (d, 1H), 7.02–7.11 (m, 3H), 7.33–7.38 (m, 2H), 7.72 (m, 1H)

Reference Example 38

Synthesis of ethyl 6-[(1-oxo-2,3-dihydro-1H-inden-4-yl)oxy]nicotinate 1.86 g of ethyl 6-chloronicotinate and 1.48 g of 4-hydroxy-1-indanone were dissolved in 15 ml of DMF. To the resulting solution, 0.97 g of potassium carbonate was added and the mixture was stirred at 120° C. After 1 hour, ethyl acetate and water were added to the reaction solution, thereby partitioning between an organic layer and an aqueous layer. The organic layer was washed with a saturated sodium chloride solution, dried over magnesium sulfate and then concentrated under reduced pressure. The residual oily substance was purified by column chromatography (eluent: ethyl acetate/n-hexane (1:4)) to obtain the titled compound (2.52 g) as an oily substance.

$^1$H-NMR (CDCl$_3$) δ ppm: 1.39 (t, 3H, J=7 Hz), 2.68 (m, 2H), 2.94 (m, 2H), 4.38 (q, 2H, J=7 Hz), 7.05 (d, 1H, J=8 Hz), 7.38 (d, 1H, J=8 Hz), 7.46 (t, 1H, J=8 Hz), 7.69 (d, 1H, J=8 Hz), 8.33 (d, 1H, J=8 Hz), 8.78 (s, 1H)

Reference Example 39

Synthesis of ethyl 6-[(1-oxo-2,3-dihydro-1H-inden-5-yl)oxy]nicotinate

According to the same manner as that described in Reference Example 38 except for using an equimolar amount of 5-hydroxy-1-indanone in place of 4-hydroxy-1-indanone, the reaction was carried out to obtain the titled compound.

$^1$H-NMR (CDCl$_3$) δ ppm: 1.39 (t, 3H), 2.73 (t, 2H), 3.16 (t, 2H), 4.39 (q, 2H), 7.04–8.83 (m, 6H)

Reference Example 40

Synthesis of ethyl 6-[(5-oxo-5,6,7,8-tetrahydro-1-naphthalenyl)oxy]nicotinate According to the same manner as that described in Reference Example 38 except for using an equimolar amount of 5-hydroxy-3,4-dihydro-1(2H)-naphthalenone in place of 4-hydroxy-1-indanone, the reaction was carried out to obtain the titled compound.

$^1$H-NMR (CDCl$_3$) δ ppm: 1.4 (t, 3H), 2.1 (m, 2H), 2.6 (m, 2H), 2.7 (m, 2H), 4.4 (dd, 2.H), 7.0–8.8 (m, 6H)

Reference Example 41

Synthesis of ethyl 6-(4-acetylphenoxy)nicotinate

According to the same manner as that described in Reference Example 38 except for using an equimolar amount of 1-(4-hydroxyphenyl)-1-ethanone in place of 4-hydroxy-1-indanone, the reaction was carried out to obtain the titled compound.

H-NMR (CDCl$_3$) δ ppm: 1.4 (t, 3H), 2.6 (s, 3H), 4.4 (dd, 2H), 7.0–8.8 (m, 6H)

Reference Example 42

Synthesis of 6-[(1-oxo-2,3-dihydro-1H-inden-4-yl)oxy]nicotinic acid 1.49 g of ethyl 6-[(1-oxo-2,3-dihydro-1H-inden-4-yl) nicotinate was dissolved in a mixed solvent of 10 ml of tetrahydrofuran and 10 ml of ethanol. To the resulting solution, 15 ml of an aqueous 1 N sodium hydroxide solution was added and the mixture was stirred at room temperature.

After 30 minutes, the reaction solution was concentrated under reduced pressure. To the resulting residue, water was added and the solution was neutralized with 1N hydrochloric acid. The deposited crystal was separated by filtration, washed with water and then dried at 40° C. under reduced pressure to obtain 1.27 g of the titled compound as a pale yellow crystal.

$^1$H-NMR (CDCl$_3$) δ ppm: 2.63 (m, 2H), 2.82 (m, 2H), 7.24 (d, 1H, J=8 Hz), 7.56 (m, 3H), 8.33 (d, 1H, J=8 Hz), 8.65 (s, 1H), 13.25 (brs, 1H)

Reference Example 43

Synthesis of 6-[(1-oxo-2,3-dihydro-1H-inden-5-yl)oxy]nicotonic acid

According to the same manner as that described in Reference Example 42 except for using an equimolar amount of ethyl 6-[(1-oxo-2,3-dihydro-1H-inden-5-yl)oxy]nicotinate obtained in Reference Example 39 in place of ethyl 6-[(1-oxo-2,3-dihydro-1H-inden-4-yl)oxy]nicotinate, the reaction was carried out to obtain the titled compound.

$^1$H-NMR (DMSO-d$_6$) δ ppm: 2.67 (t, 2H), 3.11 (t, 2H), 7.20–7.25 (m, 2H), 7.39 (s, 1H) 7.70 (d, 1H), 8.31–8.36 (m, 1H), 8.69–8.70 (m, 1H), 13.2 (brs, 1H)

Reference Example 44

Synthesis of 6-[(5-oxo-5,6,7,8-tetrahydro-1-naphthalenyl)oxy]nicotonic acid According to the same manner as that described in Reference Example 42 except for using an equimolar amount of ethyl 6-[(5-oxo-5,6,7,8-tetrahydro-1-naphthalenyl)oxy]nicotinate obtained in Reference Example 40 in place of ethyl 6-[(1-oxo-2,3-dihydro-1H-inden-4-yl) oxy]nicotinate, the reaction was carried out to obtain the titled compound.

$^1$H-NMR (DMSO-d$_6$) δ ppm: 2.0 (m, 2H), 2.6 (m, 4H), 7.2–8.6 (m, 6H)

Reference Example 45

Synthesis of 6-(4-acetylphenoxy)nicotonic acid

According to the same manner as that described in Reference Example 42 except for using an equimolar amount of ethyl 6-(4-acetylphenoxy)nicotinate obtained in Reference Example 41 in place of ethyl 6-[(1-oxo-2,3-dihydro-1H-inden-4-yl)oxy]nicotinate, the reaction was carried out to obtain the titled compound.

$^1$H-NMR (DMSO-d$_6$) δ ppm: 2.6 (s, 3H), 7.2–8.7 (m, 6H), 13.3 (brs, 1H)

Reference Example 46

Synthesis of 4-[(5-nitro-2-pyridinyl)oxy]-1-indanone ethylene ketal

According to the same manner as that described in Reference Example 33 except for using an equimolar amount of 4-{(5-nitro-2-pyridinyl)oxy]-1-indanone obtained in Reference Example 1 in place of 1-{4-[(5-nitro-2-pyridinyl)oxy]phenyl}-1-ethanone, the reaction was carried out to obtain the titled compound.

$^1$H-NMR (CDCl$_3$) δ ppm: 2.29 (t, 2H, J=6.93 Hz), 2.73 (t, 2H, J=6.93 Hz), 4.09–4.22 (m, 4H), 7.02 (d, 1H, J=9.24 Hz), 7.10–7.13 (m, 1H), 7.32–7.37 (m, 2H), 8.45–8.49 (m, 1H), 9.03 (d, 1H, J=2.31 Hz)

Reference Example 47

Synthesis of 4-[(5-amino-2-pyridinyl)oxy]-1-indanone ethylene ketal

According to the same manner as that described in Reference Example 17 except for using an equimolar amount of 4-{(5-nitro-2-pyridinyl)oxy]-1-indanone ethylene ketal obtained in Reference Example 46 in place of 4-[(5-nitro-2-pyridinyl)oxy]-1-indanone, the reaction was carried out to obtain the titled compound as an oily substance.

MS m/e=284 (M$^+$) for C$_{16}$H$_{16}$N$_2$O$_3$

Reference Example 48

Synthesis of 3-acetyloxy-7-[(5-nitro-2-pyridinyl)oxy]-1H-indene

To 5.00 g of 4-[(5-nitro-2-piridinyl)oxy]-1-indanone, 10 ml of isopropenyl acetate and 70 mg of p-toluenesulfonic acid were added and the mixture was stirred at 80° C. After 7.5 hours, the reaction solution was concentrated under reduced pressure. To the resulting residue, ethyl acetate was added and the solution was washed in turn with a saturated sodium hydrogencarbonate solution and a saturated sodium chloride solution. The solution extracted with ethyl acetate was dried over anhydrous magnesium sulfate and the solvent was distilled off. The resulting residue was washed with isopropyl ether in a hot state to obtain 4.70 g of the titled compound.

$^1$H-NMR (CDCl$_3$) δ ppm: 2.35 (s, 3H), 3.26 (d, 2H, J=2.31 Hz), 6.34 (t, 1H, J=2.31 Hz), 7.03–7.09 (m, 2H), 7.28 (d, 1H, J=9.24 Hz), 7.38–7.44 (m, 1H), 8.48 (dd, 1H, J=9.24, 2.97 Hz), 9.01 (d, 1H, J=2.97 Hz)

Reference Example 49

Synthesis of 3-acetyloxy-7-[(5-amino-2-pyridinyl)oxy]-1H-indene

To a solution of 3-acetyloxy-7-[(5-nitro-2-pyridinyl)oxy]-1H-indene (4.00 g) obtained in Reference Example 48 in tetrahydrofuran (120 ml), 47 mg of platinum dioxide as a catalyst was added and the mixture was stirred at room temperature under a hydrogen gas flow. After 1 hour, the catalyst was removed from the reaction solution by filtration and the filtrate was concentrated. The resulting residue was purified by silica gel column chromatography (eluent: hexane/ethyl acetate (1:1)) to obtain 1.67 g of the titled compound.

$^1$H-NMR (CDCl$_3$) δ ppm: 2.32 (s, 3H), 3.26 (d, 2H, J=2.31 Hz), 3.42 (brs, 2H), 6.28 (t, 1H, J=2.31 Hz), 6.74 (d, 1H, J=8.58 Hz), 6.90 (d, 1H, J=7.92 Hz), 7.02 (dd, 1H, J=8.58, 2.97 Hz), 7.11 (d, 1H, J=7.26 Hz), 7.26–7.32 (m, 1H), 7.64 (d, 1H, J=2.97 Hz)

Reference Example 50

Synthesis of 3-benzoyloxy-7-[(5-nitro-2-pyridinyl)oxy]-1H-indene

To 500 mg of 3-acetyloxy-7-[(5-nitro-2-pyridinyl)oxy]-1H-indene, 5 ml of benzoyl chloride and 15 mg of p-toluenesulfonic acid were added and the mixture was stirred at 100° C. After 1.5 hours, ethyl acetate was added to the reaction solution and the solution was washed in turn with a saturated sodium hydrogencarbonate solution and a saturated sodium chloride solution. The solution extracted with ethyl acetate was dried over anhydrous magnesium sulfate and the solvent was distilled off. The resulting residue was purified by silica gel column chromatography (eluent: hexane/ethyl acetate (10:1)) to obtain 130 mg of the titled compound as a white powder.

$^1$H-NMR (CDCl$_3$) δ ppm: 3.34 (d, 2H, 2.31 Hz), 6.52 (t, 1H, J=2.31 Hz), 7.06–7.12 (m, 2H), 7.38–7.70 (m, 5H), 8.23–8.27 (m, 2H), 8.51 (dd, 1H, J=8.91, 2.64 Hz), 9.04 (d, 1H, J=2.64 Hz)

Reference Example 51

Synthesis of 7-[(5-amino-2-pyridinyl)oxy]-3-benzoyloxy-1H-indene

According to the same manner as that described in Reference Example 49 except for using an equimolar amount of 3-benzoyloxy-7-[(5-nitro-2-pyridinyl)oxy]-1H-indene obtained in Reference Example 50 in place of 3-acetyloxy-7-[(5-nitro-2-pyridinyl)oxy]-1H-indene, the reaction was carried out to obtain the titled compound.

$^1$H-NMR (CDCl$_3$) δ ppm: 3.34 (d, 2H, J=2.31 Hz), 6.46 (t, 1H, J=2.31 Hz), 6.77 (d, 1H, J=8.57 Hz), 6.93–6.96 (m, 1H), 7.04–7.09 (m, 1H), 7.22–7.32 (m, 2H), 7.49–7.69 (m, 4H), 8.22–8.25 (m, 2H)

Reference Example 52

Synthesis of 3-isobutyryloxy-7-[(5-nitro-2-pyridinyl)oxy]-1H-indene

According to the same manner as that described in Reference Example 50 except for using isobutyryl chloride in place of benzoyl chloride, the reaction was carried out to obtain the titled compound.

$^1$H-NMR (CDCl$_3$) δ ppm: 1.35 (d, 6H, J=7 Hz), 2.81–2.92 (m, 1H), 3.26 (d, 2H, J=2 Hz), 6.35 (t, 1H, J=2 Hz), 7.03–7.09 (m, 2H), 7.25–7.44 (m, 2H), 8.47–8.52 (m, 1H), 9.02 (d, 1H, J=3 Hz)

Reference Example 53

Synthesis of 7-[(5-nitro-2-pyridinyl)oxy]-3-pivaloyloxy-1H-indene

According to the same manner as that described in Reference Example 50 except for using pivaloyl chloride in place of benzoyl chloride, the reaction was carried out to obtain the titled compound.

$^1$H-NMR (CDCl$_3$) δ ppm: 1.40 (s, 9H), 3.26 (d, 2H, J=2 Hz), 6.34 (t, 1H, J=2 Hz), 7.03–7.08 (m, 2H), 7.25–7.27 (m, 1H), 7.39–7.44 (m, 1H), 8.49 (dd, 1H, J=9 Hz, 3 Hz), 9.01 (d, 1H, J=3 Hz)

Reference Example 54

Synthesis of 1-acetoxy-5-[(5-nitro-2-pyridinyl)oxy]-3,4-dihydronaphthalene

According to the same manner as that described in Reference Example 48 except for using 5-[(5-nitro-2-pyridinyl)oxy]-3,4-dihydro-1(2H)-naphthalenone obtained in Reference Example 4 in place of 4-[(5-nitro-2-pyridinyl)oxy]-1-indanone, the reaction was carried out to obtain the titled compound.

¹H-NMR (CDCl₃) δ ppm: 2.32 (s, 3H), 2.40–2.44 (m, 2H), 2.66–2.72 (m, 2H), 5.75 (t, 1H, J=5 Hz), 6.98–7.26 (m, 4H), 8.48 (dd, 1H, J=3 Hz, 9 Hz), 9.03 (t, 1H, J=1 Hz)

Reference Example 55

Synthesis of 1-acetoxy-5-[(5-amino-2-pyridinyl) oxy]-3,4-dihydronaphthalene

According to the same manner as that described in Reference Example 49 except for using 1-acetoxy-5-[(5-nitro-2-pyridinyl)oxy]-3,4-dihydronaphthalene obtained in Reference Example 54 in place of 3-acetyloxy-7-[(5-nitro-2-pyridinyl)oxy]-1H-indene, the reaction was carried out to obtain the titled compound.

¹H-NMR (CDCl₃) δ ppm: 2.30 (s, 3H), 2.32–2.44 (m, 2H), 2.80 (t, 2H, J=8 Hz), 5.71 (t, 1H, J=5 Hz), 6.69 (d, 1H, J=9 Hz), 6.89–6.95 (m, 2H), 7.07 (dd, 1H, J=9 Hz, 3 Hz), 7.15 (t, 1H, J=8 Hz), 7.68 (d, 1H, J=3 Hz)

Reference Example 56

Synthesis of 6-[(5-nitro-2-pyridinyl)oxy]-3,4-dihydro-1(2H)-naphthalenone

According to the same manner as that described in Reference Example 1 except for using an equimolar amount of 6hydroxy-3,4-dihydro-1(2H)-naphthalenone in place of 4-hydroxy-1-indanone, the reaction was carried out to obtain the titled compound.

¹H-NMR (CDCl₃) δ ppm: 2.14–2.32 (m, 2H), 2.66–2.71 (m, 2H), 2.98–3.03 (m, 2H), 7.07–7.12 (m, 3H), 8.15 (d, 1H, J=3 Hz), 8.50–8.54 (m, 1H), 9.05 (d, 1H, J=3 Hz)

Reference Example 57

Synthesis of 1-acetoxy-6-[(5-nitro-2-pyridinyl)oxy]-3,4-dihydronaphthalene

According to the same manner as that described in Reference Example 48 except for using 4-[(5-nitro-2-pyridinyl)oxy]-3,4-dihydro-1(2H)-naphthalenone obtained in Reference Example 56 in place of 4-[(5-nitro-2-pyridinyl) oxy]-1-indanone, the reaction was carried out to obtain the titled compound.

¹H-NMR (CDCl₃) δ ppm: 2.31 (s, 3H), 2.45–2.53 (m, 2H), 2.90 (t, 2H, J=8 Hz), 5.73 (t, 1H, J=5 Hz), 6.95–6.97 (m, 2H), 7.03 (d, 1H, J=9 Hz), 7.16 (d, 1H, J=9 Hz), 8.47 (dd, 1H, J=9 Hz, 3 Hz), 9.05 (d, 1H, J=3 Hz)

Reference Example 58

Synthesis of 1-acetoxy-6-[(5-amino-2-pyridinyl) oxy]-3,4-dihydronaphthalene

According to the same manner as that described in Reference Example 49 except for using 1-acetoxy-6-[(5-nitro-2-pyridinyl)oxy]-3,4-dihydronaphthalene obtained in Reference Example 57 in place of 3-acetyloxy-7-[(5-nitro-2-pyridinyl)oxy]-1H-indene, the reaction was carried out to obtain the titled compound.

¹H-NMR (CDCl₃) δ ppm: 2.28 (s, 3H), 2.41–2.47 (m, 2H), 2.83 (t, 2H, J=8 Hz), 5.63 (t, 1H, J=5 Hz), 6.74–6.85 (m, 3H), 7.04–7.10 (m, 2H), 7.72 (d, 1H, J=3 Hz)

Reference Example 59

Synthesis of 4-[(5-cyano-2-pyridinyl)oxy]-1-indanone

According to the same manner as that described in Reference Example 1 except for using 5-cyano-2-chloropyridine in place of 2-chloro-5-nitropyridine, the reaction was carried out to obtain the titled compound.

¹H-NMR (CDCl₃) δ ppm: 2.68–2.72 (m, 2H), 2.92–2.96 (m, 2H), 7.14 (dd, 1H, J=Hz, 9 Hz), 7.37 (dd, 1H, J=1 Hz, 8 Hz), 7.45–7.51 (m, 1H), 7.70–7.73 (m, 1H), 7.98 (dd, 1H, J=2 Hz, 9 Hz), 8.43 (dd, J=1 Hz, 2 Hz)

Reference Example 60

Synthesis of 4-[(5-formyl-2-pyridinyl)oxy]-1-indanone

To a solution prepared by suspending 4.6 g of 4-[(5-cyano-2-pyridinyl)oxy]-1-indanone obtained in Reference Example 59 in 4.4 ml of water and 11 ml of formic acid, 2.6 g of raney nickel was added at 60° C.

The reaction solution was stirred at the same temperature for 5 hours and was subjected to the filtration. To the filtrate, ethyl acetate was added under ice-cooling. After the reaction solution was neutralized with 5N sodium hydroxide, the organic layer was washed with saturated sodium bicarbonate solution, water and saturated sodium chloride solution, and dried over anhydrous magnesium. The solvent was distilled off. The resulting residue was purified by silica gel column chromatography (eluent: hexane/ethyl acetate=5/1) to obtain 2.98 g of the titled compound.

¹H-NMR (CDCl₃) δ ppm: 2.68–2.72 (m, 2H), 2.93–2.98 (m, 2H), 7.16 (d, 1H, J=9 Hz), 7.39–7.42 (m, 1H), 7.46–7.52 (m, 1H), 7.70–7.73 (m, 1H), 8.25 (dd, 1H, J=2 Hz, 9 Hz), 8.59 (d, 1H, J=2 Hz), 10.00 (s, 1H).

EXAMPLE 1

Synthesis of 3,4-dichloro-N1-{6-[(1-oxo-2,3-dihydro-1H-inden-4-yl)oxy]-3-pyridinyl}benzamide To a solution prepared by dissolving 300 mg of 4-[(5-amino-2-pyridinyl)oxy]-1-indanone obtained in Reference Example 17 and 240 mg of 3,4-dichlorobenzoic acid in 5 ml of DMF, 250 mg of 1-ethyl-3-(3-dimethylaminopropyl) carbodiimide hydrochloride was added under ice cooling and the mixture was stirred at room temperature. After 24 hours, 10 ml of water was poured into the reaction solution and the solution was extracted with ethyl acetate. After the organic layer was washed with water and dried over anhydrous sodium sulfate, the solvent was distilled off under reduced pressure. The resulting residue was recrystallized from ethyl acetate to obtain 380 mg of the titled compound as a white powder. Melting point: 202–204° C.

EXAMPLE 2

Synthesis of N1-{6-[(1-oxo-2,3-dihydro-1H-inden-4-yl)oxy]-3-pyridinyl}-4-(trifluoromethyl)benzamide According to the same manner as that described in Example 1 except for using 4-(trifluoromethyl)benzoic acid in place of 3,4-dichlorobenzoic acid, the reaction was carried out to obtain the titled compound.

¹H-NMR (CDCl₃) δ ppm: 2.65–2.69 (m, 2H), 2.95–2.98 (m, 2H), 7.06–7.09 (m, 1H), 7.37–7.44 (m, 2H), 7.60–7.79 (m, 3H), 7.94 (brs, 1H), 7.90–8.02 (m, 2H), 8.24–8.36 (m, 2H)

EXAMPLE 3

Synthesis of 4-chloro-N1-{6-[(1-oxo-2,3-dihydro-1H-inden-4-yl)oxy]-3-pyridinyl}benzamide According to the same manner as that described in Example 1 except for using an equimolar amount of 4-chlorobenzoic acid in place of 3,4-dichlorobenzoic acid, the reaction was carried out to obtain the titled compound.

¹H-NMR (CDCl₃) δ ppm: 2.64–2.68 (m, 2H), 2.94–2.98 (m, 2H), 7.02–7.06 (m, 1H), 7.25–7.48 (m, 4H), 7.61–7.64 (m, 1H), 7.82–7.85 (m, 2H), 8.04 (brs, 1H), 8.23–8.29 (m, 2H)

EXAMPLE 4

Synthesis of 2,4-dichloro-N1-{6-[(1-oxo-2,3-dihydro-1H-inden-4-yl)oxy]-3-pyridinyl}benzamide According to the same manner as that described in Example 1 except for using an equimolar amount of 2,4-dichlorobenzoic acid in place of 3,4-dichlorobenzoic acid, the reaction was carried out to obtain the titled compound.

¹H-NMR (CDCl₃) δ ppm: 2.66–2.70 (m, 2H), 2.95–3.00 (m, 2H), 7.05–7.08 (m, 1H), 7.34–7.49 (m, 4H), 7.62–7.75 (m, 2H), 8.03 (brs, 1H), 8.23–8.30 (m, 2H)

EXAMPLE 5

Synthesis of 3,4-dichloro-N1-{6-[(3-oxo-2,3-dihydro-1H-inden-5-yl)oxy]-3-pyridinyl}benzamide According to the same manner as that described in Example 1 except for using an equimolar amount of 6-[(5-amino-2-pyridinyl)oxy]-1-indanone obtained in Reference Example 18 in place of 4-[(5-amino-2-pyridinyl)oxy]-1-indanone, the reaction was carried out to obtain the titled compound.

¹H-NMR (CDCl₃) δ ppm: 2.72–2.76 (m, 2H), 3.14 (t, 2H), 7.00–7.03 (m, 1H), 7.39 (dd, 1H), 7.45 (d, 1H), 7.51 (d, 1H), 7.56 (d, 1H), 7.72 (dd, 1H), 8.00 (d, 1H), 8.08 (brs, 1H), 8.21–8.24 (m, 2H)

EXAMPLE 6

Synthesis of N1-{6-[(3-oxo-2,3-dihydro-1H-inden-5-yl)oxy]-3-pyridinyl}-4-(trifluoromethyl)benzamide According to the same manner as that described in Example 1 except for using an equimolar amount of 4-(trifluoromethyl)benzoic acid in place of 3,4-dichlorobenzoic acid and using an equimolar amount of 6-[(5-amino-2-pyridinyl)oxy]-1-indanone obtained in Reference Example 18 in place of 4-[(5-amino-2-pyridinyl)oxy]-1-indanone, the reaction was carried out to obtain the titled compound.

¹H-NMR (CDCl₃) δ ppm: 2.04–2.76 (m, 2H), 3.12–3.17 (m, 2H), 7.01–7.04 (m, 1H), 7.37–7.41 (m, 1H), 7.46–7.47 (m, 1H), 7.50–7.59 (m, 1H), 7.74–7.77 (m, 2H), 7.99–8.02 (m, 2H), 8.10 (brs, 1H), 8.25–8.29 (m, 2H)

EXAMPLE 7

Synthesis of 3,4-dichloro-N1-{6-[(2,3-dihydro-1H-inden-5-yl)oxy]-3-pyridinyl}benzamide According to the same manner as that described in Example 1 except for using an equimolar amount of 6-[(2,3-dihydro-1H-inden-5-yl)oxy]-3-pyridinylamine obtained in Reference Example 19 in place of 4-[(5-amino-2-pyridinyl)oxy]-1-indanone, the reaction was carried out to obtain the titled compound.

¹H-NMR (CDCl₃) δ ppm: 2.0 (m, 2H), 2.8 (m, 4H), 6.8–8.5 (m, 9H), 10.5 (brs, 1H)

EXAMPLE 8

Synthesis of N1-{6-[(2,3-dihydro-1H-inden-5-yl)oxy]-3-pyridinyl}-3,4-difluorobenzamide According to the same manner as that described in Example 1 except for using an equimolar amount of 3,4-difluorobenzoic acid in place of 3,4-dichlorobenzoic acid and using an equimolar amount of 6-[(2,3-dihydro-1H-inden-5-yl)oxy]-3-pyridinylamine obtained in Reference Example 19 in place of 4-[(5-amino-2-pyridinyl)oxy]-1-indanone, the reaction was carried out to obtain the titled compound.

¹H-NMR (CDCl₃) δ ppm: 2.0 (m, 2H), 2.8 (m, 4H), 6.8–8.5 (m, 9H), 10.4 (brs, 1H)

EXAMPLE 9

Synthesis of 3,4-dichloro-N1-{6-[(5-oxo-5,6,7,8-tetrahydro-1-naphthalenyl)oxy]-3-pyridinyl}benzamide According to the same manner as that described in Example 1 except for using an equimolar amount of 5-[(5-amino-2-pyridinyl)oxy]-3,4-dihydro-1(2H)-naphthalenone obtained in Reference Example 20 in place of 4-[(5-amino-2-pyridinyl)oxy]-1-indanone, the reaction was carried out to obtain the titled compound.

1H-NMR (CDCl₃) δ ppm: 2.05–2.14 (m, 2H), 2.63–2.67 (m, 2H), 2.81–2.85 (m, 2H), 6.99–7.02 (m, 1H), 7.25–7.39 (m, 2H), 7.57–7.60 (m, 1H), 7.70–7.74 (m, 1H), 7.92–7.99 (m, 3H), 8.19–8.25 (m, 2H)

EXAMPLE 10

Synthesis of 3,4-dichloro-N1-{6-[(9-oxo-6,7,8,9-tetrahydro-5H-benzo[a]cyclohepten-2-yl)oxy]-3-pyridinyl benzamide According to the same manner as that described in Example 1 except for using an equimolar amount of 3-[(5-amino-2-pyridinyl)oxy]-6,7,8,9-tetrahydro-5H-benzo[a]cyclohepten-5-one obtained in Reference Example 21 in place of 4-[(5-amino-2-pyridinyl)oxy]-1-indanone, the reaction was carried out to obtain the titled compound.

¹H-NMR (CDCl₃) δ ppm: 1.81–1.91 (m, 4H), 2.72–2.76 (m, 2H), 2.91–2.95 (m, 2H), 6.94 (d, 1H), 7.17–7.26 (m, 2H), 7.45 (d, 1H), 7.53 (d, 1H), 7.70 (dd, 1H), 7.97 (d, 1H), 8.17 (dd, 1H), 8.24 (m, 1H)

EXAMPLE 11

Synthesis of N1-[6-(3-acetylphenoxy)-3-pyridinyl]-3,4-dichlorobenzamide

According to the same manner as that described in Example 1 except for using an equimolar amount of 1-{3-[(5-amino-2-pyridinyl)oxy]phenyl}-1-ethanone obtained in Reference Example 22 in place of 4-[(5-amino-2-pyridinyl)oxy]-1-indanone, the reaction was carried out to obtain the titled compound.

¹H-NMR (CDCl₃) δ ppm: 2.61 (s, 3H), 7.01 (d, 1H), 7.33–7.37 (m, 1H), 7.47–7.58 (m, 2H), 7.70–7.80 (m, 3H), 7.98–8.04 (m, 2H), 8.20–8.26 (m, 2H)

EXAMPLE 12

Synthesis of N1-[6-(2-acetylphenoxy)-3-pyridinyl]-3,4-dichlorobenzamide

According to the same manner as that described in Example 1 except for using an equimolar amount of 1-(2-[(5-amino-2-pyridinyl)oxy]phenyl)-1-ethanone obtained in Reference Example 23 in place of 4-[(5-amino-2-pyridinyl)oxy]-1-indanone, the reaction was carried out to obtain the titled compound.

¹H-NMR (DMSO-d₆) δ ppm: 12.5 (s, 3H), 7.2–8.4 (m, 10H), 10.6 (brs, 1H)

EXAMPLE 13

Synthesis of N1-[6-(2-acetylphenoxy)-3-pyridinyl]-3,4-difluorobenzamide

According to the same manner as that described in Example 1 except for using an equimolar amount of 3,4-difluorobenzoic acid in place of 3,4-dichlorobenzoic acid and using an equimolar amount of 1-{2-[(5-amino-2-pyridinyl)oxy]phenyl}-1-ethanone obtained in Reference Example 23 in place of 4-[(5-amino-2-pyridinyl)oxy]-1-indanone, the reaction was carried out to obtain the titled compound.

¹H-NMR (DMSO-d₆) δ ppm: 2.5 (s, 3H), 7.2–8.4 (m, 10H), 10.5 (brs, 1H)

EXAMPLE 14

Synthesis of N1-[6-(4-acetylphenoxy)-3-pyridinyl]-3,4-dichlorobenzamide

According to the same manner as that described in Example 1 except for using an equimolar amount of 1-{4-[(5-amino-2-pyridinyl)oxy]phenyl}-1-ethanone obtained in Reference Example 24 in place of 4-[(5-amino-2-pyridinyl)oxy]-1-indanone, the reaction was carried out to obtain the titled compound.

¹H-NMR (DMSO-d₆) δ ppm: 2.6 (s, 3H), 7.2–8.6 (m, 11H), 10.6 (brs, 1H)

EXAMPLE 15

Synthesis of N1-[6-(4-acetylphenoxy)-3-pyridinyl]-4-(trifluoromethyl)benzamide

According to the same manner as that described in Example 1 except for using an equimolar amount of 4-(trifluoromethyl)benzoic acid in place of 3,4-dichlorobenzoic acid and using an equimolar amount of 1-{4-[(5-amino-2-pyridinyl)oxy]phenyl}-1-ethanone obtained in Reference Example 24 in place of 4-[(5-amino-2-pyridinyl)oxy]-1-indanone, the reaction was carried out to obtain the titled compound.

¹H-NMR (DMSO-d₆) δ ppm: 2.6 (s, 3H), 7.2–8.6 (m, 11H), 10.7 (brs, 1H)

EXAMPLE 16

Synthesis of N1-[6-(4-benzoylphenoxy)-3-pyridinyl]-3,4-dichlorobenzamide

According to the same manner as that described in Example 1 except for using an equimolar amount of {4-[(5-amino-2-pyridinyl)oxy]phenyl}(phenyl)methanone obtained in Reference Example 25 in place of 4-[(5-amino-2-pyridinyl)oxy]-1-indanone, the reaction was carried out to obtain the titled compound.

¹H-NMR (DMSO-d₆) δ ppm: 7.21–8.59 (m, 15H), 10.57 (brs, 1H)

EXAMPLE 17

Synthesis of N1-[6-(4-benzoylphenoxy)-3-pyridinyl]-3,4-difluorobenzamide

According to the same manner as that described in Example 1 except for using an equimolar amount of 3,4-difluorobenzoic acid in place of 3,4-dichlorobenzoic acid and using an equimolar amount of {(4-[(5-amino-2-pyridinyl)oxy]phenyl}(phenyl)methanone obtained in Reference Example 25 in place of 4-[(5-amino-2-pyridinyl)oxy]-1-indanone, the reaction was carried out to obtain the titled compound.

¹H-NMR (DMSO-d₆) δ ppm: 7.2–8.6 (m, 15H), 10.6 (brs, 1H)

EXAMPLE 18

Synthesis of 3,4-difluoro-N1-{6-[4-(2-methyl-1,3-dioxolane-2-yl)phenoxy]-3-pyridinyl}benzamide According to the same manner as that described in Example 1 except for using an equimolar amount of 3,4-difluorobenzoic acid in place of 3,4-dichlorobenzoic acid and using an equimolar amount of 6-[4-(2-methyl-1,3-dioxolane-2-yl)phenoxy]-3-pyridinylamine obtained in Reference Example 35 in place of 4-[(5-amino-2-pyridinyl)oxy]-1-indanone, the reaction was carried out to obtain the titled compound.

¹H-NMR (DMSO-d₆) δ ppm: 1.5 (s, 3H), 3.7 (m, 2H), 4.0 (m, 2H), 7.0–8.5 (m, 10H), 10.5 (brs, 1H)

EXAMPLE 19

Synthesis of 3,4-dichloro-N1-{6-[3-(2-methyl-1,3-dioxolane-2-yl)phenoxy]-3-pyridinyl}benzamide According to the same manner as that described in Example 1 except for using an equimolar amount of 6-[3-(2-methyl-1,3-dioxolane-2-yl)phenoxy]-3-pyridinylamine obtained in Reference Example 36 in place of 4-[(5-amino-2-pyridinyl)oxy]-1-indanone, the reaction was carried out to obtain the titled compound.

¹H-NMR (DMSO-d₆) δ ppm: 1.6 (s, 3H), 3.7 (m, 2H), 4.0 (m, 2H), 7.0–8.5 (m, 10H), 10.6 (brs, 1H)

EXAMPLE 20

Synthesis of N1-{6-[4-(1-hydroxyethyl)phenoxy]-3-pyridinyl}-4-(trifluoromethyl)benzamide According to the same manner as that described in Example 1 except for using an equimolar amount of 4-(trifluoromethyl)benzoic acid in place of 3,4-dichloro benzoic acid and using an equimolar amount of 1-{4-[(5-amino-2-pyridinyl)oxy]phenyl)-1-ethanol obtained in Reference Example 37 in place of 4-[(5-amino-2-pyridinyl)oxy]-1-indanone, the reaction was carried out to obtain the titled compound.

¹H-NMR (DMSO-d₆) δ ppm: 1.3 (d, 3H), 4.7 (m, 1H), 5.1 (d, 1H), 7.0–8.5 (m, 11H), 10.6 (brs, 1H)

EXAMPLE 21

Synthesis of N1-[6-(4-acetyl-3-methylphenoxy)-3-pyridinyl]-3,4-dichlorobenzamide According to the same manner as that described in Example 1 except for using an equimolar amount of 1-{4-[(5-amino-2-pyridinyl)oxy]-2-methylphenyl}-1-ethanone obtained in Reference Example 26 in place of 4-[(5-amino-2-pyridinyl)oxy]-1-indanone, the reaction was carried out to obtain the titled compound.

¹H-NMR (CDCl₃) δ ppm: 2.55 (s, 3H), 2.58 (s, 3H), 6.99–7.04 (m, 3H), 7.58 (d, 1H), 7.70–7.73 (m, 1H), 7.89 (brs, 1H), 7.99 (d, 1-H), 8.21–8.26 (m, 1H), 8.33 (d, 1H)

EXAMPLE 22

Synthesis of N1-[6-(4-acetyl-3-methylphenoxy)-3-pyridinyl]-4-(trifluoromethyl)benzamide According to the same manner as that described in Example 1 except for using an equimolar amount of 4-(trifluoromethyl)benzoic acid in place of 3,4-dichlorobenzoic acid and using an equimolar amount of 1-(4-[(5-amino-2-pyridinyl)oxy]-2-methylphenyl}-1-ethanone obtained in Reference Example 26 in place of 4-[(5-amino-2-pyridinyl)oxy]-1-indanone, the reaction was carried out to obtain the titled compound.

$^1$H-NMR (CDCl$_3$) δ ppm: 2.56 (s, 3H), 2.58 (s, 3H), 6.99–7.06 (m, 2H), 7.76–7.81 (m, 3H), 7.95 (brs, 1H), 7.99–8.02 (m, 2H), 8.25–8.32 (m, 2H)

EXAMPLE 23

Synthesis of 3,4-dichloro-N1-[6-(4-propionylphenoxy)-3-pyridinyl]benzamide

According to the same manner as that described in Example 1 except for using an equimolar amount of 1-{4-[(5-amino-2-pyridinyl)oxy]phenyl}-1-propanone obtained in Reference Example 27 in place of 4-[(5-amino-2-pyridinyl)oxy]-1-indanone, the reaction was carried out to obtain the titled compound.

$^1$H-NMR (CDCl$_3$) δ ppm: 1.23 (t, 3H), 3.00 (q, 2H), 7.04 (d, 1H), 7.17–7.20 (m, 2H), 7.58 (d, 1H), 7.70–7.74 (m, 1H), 7.96 (brs, 1H), 7.99–8.03 (m, 3H), 8.23–8.30 (m, 2H)

EXAMPLE 24

Synthesis of N1-[6-(4-propionylphenoxy)-3-pyridinyl]-4-(trifluoromethyl)benzamide According to the same manner as that described in Example 1 except for using an equimolar amount of 4-trifluoromethylbenzoic acid in place of 3,4-dichlorobenzoic acid and using an equimolar amount of 1-{4-[(5-amino-2-pyridinyl)oxy]phenyl)-1-propanone obtained in Reference Example 27 in place of 4-[(5-amino-2-pyridinyl)oxy]-1-indanone, the reaction was carried out to obtain the titled compound.

$^1$H-NMR (CDCl$_3$) δ ppm: 1.23 (t, 3H), 3.00 (q, 2H), 7.04–7.07 (m, 1H), 7.18–7.22 (m, 2H) 7.76–7.79 (m, 2H), 7.98 (brs, 1H), 8.00–8.27 (m, 4H), 8.28–8.32 (m, 2H)

EXAMPLE 25

Synthesis of 3,4-dichloro-N1-(6-[(2,3-dihydro-1H-inden-4-yl)oxy]-3-pyridinyl}benzamide According to the same manner as that described in Example 1 except for using an equimolar amount of 6-[(2,3-dihydro-1H-inden-4-yl)oxy]-3-pyridinylamine obtained in Reference Example 28 in place of 4-[(5-amino-2-pyridinyl)oxy]-1-indanone, the reaction was carried out to obtain the titled compound.

$^1$H-NMR (CDCl$_3$) δ ppm: 1.99–2.10 (m, 2H), 2.70–2.75 (m, 2H), 2.94–2.99 (m, 2H), 6.88–6.93 (m, 2H), 7.09–7.12 (m, 1H), 7.16–7.22 (m, 1H), 7.57 (d, 1H), 7.68–7.72 (m, 1H), 7.79 (brs, 1H), 7.97 (d, 1H), 8.14–8.19 (m, 1H), 8.22 (d, 1H)

EXAMPLE 26

Synthesis of 3,4-dichloro-N1-(6-[(7-methyl-2,3-dihydro-1H-inden-4-yl)oxy]-3-pyridinyl)benzamide According to the same manner as that described in Example 1 except for using an equimolar amount of 6-[(7-methyl-2,3-dihydro-1H-inden-4-yl)oxy]-3-pyridinylamine obtained in Reference Example 29 in place of 4-[(5-amino-2-pyridinyl)oxy]-1-indanone, the reaction was carried out to obtain the titled compound.

$^1$H-NMR (CDCl$_3$) δ ppm: 1.99–2.10 (m, 2H), 2.25 (s, 3H), 2.70–2.76 (m, 2H), 2.84–2.89 (m, 2H), 6.82 (d, 1H), 6.90 (d, 1H), 7.00 (d, 1H), 7.56 (d, 1H), 7.67–7.71 (m, 1H), 7.80 (brs, 1H), 7.97 (d, 1H), 8.12–8.16 (m, 1H), 8.20 (d, 1H)

EXAMPLE 27

Synthesis of N1-{6-[(7-methyl-2,3-dihydro-1H-inden-4-yl)oxy]3-pyridinyl}-4-(trifluoromethyl)benzamide According to the same manner as that described in Example 1 except for using an equimolar amount of 4-(trifluoromethyl)benzoic acid in place of 3,4-dichlorobenzoic acid and using an equimolar amount of 6-[(7-methyl-2,3-dihydro-1H-inden-4-yl)oxy]-3-pyridinylamine obtained in Reference Example 29 in place of 4-[(5-amino-2-pyridinyl)oxy]-1-indanone, the reaction was carried out to obtain the titled compound.

$^1$H-NMR (CDCl$_3$) δ ppm: 1.99–2.11 (m, 2H), 2.26 (s, 3H), 2.71–2.76 (m, 2H), 2.84–2.90 (m, 2H), 6.83 (d, 1H), 6.92 (d, 1H), 7.00 (d, 1H), 7.74–7.77 (m, 2H), 7.83 (brs, 1H), 7.97–8.00 (m, 2H), 8.16–8.22 (m, 2H)

EXAMPLE 28

Synthesis of 3,4-dichloro-N1-{6-[(5,6,7,8-tetrahydro-1-naphthalenyl)oxy]-3-pyridinyl}benzamide According to the same manner as that described in Example 1 except for using an equimolar amount of 6-[(5,6,7,8-tetrahydro-1-naphthalenyl)oxy]-3-pyridinylamine obtained in Reference Example 30 in place of 4-[(5-amino-2-pyridinyl)oxy]-1-indanone, the reaction was carried out to obtain the titled compound.

$^1$H-NMR (CDCl$_3$) δ ppm: 1.73–1.77 (m, 4H), 2.56–2.60 (m, 2H), 2.79–2.81 (m, 2H), 6.84–6.91 (m, 2H), 6.96–6.98 (m, 1H), 7.10–7.16 (m, 1H), 7.57 (d, 1H), 7.68–7.71 (m, 1H), 7.80 (brs, 1H), 7.97 (d, 1H), 8.13–8.17 (m, 1H), 8.20 (d, 1H)

EXAMPLE 29

Synthesis of 3,4-dichloro-N1-[6-(2,3-dimethylphenoxy)-3-pyridinyl]benzamide

According to the same manner as that described in Example 1 except for using an equimolar amount of 6-(2,3-dimethylphenoxy)-3-pyridinylamine obtained in Reference Example 31 in place of 4-[(5-amino-2-pyridinyl)oxy]-1-indanone, the reaction was carried out to obtain the titled compound.

$^1$H-NMR (CDCl$_3$) δ ppm: 2.09 (5, 3H), 2.32 (s, 3H), 6.87–6.90 (m, 2H), 7.03–7.06 (m, 1H), 7.10–7.16 (m, 1H), 7.57 (d, 1H), 7.68–7.72 (m, 1H), 7.81 (brs, 1H), 7.97 (d, 1H), 8.13–8.17 (m, 1H), 8.20 (d, 1H)

EXAMPLE 30

Synthesis of 3,4-dichloro-N1-(6-phenoxy-3-pyridinyl)benzamide

According to the same manner as that described in Example 1 except for using an equimolar amount of 6-phenoxy-3-pyridinylamine obtained in Reference Example 32 in place of 4-[(5-amino-2-pyridinyl)oxy]-1-indanone, the reaction was carried out to obtain the titled compound.

$^1$H-NMR (CDCl$_3$) δ ppm: 6.86 (d, 1H), 7.04–7.07 (m, 2H), 7.14–7.19 (m, 1H), 7.32–7.38 (m, 2H), 7.46 (d, 1H), 7.63–7.67 (m, 1H), 7.91 (d, 1H), 8.08–8.12 (m, 1H), 8.20 (d, 1H), 8.63 (brs, 1H)

EXAMPLE 31

Synthesis of N1-(6-phenoxy-3-pyridinyl)-4-(trifluoromethyl)benzamide

According to the same manner as that described in Example 1 except for using an equimolar amount of 4-(trifluoromethyl)benzoic acid in place of 3,4-dichlorobenzoic acid and using an equimolar amount of 6-phenoxy-3-pyridinylamine obtained in Reference Example 32 in place of 4-[(5-amino-2-pyridinyl)oxy]-1-indanone, the reaction was carried out to obtain. the titled compound.

$^1$H-NMR (CDCl$_3$) δ ppm: 6.96 (d, 1H), 7.11–7.15 (m, 2H), 7.17–7.24 (m, 1H), 7.38–7.43 (m, 2H), 7.74–7.77 (m, 2H), 7.94 (brs, 1H), 7.97–8.00 (m, 2H), 8.19–8.24 (m, 1H), 8.26 (d, 1H)

EXAMPLE 32

Synthesis of 3,4-dichloro-N1-{6-[(1-oxo-2,3-dihydro-1H-inden-4-yl)oxy]-3-pyridinyl}benzamide hydrochloride After 0.27 g of 3,4-dichloro-N1-(6-[(1-oxo-2,3-dihydro-1H-inden-4-yl)oxy]-3-pyridinyl)benzamide obtained in Example 1 was dissolved in a mixed solvent of 5 ml of ethyl acetate and 2 ml of methanol at a hot state, 1.3 ml of a 4 N solution of hydrogen chloride in ethyl acetate was added to the solution with stirring. Then, the reaction solution was ice-cooled and the deposited crystal was isolated by filtration and dried under reduced pressure to obtain 0.27 g of the titled compound as a white powder. Melting point: 200–207° C.

$^1$H-NMR (DMSO-d$_6$) δ ppm: 2.62–2.67 (m, 2H), 2.84–2.88 (m, 2H), 7.18–7.22 (m, 1H), 7.45–7.52 (m, 3H), 7.83–7.98 (m, 2H), 8.24–8.28 (m, 2H), 8.50 (m, 1H), 10.64 (s, 1H)

EXAMPLE 33

Synthesis of 3,4-dichloro-N1-{6-[4-(2-methyl-1,3-dioxolane-2-yl)phenoxy]-3-pyridinyl}benzamide According to the same manner as that described in Example 1 except for using an equimolar amount of 6-[4-(2-methyl-1,3-dioxolane-2-yl)phenoxy]-3-pyridinylamine obtained in Reference Example 35 in place of 4-[(5-amino-2-pyridinyl)oxy]-1-indanone, the reaction was carried out to obtain the titled compound.

$^1$H-NMR (DMSO-d$_6$) δ ppm: 1.5 (s, 3H), 3.7 (m, 2H), 4.0 (m, 2H), 7.0–8.5 (m, 10H), 10.5 (brs, 1H)

EXAMPLE 34

Synthesis of 3,4-dichloro-N1-{6-[(1-hydroxy-2,3-dihydro-1H-inden-4-yl)oxy]-3-pyridinyl}benzamide After 413 mg of 3,4-dichloro-N1-{6-[(1-oxo-2,3-dihydro-1H-inden-4-yl)oxy]-3-pyridinyl}benzamide was dissolved in a mixed solvent of 4 ml of tetrahydrofuran and 1 ml of water, 23 mg of sodium tetrahydroborate was added and the mixture was stirred at room temperature. After 4 hours, acetone was added to the reaction solution to decompose excess sodium tetrahydroborate. Then, water was added and the solution was extracted with ethyl acetate. The organic (ethyl acetate) layer was washed with a saturated sodium chloride solution, dried over anhydrous magnesium sulfate and then concentrated under reduced pressure. To the resulting oily substance, diethyl ether was added and the deposited crystal was isolated by filtration to obtain 289 mg of the titled compound.

$^1$H-NMR (DMSO-d$_6$) δ ppm: 1.8 (m, 1H), 2.3–2.7 (m, 3H), 5.1 (m, 1H), 5.3 (d, 1H), 6.9–8.4 (m, 9H), 10.5 (brs, 1H)

EXAMPLE 35

Synthesis of 3,4-dichloro-N1-{6-[(1H-inden-7-yl)oxy]-3-pyridinyl}benzamide 1.50 g of 3,4-dichloro-N1-[6-(1-hydroxy-2,3-dihydro-1H-inden-4-yloxy)-3-pyridinyl]benzamide obtained in Example 34 was dissolved in 15 ml of acetic acid, and 1.16 g of pyridinium bromide perbromide was added to the resulting reaction solution and the mixture was stirred at 80° C. After 4 hours, the reaction solution was poured into iced water and extracted with ethyl acetate. The organic layer was washed with a saturated sodium chloride solution, dried over magnesium sulfate and then concentrated under reduced pressure. The resulting residue was purified by silica gel column chromatography (eluent: ethyl acetate/n-hexane (1:3)) to obtain 430 mg of the titled compound.

$^1$H-NMR (DMSO-d$_6$) δ ppm: 3.0 (d, 1H), 3.5 (dd, 1H), 5.1 (d, 1H), 6.0 (s, 1H), 7.1–8.5 (m, 9H), 10.6 (brs, 1H)

EXAMPLE 36

Synthesis of 3,4-dichloro-N1-{6-[4-(1-hydroxyethyl)phenoxy]-3-pyridinyl}benzamide According to the same manner as that described in Example 1 except for using an equimolar amount of 1-{4-[(5-amino-2-pyridinyl)oxy]phenyl}-1-ethanol obtained in Reference Example 37 in place of 4-[(5-amino-2-pyridinyl)oxy]-1-indanone, the reaction was carried out to obtain the titled compound.

$^1$H-NMR (DMSO-d$_6$) δ ppm: 1.3 (d, 3H), 4.7 (m, 1H), 5.7 (d, 1H), 7.0–8.5 (m, 10H), 10.6 (brs, 1H)

EXAMPLE 37

Synthesis of N3-(3,4-dichlorophenyl)-6-[(1-oxo-2,3-dihydro-1H-inden-4-yl)oxy]nicotinamide 188 mg of 6-[(1-oxo-2,3-dihydro-1H-inden-4-yl)oxy]nicotinic acid obtained in Reference Example 42 and 113 mg of 3,4-dichloroaniline were dissolved in 2 ml of DMF. To the resulting reaction solution, 114 mg of 1-hydroxybenzotriazole and 161 mg of 1-ethyl-3-(3-dimethylaminopropyl)carbodiimide hydroxhloride were added and the mixture was stirred at room temperature. After 2 hours, water was added to the reaction solution and the deposited solid was isolated by filtration. Then, the filtrate was extracted with a mixed solvent of ethyl acetate and tetrahydrofuran (THF) (former:latter=1:1). The organic layer was washed in turn with a saturated sodium hydrogencarbonate solution and a saturated sodium chloride solution, dried over magnesium sulfate and then concentrated under reduced pressure. The resulting solid was washed with diethyl ether to obtain 72 mg of the titled compound as a pale yellow crystal.

$^1$H-NMR (DMSO-d$_6$) δ ppm: 2.6 (m, 2H), 2.8 (m, 2H), 7.3–8.7 (m, 9H), 10.6 (brs, 1H)

EXAMPLE 38

Synthesis of N3-(3,4-difluorophenyl)-6-[(1-oxo-2,3-dihydro-1H-inden-4-yl)oxy]nicotinamide According to the same manner as that described in Example 37 except for using an equimolar amount of 3,4-difluoroaniline in place of 3,4-dichloroaniline, the reaction was carried out to obtain the titled compound.

$^1$H-NMR (DMSO-d$_6$) δ ppm: 2.6 (m, 2H), 2.9 (m, 2H), 7.3–8.7 (m, 9H), 10.5 (brs, 1H)

EXAMPLE 39

Synthesis of 6-[(1-oxo-2,3-dihydro-1H-inden-4-yl)oxy]-N3-[4-(trifluoromethyl)phenyl]nicotinamide According to the same manner as that described in Example 37 except for using an equimolar amount of 4-(trifluoromethyl)aniline in place of 3,4-dichloroaniline, the reaction was carried out to obtain the titled compound.

$^1$H-NMR (DMSO-d6) δ ppm: 2.65 (m, 2H), 2.86 (m, 2H), 7.32 (d, 1H, J=8 Hz), 7.54 (m, 3H), 7.74 (d, 2H, J=8 Hz), 7.98 (d, 2H, J=8 Hz), 8.43 (d, 1H, J=8 Hz), 8.71 (s, 1H), 10.65 (s, 1H)

EXAMPLE 40

Synthesis of N3-(3,4-dichlorophenyl)-6-[(1-oxo-2,3-dihydro-1H-inden-5-yl)oxy]nicotinamide According to the same manner as that described in Example 37 except for using an equimolar amount of 6-[(1-oxo-2,3-dihydro-1H-inden-5-yl)oxy]nicotinic acid obtained in Reference Example 43 in place of 6-[(1-oxo-2,3-dihydro-1H-inden-4-yl)oxy]nicotinic acid, the reaction was carried out to obtain the titled compound.

$^1$H-NMR (DMSO-d$_6$) δ ppm: 2.6 (m, 2H), 3.1 (m, 2H), 7.2–8.7 (m, 9H), 10.4 (brs, 1H)

EXAMPLE 41

Synthesis of N3-(3,4-difluorophenyl)-6-[(5-oxo-5,6,7,8-tetrahydro-1-naphthalenyl)oxy]nicotinamide According to the same manner as that described in Example 37 except for using an equimolar amount of 6-[(5-oxo-5,6,7,8-tetrahydro-1-naphthalenyl)oxy]nicotinic acid obtained in Reference Example 44 in place of 6-[(1-oxo-2,3-dihydro-1H-inden-4-yl)oxy]nicotinic acid and using an equimolar amount of 3,4-difluoroaniline in place of 3,4-dichloroaniline, the reaction was carried out to obtain the titled compound.

$^1$H-NMR (DMSO-d$_6$) δ ppm: 2.0 (m, 2H), 2.6 (m, 2H), 2.7 (m, 2H), 7.0–8.6 (m, 9H), 10.5 (brs, 1H)

EXAMPLE 42

Synthesis of N3-(3,4-dichlorophenyl)-6-[(5-oxo-5,6,7,8-tetrahydro-1-naphthalenyl)oxy]nicotinamide According to the same manner as that described in Example 37 except for using an equimolar amount of 6-[(5-oxo-5,6,7,8-tetrahydro-1-naphthalenyl)oxy]nicotinic acid obtained in Reference Example 44 in place of 6-[(1-oxo-2,3-dihydro-1H-inden-4-yl)oxy]nicotinic acid, the reaction was carried out to obtain the titled compound.

$^1$H-NMR (DMSO-d$_6$) δ ppm: 2.0 (m, 2H), 2.7 (m, 4H), 7.2–8.7 (m, 9H), 10.5 (brs, 1H)

EXAMPLE 43

Synthesis of 6-(4-acetylphenoxy)-N3-(3,4-dichlorophenyl)nicotinamide

According to the same manner as that described in Example 37 except for using an equimolar amount of 6-(4-acetylphenoxy)nicotinic acid obtained in Reference Example 45 in place of 6-[(1-oxo-2,3-dihydro-1H-inden-4-yl)oxy]nicotinic acid, the reaction was carried out to obtain the titled compound.

$^1$H-NMR (DMSO-d$_6$) δ ppm: 2.6 (s, 3H), 7.3–8.7 (m, 10H), 10.6 (brs, 1H)

EXAMPLE 44

Synthesis of 6-(4-acetylphenoxy)-N3-[4-(trifluoromethyl)phenyl]nicotinamide

According to the same manner as that described in Example 37 except for using an equimolar amount of 6-(4-acetylphenoxy)nicotinic acid obtained in Reference Example 45 in place of 6-[(1-oxo-2,3-dihydro-1H-inden-4-yl)oxy]nicotinic acid and using an equimolar amount of 4-(trifluoromethyl)aniline in place of 3,4-dichloroaniline, the reaction was carried out to obtain the titled compound.

$^1$H-NMR (DMSO-d$_6$) δ ppm: 2.6 (s, 3H), 7.3–8.8 (m, 10H), 10.7 (brs, 1H)

EXAMPLE 45

Synthesis of 3,4-dichloro-N1-[6-{[1-(1,3-dioxolane-2-yl)-2,3-dihydro-1H-inden -4-yl]oxy}-3-pyridinyl]benzamide To a solution of 4-[(5-amino-2-pyridinyl)oxy]-1-indanone ethylene ketal (1.97 g) obtained in Reference Example 47 and triethylamine (2.9 ml) in tetrahydrofuran (35 ml), a solution of 3,4-dichlorobenzoyl chloride (1.45 g) in tetrahydrofuran (15 ml) was added dropwise at 0° C. and the reaction mixture was stirred at the same temperature for 5 minutes. Then, the reaction mixture was extracted by adding ethyl acetate and water. The resulting solution extracted with ethyl acetate was dried over anhydrous magnesium sulfate and the solvent was distilled off. The resulting residue was washed in turn with ether and hot diisopropyl ether to obtain 2.69 g of the titled compound.

$^1$H-NMR (DMSO-d6) δ ppm: 2.14–2.20 (m, 2H), 2.57–2.62 (m, 2H), 3.98–4.17 (m, 4H), 7.06–7.11 (m, 2H), 7.22 (dd, 1H, J=7.58 Hz, J=0.98 Hz), 7.29–7.34 (m, 1H), 7.84 (d, 1H, J=8.57 Hz), 7.92–7.96 (m, 1H), 8.18–8.23 (m, 2H), 8.45 (d, 1H, J=2.63 Hz), 10.55 (s, 1H)

EXAMPLE 46

Synthesis of N1-{6-[(3-acetoxy-1H-inden-7-yl)oxy]-3-pyridinyl}-3,4-dichlorobenzamide A mixture of 1.00 g of 3,4-dichloro-N1-[6-(1-oxo-2,3-dihydro-1H-inden-4-yl)oxy]-3-pyridinyl]benzamide obtained in Example 1, 50 mg of p-toluenesulfonic acid and 5 ml of isopropenyl acetate was stirred overnight at 70° C.

The reaction mixture was concentrated and the resulting residue was extracted with ethyl acetate. This extracted solution was washed in turn with a saturated sodium hydrogencarbonate solution and a saturated sodium chloride solution and dried over anhydrous magnesium sulfate, and then the solvent was distilled off. The resulting residue was purified by silica gel column chromatography (eluent: hexane/ethyl acetate (2:1)) to obtain the titled compound (230 mg, white powder). Melting point: 161–164° C.

$^1$H-NMR (CDCl$_3$) δ ppm: 2.35 (s, 3H), 3.29 (d, 2H, J=1.98 Hz), 6.32 (t, 1H, J=1.98 Hz), 6.97–7.04 (m, 2H), 7.22 (d, 1H, J=7.58 Hz), 7.38 (t, 1H, J=7.58 Hz), 7.59 (d, 1H, J=8.25 Hz), 7.73–7.75 (m, 1H), 7.88 (brs, 1H), 8.01 (d, 1H, J=1.65 Hz), 8.26–8.29 (m, 2H)

EXAMPLE 47

Synthesis of 3,4-dichloro-N1-(6-[(1-hydroxyimino-2,3-dihydro-1H-inden-4-yl)oxy]-3-pyridinyl}benzamide 800 mg of 3,4-dichloro-N1-{6-[(1-oxo-2,3-dihydro-1H-inden-4-yl)oxy]-3-pyridinyl}benzamide obtained in Example 1 and 670 mg of hydroxyammonium chloride (hydroxylamine hydrochloride) were suspended in 40 ml of ethanol and, after adding 5.4 ml of pyridine to the resulting suspension, the mixture was stirred at 60° C. After 30 minutes, the reaction solution was distilled off under reduced pressure. To the resulting residue, 60 ml of ethyl acetate was added and the solution was washed in turn with water and a saturated sodium chloride solution and then dried over anhydrous magnesium sulfate. After ethyl acetate was distilled off, ether was added to the residue and the deposited crystal was isolated by filtration and then washed with ether to obtain the titled compound (430 mg, white powder).

$^1$H-NMR (DMSO-d$_6$) δ ppm: 2.76 (s, 4H), 7.09 (d, 1H, J=8 Hz), 7.11 (d, 1H, J=8 Hz), 7.33 (t, 1H, J=8 Hz), 7.43 (d, 1H, J=8 Hz), 7.84 (d, 1H, J=8 Hz,), 7.94 (dd, 1H, J=8 Hz, 2 Hz), 8.21 (dd, 1H, J=8 Hz, 2 Hz), 8.22 (s, 1H), 8.46 (d, 1H, J=2 Hz), 10.56 (s, 1H), 10.96 (s, 1H)

EXAMPLE 48

Synthesis of 3,4-dichloro-N1-{6-[(1-methoxyimino-2,3-dihydro-1H-inden-4-yl)oxy]-3-pyridinyl}benzamide According to the same manner as that described in Example 47 except for using an equimolar amount of O-methylhydroxyammonium chloride in place of hydroxyammonium chloride, the reaction was carried out to obtain the titled compound (530 mg, white powder).

$^1$H-NMR (DMSO-d$_6$) δ ppm: 2.77 (m, 4H), 3.09 (s, 3H), 7.13 (d, 1H, J=8 Hz), 7.14 (d, 1H, J=8 Hz), 7.35 (t, 1H, J=8 Hz), 7.44 (d, 1H, J=8 Hz), 7.84 (d, 1H, J=8 Hz), 7.94 (d, 1H, J=8 Hz), 8.22 (d, 1H, J=8 Hz), 8.22 (s, 1H), 8.46 (s, 1H), 10.58 (s, 1H)

EXAMPLE 49

Synthesis of N1-{6-[(1-acetoxyimino-2,3-dihydro-1H-inden-4-yl)oxy]-3-pyridinyl}-3,4-dichlorobenzamide 650 mg of N1-{6-[(1-hydroxyimino-2,3-dihydro-1H-inden-4-yl)oxy]-3-pyridinyl}benzamide obtained in Example 47 was dissolved in 10 ml of tetrahydrofuran. To the resulting reaction solution, 1.2 ml of pyridine and 0.7 ml of acetic anhydride were added and the mixture was stirred at room temperature. After 17 hours, the reaction solution was distilled off under reduced pressure and 15 ml of ethyl acetate and 15 ml of water were added to the resulting residue. Then, the deposited powder was isolated by filtration and washed in turn with water and ethyl acetate to obtain the titled compound (310 mg).

$^1$H-NMR (DMSO-d$_6$) δ ppm: 2.20 (s, 3H), 2.84 (m, 2H), 3.01 (m, 2H), 7.16 (d, 1H, J=8 Hz), 7.28 (d, 1H, J=8 Hz), 7.44 (t, 1H, J=8 Hz), 7.59 (d, 1H, J=8 Hz), 7.84 (d, 1H, J=8 Hz), 7.95 (d, 1H, J=8 Hz), 8.22 (s, 1H), 8.24 (d, 1H, J=8 Hz), 8.47 (s, 1H), 10.59 (s, 1H)

EXAMPLE 50

Synthesis of 3,4-dichloro-N1-{6-(3-ethoxy-1H-inden-7-yloxy)-3-pyridinyl}benzamide 3.5 g of 3,4-dichloro-N1-{6-(1-oxo-2,3-dihydro-1H-inden-4-yl)oxy]-3-pyridinyl}benzamide obtained in Example 1 was suspended in 140 ml of ethanol. To the suspension, 14 ml of ethyl orthoformate, 820 mg of (±)-10-camphorsulfonic acid and 3.5 g of 4A molecular sieves were added and the mixture was heated at reflux for 30 minutes. After air cooling, the reaction mixture was filtered. To the filtrate, 8.5 ml of an aqueous 1N sodium hydroxide solution was added and the solvent was distilled off under reduced pressure. To the resulting residue, 100 ml of ethyl acetate was added and the solution was washed in turn with water and a saturated sodium hydrogencarbonate solution and then dried over magnesium sulfate. After drying, the solvent was distilled off and the resulting residue was purified by silica gel column chromatography (eluent: hexane/ethyl acetate (4:1)) to obtain the titled compound (white powder, 530 mg).

$^1$H-NMR (DMSO-d) δ ppm: 1.38 (t, 3H, J=7 Hz), 3.05 (d, 2H, J=2 Hz), 4.07 (q, 2H, J=7 Hz), 5.37 (t, 1H, J=2 Hz), 6.99 (d, 1H, J=8 Hz), 7.10 (d, 1H, J=8 Hz), 7.20 (d, 1H, J=8 Hz), 7.36 (t, 1H, J=8 Hz), 7.84 (d, 1H, J=8 Hz), 7.94 (d, 1H, J=8 Hz), 8.20 (dd, 1H, J=8 Hz, 3 Hz), 8.22 (s, 1H), 8.44 (d, 1H, J=3 Hz), 10.56 (s, 1H)

EXAMPLE 51

Synthesis of N1-{6-[(3-acetyloxy-1H-inden-7-yl)oxy]-3-pyridinyl}-4-(trifluoromethyl)benzamide According to the same manner as that described in Example 1 except for using an equimolar amount of 3-acetyloxy-7-[(5-amino-2-pyridinyl)oxy]-1H-indene obtained in Reference Example 49 in place of 4-[(5-amino-2-pyridinyl)oxy]-1-indanone and using an equimolar amount of 4-(trifluoromethyl)benzoic acid in place of 3,4-dichlorobenzoic acid, the reaction was carried out to obtain the titled compound.

MS m/e=454 (M$^+$) for C$_{24}$H$_{17}$F$_3$N$_2$O$_4$ $^1$H-NMR (CDCl1) δ ppm: 2.35 (s, 3H), 3.28 (d, 2H, J=2.31 Hz), 6.32 (t, 1H, J=2.31 Hz), 6.97–7.04 (m, 2H), 7.19–7.40 (m, 2H), 7.68 (d, 2H, J=8.10 Hz), 7.89 (brs, 1H), 7.99 (d, 2H, J=7.83 Hz), 8.23–8.25 (m, 2H)

EXAMPLE 52

Synthesis of N1-{6-[(3-benzoyloxy-1H-inden-7-yl)oxy]-3-pyridinyl}-3,4-dichlorobenzamide According to the same manner as that described in Example 45 except for using an equimolar amount of 7-[(5-amino-2-pyridinyl)oxy]-3-benzoyloxy-1H-indene obtained in Reference Example 51 in place of 4-[(5-amino-2-pyridinyl)oxy]-1-indanone ethylene ketal, the reaction was carried out to obtain the titled compound.

¹H-NMR (CDCl₃) δ ppm: 3.35 (d, 2H, J=2.31 Hz), 6.49 (t, 1H, J=2.31 Hz), 6.98–7.06 (m, 2H), 7.30–7.39 (m, 2H), 7.52–7.73 (m, 5H), 7.82 (brs, 1H), 7.99 (d, 1H, J=1.98 Hz), 8.20–8.26 (m, 4H)

EXAMPLE 53

Synthesis of 3,4-dichloro-N1-(6-[(3-isobutyryloxy-1H-inden-7-yl)oxy]-3-pyridinyl)benzamide To a solution of 3-isobutyryloxy-7-[(5-nitro-2-pyridinyl)oxy]-1H-indene. (280 mg) obtained in Reference Example 52 in THF (50 ml), 10 mg of platinum oxide was added and catalytic reduction was carried out in a hydrogen gas flow at room temperature under normal pressure. After 45 minutes, the reaction solution was filtered and 0.125 ml of triethylamine was added to the filtrate. To the reaction solution, a solution of 3,4-dichlorobenzoyl chloride (170 mg) in THF (5 ml) was added under ice cooling and the mixture was stirred for 10 minutes. After the reaction solution was filtered and concentrated, ethyl acetate was added to the residue and the solution was washed with water. The organic layer was dried over anhydrous magnesium sulfate and the solvent was distilled off. The residue was washed with ether to obtain 72 mg of the titled compound as a white solid.

¹H-NMR (CDCl₃) δ ppm: 1.35 (d, 6H, J=7 Hz), 2.81–2.91 (m, 1H), 3.23 (d, 2H, J=2 Hz), 6.28 (t, 1H, J=2 Hz), 6.92–7.00 (m, 2H), 7.16 (dd, 1H, J=7 Hz, 1 Hz), 7.31–7.36 (m, 1H), 7.53 (d, 1H, J=9 Hz), 7.68 (dd, 1H, J=8 Hz, 2 Hz), 7.96 (d, 1H, J=2 Hz), 8.12–8,21 (m, 3H)

EXAMPLE 54

Synthesis of 3,4-dichloro-N1-(6-[(3-pivaloyloxy-1H-inden-7-yl)oxy]-3-pyridinyl)benzamide According to the same manner as that described in Example 53 except for using an equimolar amount of 7-[(5-nitro-2-pyridinyl)oxy]-3-pivaloyloxy-1H-indene obtained in Reference Example 53 in place of 3-isobutyryloxy-7-[(5-nitro-2-pyridinyl)oxy]-1H-indene, the reaction was carried out to obtain the titled compound.

¹H-NMR (CDCl₃) δ ppm: 1.40 (s, 9H), 3.25 (d, 2H, J=2 Hz), 6.95 (d, 1H, J=9 Hz), 7.00 (d, 1H, J=8 Hz), 7.17 (d, 1H, J=8 Hz), 7.17 (d, 1H, J=7 Hz), 7.32–7.38 (m, 1H), 7.55 (d, 1H, J=7 Hz), 7.69–7.73 (m, 1H), 7.98 (d, 1H, J=2 Hz), 8.06–8,23 (m, 3H)

EXAMPLE 55

Synthesis of N1-{6-[(1-acetoxy-3,4-dihydronaphthalene-5-yl)oxy]pyridine-3-yl}-3,4-dichlorobenzamide According to the same manner as that described in Example 45 except for using an equimolar amount of 1-acetoxy-5-[(5-amino-2-pyridinyl)oxy]-3,4-dihydronaphthalene obtained in Reference Example 55 in place of 4-[(5-amino-2-pyridinyl)oxy]-1-indanone ethylene ketal, the reaction was carried out to obtain the titled compound.

¹H-NMR (CDCl₃) δ ppm: 2.31 (s, 3H), 2.35–2.43 (m, 2H), 2.74 (t, 2H, J=8 Hz), 5.72 (t, 1H, J=5 Hz), 6.91 (d, 1H, J=9 Hz), 6.97–7.02 (m, 2H), 7.18–7.24 (m, 1H), 7.57 (d, 1H, J=8 Hz), 7.68–7.72 (m, 1H), 7.85 (bs, 1H), 7.98 (d, 1H, J=2 Hz), 8.15–8.21 (m, 2H)

EXAMPLE 56

Synthesis of N1-{6-[(1-acetoxy-3,4-dihydronaphthalene-6-yl)oxy]pyridine-3-yl}-N3-(3,4-dichlorophenyl)urea To a solution of 1-acetoxy-6-[(5-amino-2-pyridinyl)oxy]-3,4-dihydronaphthalene (360 mg) obtained in Reference Example 58 and triethylamine (0.34 ml) in THF (10 ml), a solution of 3,4-dichlorophenyl (230 mg) in THF (10 ml) was added dropwise under ice cooling. The reaction solution was stirred for 3 hours gradually warming up to room temperature. The reaction solution was concentrated under reduced pressure and the residue was purified by silica gel column chromatography (eluent: hexane/ethyl acetate (1:1)) to obtain 340 mg of the titled compound as a white powder.

¹H-NMR (CDCl₃) δ ppm: 2.30 (s, 3H), 2.39–2.44 (m, 2H), 2.75–2.81 (m, 2H), 5.66 (t, 1H, J=5 Hz), 6.83–6.86 (m, 3H), 7.04–7.14 (m. 2H), 7.25–7.28 (m, 1H), 7.48 (d, 1H, J=2 Hz), 7.67 (bs, 1H), 7.80 (bs, 1H), 7.91–7.96 (m, 2H)

EXAMPLE 57

Synthesis of N1-{6-[(3-acetoxy-1H-inden-7-yl)oxy]pyridin-3-yl}-N3-(3,4-dichlorophenyl)urea According to the same manner as that described in Example 56 except for using an equimolar amount of 3-acetyloxy-7-[(5-amino-2-pyridinyl)oxy]-1H-indene obtained in Reference Example 49 in place of 1-acetoxy-6-[(5-amino-2-pyridinyl)oxy]-3,4-dihydronaphthalene, the reaction was carried out to obtain the titled compound.

¹H-NMR (DMSO-d₆) δ ppm: 9.10 (s, 1H), 8.91 (s, 1H), 8.15 (d, 1H, J=2 Hz), 8.01 (dd, 1H, J=9 Hz, 2 Hz), 7.87 (d, 1H, J=2 Hz), 7.52 (d, 1H, J=9 Hz), 7.37 (t, 1H, J=8 Hz), 7.35 (d, 1H, J=9 Hz), 7.17 (d, 1H, J=8 Hz), 7.08 (d, 1H, J=9 Hz), 6.99 (d, 1H, J=8 Hz), 6.26 (s, 1H), 3.21 (s, 2H), 2.35 (s, 3H)

EXAMPLE 58

Synthesis of N1-{6-[(3-acetoxy-1H-inden-7-yl)oxy]pyridin-3-yl}-N3-[4-(trifluoromethyl)phenyl]urea According to the same manner as that described in Example 56 except for using an equimolar amount of 3-acetyloxy-7-[(5-amino-2-pyridinyl)oxy]-1H-indene obtained in Reference Example 49 in place of 1-acetoxy-6-[(5-amino-2-pyridinyl)oxy]-3,4-dihydronaphthalene and using 4-(trifluoromethyl)phenyl isocyanate in place of 3,4-dichlorophenyl isocyanate, the reaction was carried out to obtain the titled compound.

¹H-NMR (DMSO-d₆) δ ppm: 9.19 (s, 1H), 8.88 (s, 1H), 8.16 (d, 1H, J=3 Hz), 8.03 (dd, 1H, J=9 Hz, 3 Hz), 7.64 (s, 4H), 7.36 (t, 1H, J=8 Hz), 7.17 (d, 1H, J=8 Hz), 7.08 (d, 1H, J=9 Hz), 6.99 (d, 1H, J=8 Hz), 6.26 (s, 1H), 3.21 (s, 2H), 2.35 (s, 3H)

EXAMPLE 59

Synthesis of N1-(6-[(1-oxo-2,3-dihydro-1H-inden-4-yl)oxy]pyridin-3-yl)-N3-[4-(trifluoromethyl)phenyl]urea According to the same manner as that described in Example 56 except for using an equimolar amount of 4-[(5-amino-2-pyridinyl)oxy]-1-indanone obtained in Reference Example 17 in place of 1-acetoxy-6-[(5-amino-2-pyridinyl)oxy]-3,4-dihydronaphthalene and using 4-(trifluoromethyl)phenyl isocyanate in place of 3,4-dichlorophenyl isocyanate, the reaction was carried out to obtain the titled compound.

¹H-NMR (DMSO-d₆) δ ppm: 9.20 (s, 1H), 8.90 (s, 1H), 8.19 (d, 1H, J=2 Hz), 8.04 (dd, 1H, J=9 Hz, 2 Hz), 7.65 (s, 4H), 7.35–7.55 (m, 3H), 7.13 (d, 1H, J=9 Hz), 2.87 (t, 2H, J=6 Hz), 2.64 (t, 2H, J=6 Hz)

EXAMPLE 60

Synthesis of N1-{6-[(1-acetoxy-3,4-dihydronaphthalene-6-yl)oxy]pyridin-3-yl}-N3-[4-(trifluoromethyl)phenyl]urea According to the same manner as that described in Example 56 except for using an equimolar amount of 4-(trifluoromethyl)phenyl isocyanate in place of 3,4-dichlorophenyl isocyanate, the reaction was carried out to obtain the titled compound.

¹H-NMR (DMSO-d6) δ ppm: 2.28 (s, 3H), 2.34–2.42 (m, 2H), 2.76–2.81 (m, 2H), 5.67 (t, 1H, J=5 Hz), 6.87–7.12 (m, 4H), 7.64–7.69 (m, 4H), 7.98–8.03 (m, 1H), 8.22 (d, 1H, J=3 Hz), 8.90 (s, 1H), 9.20 (s, 1H)

EXAMPLE 61

Synthesis of N1-{6-[(1-acetoxy-3,4-dihydronaphthalene-5-yl)oxy]pyridin-3-yl}-N3-(3,4-dichlorophenyl)urea According to the same manner as that described in Example 56 except for using an equimolar amount of 1-acetoxy-5-[(5-amino-2-pyridinyl)oxy]-3,4-dihydronaphthalene obtained in Reference Example 55 in place of 1-acetoxy-6-[(5-amino-2-pyridinyl)oxy]-3,4-dihydronaphthalene, the reaction was carried out to obtain the titled compound.

¹H-NMR (DMSO-d₆) δ ppm: 9.07 (s, 1H), 8.86 (s, 1H), 8.12 (d, 1H, J=3 Hz), 7.99 (dd, 1H, J=9 Hz, 3 Hz), 7.86 (d, 1H, J=3 Hz), 7.52 (d, 1H, J=9 Hz), 7.34 (dd, 1H, J=9 Hz, 3 Hz), 7.23 (t, 1H, J=8 Hz), 7.02 (d, 1H, J=9 Hz), 6.99 (d, 2H, J=9 Hz), 5.74 (t, 1H, J=5 Hz), 2.62 (t, 2H, J=8 Hz), 2.33 (m, 2H), 2.30 (s, 3H)

EXAMPLE 62

Synthesis of N1-{6-[(5-oxo-5,6,7,8-tetrahydro-1-naphthalenyl)oxy]pyridin-3-yl}-N3-(3,4-dichlorophenyl)urea According to the same manner as that described in Example 56 except for using an equimolar amount of 5-[(5-amino-2-pyridinyl)oxy]-3,4-dihydro-1(2H)-naphthalenone obtained in Reference Example 20 in place of 1-acetoxy-6-[(5-amino-2-pyridinyl)oxy]-3,4-dihydronaphthalene, the reaction was carried out to obtain the titled compound.

¹H-NMR (DMSO-d₆) δ ppm: 9.09 (s, 1H), 8.87 (s, 1H), 8.13 (d, 1H, J=3 Hz), 8.00 (dd, 1H, J=9 Hz, 3 Hz), 7.86 (d, 1H, J=3 Hz), 7.77 (d, 1H, J=8 Hz), 7.52 (d, 1H, J=9 Hz), 7.30–7.45 (m, 3H), 7.08 (d, 1H, J=9 Hz), 2.74 (t, 2H, J=6 Hz), 2.60 (t, 2H, J=6 Hz), 2.00 (m, 2H)

EXAMPLE 63

Synthesis of N1-{6-[(1-acetoxy-3,4-dihydronaphthalene-5-yl)oxy]pyridin-3-yl}-N3-[4-(trifluoromethyl)phenyl]urea According to the same manner as that described in Example 56 except for using an equimolar amount of 1-acetoxy-5-[(5-amino-2-pyridinyl)oxy]-3,4-dihydronaphthalene obtained in Reference Example 55 in place of 1-acetoxy-6-[(5-amino-2-pyridinyl)oxy]-3,4-dihydronaphthalene and using 4-(trifluoromethyl)phenyl isocyanate in place of 3,4-dichlorophenyl isocyanate, the reaction was carried out to obtain the titled compound.

¹H-NMR (DMSO-d₆) δ ppm: 9.35 (s, 1H), 9.03 (s, 1H), 8.15 (d, 1H, J=3 Hz), 8.01 (dd, 1H, J=9 Hz), 7.67 (d, 2H, J=9 Hz), 7.62 (d, 2H, J=9 Hz), 7.23 (t, 1H, J=8 Hz), 7.03 (d, 1H, J=8 Hz), 6.99 (d, 2H, J=8 Hz), 5.74 (t, 1H, J=5 Hz), 2.62 (t, 2H, J=8 Hz), 2.32 (m, 2H), 2.30 (s, 3H)

EXAMPLE 64

Synthesis of N1-{6-[(5-oxo-5,6,7,8-tetrahydro-1-naphthalenyl)oxy]pyridin-3-yl}-N3-[4-(trifluoromethyl)phenyl]urea According to the same manner as that described in Example 56 except for using an equimolar amount of 5-[(5-amino-2-pyridinyl)oxy]-3,4-dihydro-1(2H)-naphthalenone obtained in Reference Example 20 in place of 1-acetoxy-6-[(5-amino-2-pyridinyl)oxy]-3,4-dihydronaphthalene and using 4-(trifluoromethyl)phenyl isocyanate in place of 3,4-dichlorophenyl isocyanate, the reaction was carried out to obtain the titled compound.

¹H-NMR (DMSO-d₆) δ ppm: 9.31 (s, 1H), 8.99 (s, 1H), 8.16 (d, 1H, J=3 Hz), 8.02 (dd, 1H, J=9 Hz, 3 Hz), 7.77 (d, 1H, J=8 Hz), 7.67 (d, 2H, J=9 Hz), 7.63 (d, 2H, J=9 Hz), 7.40 (t, 1H, J=8 Hz), 7.33 (d, 1H, J=8 Hz), 7.08 (d, 1H, J=8 Hz), 2.74 (t, 2H, J=6 Hz), 2.61 (t, 2H;, J=6 Hz), 1.99 (m, 2H)

EXAMPLE 65

Synthesis of N1-{6-[(3,4-dihydro-1(2H)-naphthalenon-6-yl)oxy]pyridin-3-yl}-N3-[4-(trifluoromethyl)phenyl]urea To a solution of N1-{1-acetoxy-6-[(3,4-dihydronaphthalene-6-yl)oxy]pyridine-3-yl}-N3-[4-(trifluoromethyl)phenyl]urea (450 mg) in ethanol (20 ml), 980 mg of potassium carbonate was added and the mixture was stirred at room temperature for 40 minutes. After the reaction mixture was filtered and concentrated, the residue was dissolved in ethyl acetate and the solution was washed with water. After drying over anhydrous magnesium sulfate, the solvent was distilled off. The residue was washed with ether to obtain 290 mg of the titled compound as a white powder.

¹H-NMR (DMSO-d₆) δ ppm: 1.99–2.08 (m, 2H), 2.56–2.61 (m, 2H), 2.92 (t, 2H, J=6 Hz), 7.00–7.02 (m, 2H), 7.12 (d, 1H, J=9 Hz), 7.62–7.70 (m, 4H), 7.88–7.92 (m, 1H), 8.03–8.08 (m, 1H), 8.29 (d, 1H, J=3 Hz), 8.97(s, 1H), 9.24 (s, 1H)

EXAMPLE 66

Synthesis of E-1-{6-[(1-oxo-2,3-dihydro-1H-indene-4-yl)oxy]-3-pyridinyl}-2-[4-(trifluoromethyl)phenyl]ethene To a solution of 4-[(5-formyl-2-pyridinyl)oxy]-1-indanone (1.0 g) obtained in Reference Example 60 in dichloromethane (5 ml), [4-(trifluoromethyl)phenyl] benzyltriphenylphosphonium bromide (2.0 g) and potassium t-butoxide (0.46 g) were added under ice cooling. The reaction mixture was stirred for 5 hours gradually warming up to room temperature. To the reaction mixture, dichloromethane and water were added and then the organic layer was washed with water, saturated sodium bicarbonate solution and saturated sodium chloride solution. The organic layer was dried over anhydrous magnesium sulfate and the solvent was distilled off. The residue was purified by silica gel column chromatography (eluent: hexane/ethyl acetate= 3:2) to obtain 160 mg of the titled compound.

¹H-NMR (CDCl₃) δ ppm: 2.63–2.68 (m, 2H), 2.92–2.96 (m, 2H), 6.60 (d, 1H, J=12 Hz), 6.69 (d, 1H, J=12 Hz), 6.87 (d, 1H, J=9 Hz), 7.39–7.44 (m, 1H), 7.50–7.56 (m, 3H), 7.61–7.64 (m, 1H), 8.00 (d, 1H, J=2 Hz)

EXAMPLE 67

Synthesis of Z-1-{6-[(1-oxo-2,3-dihydro-1H-indene-4-yl)oxy]-3-pyridinyl}-2-[4-(trifluoromethyl)phenyl]ethene According to the same manner as that described in Example 66, the titled compound was obtained.

¹H-NMR (CDCl₃) δ ppm: 2.66–2.71 (m, 2H), 2.96–3.00 (m, 2H), 7.03–7.17 (m, 3H), 7.37–7.40 (m, 1H), 7.43–7.48

(m, 1H), 7.57–7.64 (m, 4H), 7.65–7.68 (m, 1H), 7.94–7.98 (m, 1H), 8.24 (d, 1H, J=2 Hz)

EXAMPLE 68

Synthesis of E-1-{6-[(1-oxo-2,3-dihydro-1H-indene-4-yl)oxy]-3-pyridinyl}-2-(3,4-dichlorophenyl)ethene According to the same manner as that described in Example 66 except for using (3,4-dichlorophenyl) benzyltriphenylphosphonium bromide in place of (4-trifluorophenyl)benzyltriphenylphosphonium bromide, the titled compound was obtained.

$^1$H-NMR (CDCl$_3$) δ ppm: 2.66–2.71 (m, 2H), 2.95–2.99 (m, 2H), 6.92 (d, 1H, J=17 Hz), 7.00–7.06 (m, 2H), 7.32 (dd, 1H, J=2 Hz, 9 Hz), 7.36–7.40 (m, 1H), 7.41–7.48 (m, 2H), 7.58 (d, 1H, J=2 Hz), 7.65–7.68 (m, 1H), 7.90–7.95 (m, 1H), 8.21 (d, 1H, J=2 Hz)

EXAMPLE 69

Synthesis of Z-1-{6-[(1-oxo-2,3-dihydro-1H-indene-4-yl)oxy]-3-pyridinyl}-2-(3,4-dichlorophenyl)ethene According to the same manner as that described in Example 68, the titled compound was obtained.

$^1$H-NMR (CDCl$_3$) δ ppm: 2.64–2.68 (m, 2H), 2.91–2.95 (m, 2H), 6.57 (s, 2H), 6.87–6.91 (m, 1H), 7.05 (dd, 1H, J=2 Hz, 8 Hz), 7.29 (d, 1H, J=2 Hz), 7.31 (d, 1H, J=8 Hz), 7.34–7.37 (m, 1H), 7.39–7.45 (m, 1H), 7.54–7.58 (m, 1H), 7.61–7.64 (m, 1H), 7.98 (d, 1H, J=2 Hz)

EXAMPLE 70

Synthesis of 6-[(3-acetoxy-1H-indene-7-yl)oxy]-N3-[4-(trifluoromethyl) phenyl]nicotinamide According to the same manner as that described in Example 46 except for using an equimolar amount of 6-[(1-oxo-2,3-dihydro-1H-indene-4-yl)oxy]-N3-[4-(trifluoromethyl)pheny]nicotinamide obtained in Reference Example 39 in place of 3-4-dichloro-N1-(6-[(1-oxo-2,3-dihydro-1H-indene-4-yl)oxy]-3-pyridinyl)benzamide, the reaction was carried out to obtain the titled compound.

$^1$H-NMR (DMSO-d$_6$) δ ppm: 10.63 (s, 1H), 8.70 (s, 1H), 8.40 (dd, 1H, J=9 Hz, 3 Hz), 7.98 (d, 2H, J=9 Hz), 7.74 (d, 2H, J=9 Hz), 7.42 (t, 1H, J=8 Hz), 7.25 (m, 2H), 7.11 (d, 1H, J=8 Hz), 6.28 (s, 1H), 3.23 (s, 2H), 2.36 (s, 3H)

Preparation Example

Preparation Example is described below.

Preparation Example 1

| | |
|---|---|
| 3,4-dichloro-N1-{6-[(1-oxo-2,3-dihydro-1H-inden-4-yl)oxy]-3-pyridinyl}benzamide | 100 g |
| Abicel (trade name, manufactured by Asahi Kasei Corp. | 40 g |
| Corn starch | 30 g |
| Magnesium stearate | 2 g |
| TC-5 (trade name, manufactured by Shinetsu Corp., hydroxypropyl methylcellulose) | 10 g |
| Polyethylene glycol-6000 | 3 g |
| Castor oil | 40 g |
| Ethanol | q.s. |

After 3,4-dichloro-N1-{6-[(1-oxo-2,3-dihydro-1H-inden-4-yl)oxy]-3-pyridinyl}benzamide obtained in Example 1, Abicel, corn starch and magnesium stearate are mixed and ground, the mixture is compressed by using a punch for sugar coating R10 mm. The resulting tablets are coated with a film coating agent comprising TC-5, polyethylene glycol-6000, castor oil and ethanol to produce film coated tablets of the above composition.

Test Example

The pyridine derivatives (test compounds) obtained in Examples 1–2, 9–10, 21, 25, 29, 33–37, 39, 42, 44 and 46 were subjected to the following collagen synthesis test.

Test for Inhibition of Collagen Synthesis

Preparation of Plasma Derived Serum (PDS)

Plasma obtained by centrifugation of rabbit blood was centrifuged again to remove platelets, and dialysis of the resulting supernatant was carried out against a Phosphate Buffered Saline (PBS) containing 0.01% (w/v) calcium chloride and 0.01% (w/v) magnesium chloride. Then, centrifugation was carried out to remove the residue and the resulting supernatant was immobilized at 56° C. for 30 minutes. The immobilized supernatant was sterilized by using a filter (0.22 μm) to prepare Plasma Derived Serum (PDS).

Method for Determination

Human Ito cells (LI90) were plated in DULBECCO's modified eagle medium (DMEM) containing 10% fetal bovine serum and cultured in an incubator in the presence of 5% carbon dioxide (CO$_2$) for 24 hours at 37° C., and then washed with PBS and cultured in Eagle's minimum essential medium (MEM) containing 2% PDS for additional 3 days. The cultured cells were washed with PBS and cultured together with the test compounds in MEM containing 10 PM hTGF (transforming growth factor) β-1 (containing 2% PDS based on the total amount of MEM) for 16 hours. Then, the cultured L190 was washed with PBS and RI (radioisotope) labeling was carried out in MEM containing $^3$H proline as a radioactive labeled compound and 0.25 mM ascorbic acid for 24 hours. This cultured supernatant was precipitated by using trichloroacetic acid (TCA), and then the radioactivity in an acid soluble fraction was measured and the resulting measured value was taken as collagen synthesis activity.

By comparing the radioactivity in the cultured supernatant containing the test compound with the radioactivity in the cultured supernatant containing no test compound (control), the collagen synthesis inhibition activity (T/C) was calculated by the following equation:

T/C=(radioactivity in cultured supernatant containing test compound)/(radioactivity in cultured supernatant of control).

IC$_{50}$ was determined as the concentration (μM) at which the collagen systhesis can be inhibited by 50% (concentration of the test compound wherein C$_{50}$=T/C corresponds to 0.5).

These test results are shown in Table 1.

TABLE 1

| | IC$_{50}$ (μM) |
|---|---|
| Example 1 | 2.14 |
| Example 2 | 2.90 |
| Example 9 | 2.34 |
| Example 10 | 2.60 |

TABLE 1-continued

| | IC$_{50}$ ($\mu$M) |
|---|---|
| Example 21 | 2.92 |
| Example 25 | 2.70 |
| Example 29 | 1.58 |
| Example 33 | 3.88 |
| Example 34 | 2.15 |
| Example 35 | 2.43 |
| Example 36 | 3.72 |
| Example 37 | 2.52 |
| Example 39 | 0.55 |
| Example 42 | 2.29 |
| Example 44 | 0.92 |
| Example 46 | 1.12 |

INDUSTRIAL APPLICABILITY

The pyridine derivative of the present invention is superior in effect of inhibiting collagen production. The pyridine derivative of the present invention is also superior in characteristics such as duration time of drug efficacy, stability, absorption/excretion and the like. Accordingly, the pyridine derivative can be used for prophylaxis or treatment of fibrosis (e.g. hepatic fibrosis, pulmonary fibrosis, etc.) caused by an increase in collagen production.

The disclosure of Japanese Patent Application Serial Nos. 10-78083 and 10-251552, filed on Mar. 25, 1998 and Sep. 4, 1998, respectively, are incorporated herein by reference.

What is claimed is:

1. A pyridine derivative represented by the general formula (1):

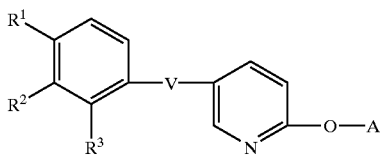

(1)

wherein $R^1$ represents a halogen atom or a halogen-substituted lower alkyl group; $R^2$ and $R^3$ are the same or different and represent a hydrogen atom or a halogen atom; V represents a group: —C(=O)—NH—, a group: —NH—C(=O)—, a group: —NH—C(=O)—NH— or a group: —CH=CH—; A represents a group $A^1$:

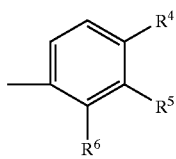

$A^1$ (wherein $R^4$ represents a hydrogen atom or a 2-lower alkyl-1,3-dioxolane group; $R^5$ represents a hydrogen atom or a 2-lower alkyl-1,3-dioxolane group; and $R^6$ represents a hydrogen atom, provided that one of $R^4$ and $R^5$ is a 2-lower alkyl-1,3-dioxolane group and the other of $R^4$ and $R^5$ is a hydrogen atom), a group $A^2$:

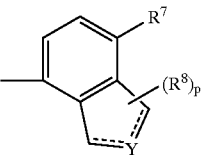

$A^2$ ((wherein $R^7$ represents a hydrogen atom or a lower alkyl group; $R^8$ may be the same or different and represents a hydrogen atom, a hydroxyl group, an oxo group, a lower alkanoyloxy group, an aroyloxy group, a lower alkoxy group, a group:

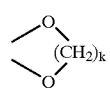

(wherein k represents an integer of 1 to 3) or a group: =N—OR$^{10}$ (wherein R$^{10}$ represents a hydrogen atom, a lower alkyl group or a lower alkanoyl group); p represents an integer of 1 to 2;

represents a single bond or a double bond; Y represents a group: —(CH$_2$)$_m$—, a group: =CH(CH$_2$)$_{m-1}$— or a group: —(CH$_2$)$_{m-1}$CH=; and m represents an integer of 1 to 3)) or a group $A^3$:

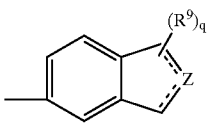

$A^3$ ((wherein $R^9$ may be the same or different and represents a hydrogen atom, a hydroxyl group, an oxo group, a lower alkanoyloxy group, an aroyloxy group, a lower alkoxy group, a group:

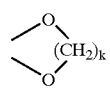

(wherein k represents an integer of 1 to 3) or a group; l represents an a hydrogen atom, a lower alkyl group or a lower alkanoyl group); q represents an integer of 1 to 2;

represents a single bond or a double bond; Z represents a group: —(CH$_2$)$_n$—, a group: =CH(CH$_2$)$_{n-1}$— or a group: —(CH$_2$)$_{n-1}$CH=; and n represents an integer of 1 to 3)) or a salt thereof.

2. The pyridine derivative according to claim 1, wherein A is the group $A^2$ or $A^3$, or a salt thereof.

3. The pyridine derivative according to claim 2, wherein m and n are 1 or 2, or a salt thereof.

4. The pyridine derivative according to claim 3, wherein $R^8$ and $R^9$ are an oxo group or a lower alkanoyloxy group, or a salt thereof.

5. The pyridine derivative according to claim 1, wherein V is the group: —C(=O)—NH—, the group: —NH—C(=O)— or the group: —NH—C(=O)—NH—, or a salt thereof.

6. The pyridine derivative according to claim 5, wherein A is the group $A_2$ or $A^3$, or a salt thereof.

7. The pyridine derivative according to claim 1, wherein $R^1$ and $R^2$ are respectively a halogen atom, or a salt thereof.

8. The pyridine derivative according to claim 1, wherein $R^1$ is a halogen-substituted lower alkyl group, or a salt thereof.

9. The pyridine derivative according to claim 6, wherein $R^1$ and $R^2$ are respectively a halogen atom, or a salt thereof.

10. The pyridine derivative according to claim 6, wherein $R^1$ is a halogen-substituted alkyl group, or a salt thereof.

11. The pyridine derivative according to claim 7, wherein A is the group $A^2$, or a salt thereof.

12. The pyridine derivative according to claim 11, wherein V is the group: —C(=O)—NH—, or a salt thereof.

13. The pyridine derivative according to claim 11, wherein V is the group: —NH—C(=O)—NH—, or a salt thereof.

14. The pyridine derivative according to claim 7, wherein A is the group $A^3$, or a salt thereof.

15. The pyridine derivative according to claim 14, wherein V is the group: —NH—C(=O)—NH—, or a salt thereof.

16. The pyridine derivative according to claim 8, wherein A is the group $A^2$, or a salt thereof.

17. The pyridine derivative according to claim 8, wherein A is the group $A^3$, or a salt thereof.

18. The pyridine derivative according to claim 16, wherein V is the group: —NH—C(=O)—, or a salt thereof.

19. The pyridine derivative according to claim 16, wherein V is the group: —NH—C(=O)—NH—, or a salt thereof.

20. The pyridine derivative according to claim 17, wherein V is the group: —NH—C(=O)—NH—, or a salt thereof.

21. The pyridine derivative according to claim 12, wherein Y is a group: —CH= or —CH$_2$=, $R^7$ is a hydrogen atom, $R^8$ is an oxo group, a lower alkanoyloxy group or the group: —O—CH$_2$—CH$_2$—O—, or a salt thereof.

22. The pyridine derivative according to claim 13, wherein Y is the group: —CH=, —CH$_2$—CH$_2$— or —CH$_2$—CH=, $R^7$ is a hydrogen atom, $R^8$ is an oxo group or a lower alkanoyloxy group, or a salt thereof.

23. The pyridine derivative according to claim 15, wherein Z is a group: —CH$_2$—CH=, $R^9$ is a lower alkanoyloxy group, or a salt thereof.

24. The pyridine derivative according to claim 18, wherein Y is the group: —CH$_2$—, $R^7$ is a hydrogen atom, $R^8$ is an oxo group, or a salt thereof.

25. The pyridine derivative according to claim 19, wherein Y is the group: —CH$_2$—, —CH= or —CH$_2$—CH=, $R^7$ is a hydrogen atom, $R^8$ is a lower alkanoyloxy group, or a salt thereof.

26. The pyridine derivative according to claim 20, wherein Z is the group,: —CH$_2$—CH=, $R^9$ is a lower alkanoyloxy group, or a salt thereof.

27. A pharmaceutical composition for prophylaxis or treatment of fibrosis, which comprises an effective amount of a compound of the general formula (1)

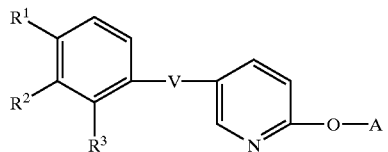

wherein $R^1$ represents a halogen atom or a halogen-substituted lower alkyl group; $R^2$ and $R^3$ are the same or different and represent a hydrogen atom or a halogen atom; V represents a group: —C(=O)—NH—, a group: —NH—C(=O)—, a group: —NH—C(=O)—NH— or a gruo: —CH=CH—; A represents a group $A^1$:

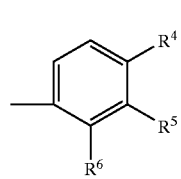

(wherein $R^4$ represents a hydrogen atom or a 2-lower alkyl-1,3-dioxolane group; $R^5$ represents a hydrogen atom or a 2-lower alkyl-1,3-dioxolane group; and $R^6$ represents a hydrogen atom, provided that one of $R^4$ and $R^5$ is a 2-lower alkyl-1,3-dioxolane group and the other of $R^4$ and $R^5$ is a hydrogen atom), a group $A^2$:

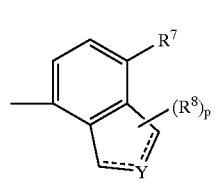

((wherein $R^7$ represents a hydrogen atom or a lower alkyl group; $R^8$ may be the same or different and represents a hydrogen atom, a hydroxyl group, an oxo group, a lower alkanoyloxy group, an aroyloxy group, a lower alkoxy group, a group:

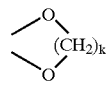

(wherein k represents an integer of 1 to 3) or a group: =N—OR$^{10}$ (wherein R$^{10}$ represents a hydrogen atom, a lower alkyl group or a lower alkanoyl group); p represents an integer of 1 to 2;

---- represents a single bond or a double bond; Y represents a group: —(CH$_2$)$_m$—, a group: =CH(CH$_2$)$_{m-1}$— or a group: —(CH$_2$)$_{m-1}$CH=; and m represents an integer of 1 to 3)) or a group $A^3$:

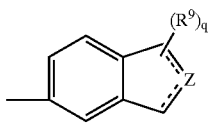

((wherein $R^9$ may be the same or different and represents a hydrogen atom, a hydroxyl group, an oxo group, a lower alkanoyloxy group, an aroyloxy group, a lower alkoxy group, a group:

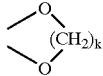

(wherein k represents an integer of 1 to 3) or a group: $=N-OR^{10}$ (wherein $R^{10}$ represents a hydrogen atom, a lower alkyl group or a lower alkanoyl group); q represents an integer of 1 to 2;

isclosure of the Inventionrepresents a single bond or a double bond; Z represents a group: $-(CH_2)_n-$, a group: $=CH(CH_2)_{n-1}-$ or a group: $-(CH_2)_{n-1}CH=$; and n represents an integer of 1 to 3)) or a pharmaceutically acceptable salt thereof and a pharmaceutically acceptable carrier, diluent and/or excipient.

28. A method for inhibiting fibrogenesis caused by excess production of collagen in a mammal which comprises administering to said mammal a pharmaceutically effective amount of a compound of the general formula (1)

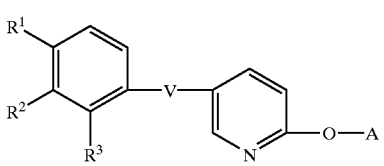

wherein $R^1$ represents a halogen atom or a halogen-substituted lower alkyl group; $R^2$ and $R^3$ are the same or different and represent a hydrogen atom or a halogen atom; V represents a group: $-C(=O)-NH-$, a group: $-NH-C(=O)-$, a group: $-NH-C(=O)-NH-$ or a group: $-CH=CH-$; A represents a group $A^1$:

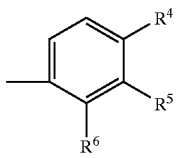

(wherein $R^4$ represents a hydrogen atom, a 2-lower alkyl-1,3-dioxolane group or a hydroxy-substituted lower alkyl group; $R^5$ represents a hydrogen atom, or a 2-lower alkyl-1,3-dioxolane group; and $R^6$ represents a hydrogen atom, provided that $R^4$ and $R^5$ do not both represent a hydrogen atom at the same time), a group $A^2$:

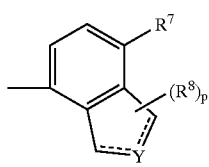

((wherein $R^7$ represents a hydrogen atom or a lower alkyl group; $R^8$ may be the same or different and represents a hydrogen atom, a hydroxyl group, an oxo group, a lower alkanoyloxy group, an aroyloxy group, a lower alkoxy group, a group:

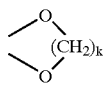

(wherein k represents an integer of 1 to 3) or a group: $=N-OR^{10}$ (wherein $R^{10}$ represents a hydrogen atom, a lower alkyl group or a lower alkanoyl group); p represents an integer of 1 to 2;

represents a single bond or a double bond; Y represents a group: $-(CH_2)_m-$, a group: $=CH(CH_2)_{m-1}-$ or a group: $-(CH_2)_{m-1}CH-$; and m represents an integer of 1 to 3)) or a group $A_3$:

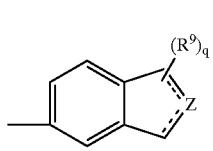

((wherein $R^9$ may be the same or different and represents a hydrogen atom, a hydroxyl group, an oxo group, a lower alkanoyloxy group, an aroyloxy group, a lower alkoxy group, a group:

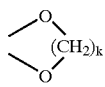

(wherein k represents an integer of 1 to 3) or a group: $=N-OR^{10}$ (wherein $R^{10}$ represents a hydrogen atom, a lower alkyl group or a lower alkanoyl group); q represents an integer of 1 to 2;

represents a single bond or a double bond; Z represents a group: $-(CH_2)_n-$, a group: $=CH(CH_2)_{n-1}-$ or a group: $-(CH_2)_{n-1}CH=$; and n represents an integer of 1 to 3)) or a pharmaceutically salt thereof.

* * * * *

UNITED STATES PATENT AND TRADEMARK OFFICE
CERTIFICATE OF CORRECTION

PATENT NO.    : 6,511,995 B1
DATED         : January 28, 2003
INVENTOR(S)   : Kouji Edamatsu et al.

It is certified that error appears in the above-identified patent and that said Letters Patent is hereby corrected as shown below:

Column 62,
Line 48, "group; 1" should read -- group: =N-OR$^{10}$ (wherein R$^{10}$ --.
Line 49, "represents an a" should read -- represents a --.

Column 63,
Line 42, "-CH$_2$=," should read -- -CH$_2$-, --.
Line 62, "group,:" should read -- group: --.

Column 64,
Line 15, "gruo:" should read -- group: --.

Column 65,
Line 25, "isclosure of the Inventionrepresents a" should read -- represents a --.

Column 66,
Line 33, "-(CH$_2$)$_{m-1}$CH-;" should read -- -(CH$_2$)$_{m-1}$CH=; --.

Signed and Sealed this

First Day of July, 2003

JAMES E. ROGAN
*Director of the United States Patent and Trademark Office*